US012336723B2

(12) United States Patent
Fouts et al.

(10) Patent No.: US 12,336,723 B2
(45) Date of Patent: *Jun. 24, 2025

(54) METHOD AND APPARATUS FOR TREATING A JOINT, INCLUDING THE TREATMENT OF CAM-TYPE FEMOROACETABULAR IMPINGEMENT IN A HIP JOINT AND PINCER-TYPE FEMOROACETABULAR IMPINGEMENT IN A HIP JOINT

(71) Applicant: Stryker Corporation, Kalamazoo, MI (US)

(72) Inventors: Brian Fouts, Morgan Hill, CA (US); Brady Woolford, Mapleton, UT (US); Christopher Zeh, Parker, CO (US)

(73) Assignee: Stryker Corporation, Portage, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 18/190,956

(22) Filed: Mar. 27, 2023

(65) Prior Publication Data

US 2023/0414231 A1 Dec. 28, 2023

Related U.S. Application Data

(63) Continuation of application No. 17/143,091, filed on Jan. 6, 2021, now Pat. No. 11,612,402, which is a
(Continued)

(51) Int. Cl.
*A61B 17/17* (2006.01)
*A61B 34/00* (2016.01)
(Continued)

(52) U.S. Cl.
CPC ........ *A61B 17/1703* (2013.01); *A61B 17/175* (2013.01); *A61B 34/10* (2016.02);
(Continued)

(58) Field of Classification Search
CPC .............. G06F 3/04845; G06F 3/0488; A61B 17/1659; A61B 17/1703; A61B 17/175;
(Continued)

(56) References Cited

U.S. PATENT DOCUMENTS

| 5,437,672 A * | 8/1995 | Alleyne ................. A61B 90/00 |
| | | 606/279 |
| 5,862,249 A | 1/1999 | Jang et al. |

(Continued)

FOREIGN PATENT DOCUMENTS

| CN | 101518447 A | 9/2009 |
| CN | 102194047 A | 9/2011 |

(Continued)

OTHER PUBLICATIONS

Agus et al. (2003). "A haptic model of a bone-cutting burr," Studies in Health Technology and Informatics 94: 4-10.
(Continued)

*Primary Examiner* — Manuchehr Rahmjoo
(74) *Attorney, Agent, or Firm* — Morrison & Foerster LLP

(57) ABSTRACT

A computer visual guidance system for guiding a surgeon through an arthroscopic debridement of a bony pathology, wherein the computer visual guidance system is configured to: (i) receive a 2D image of the bony pathology from a source; (ii) automatically analyze the 2D image so as to determine at least one measurement with respect to the bony pathology; (iii) automatically annotate the 2D image with at least one annotation relating to the at least one measurement determined with respect to the bony pathology so as to create an annotated 2D image; and (iv) display the annotated 2D image to the surgeon so as to guide the surgeon through the arthroscopic debridement of the bony pathology.

31 Claims, 50 Drawing Sheets

Related U.S. Application Data continuation of application No. 15/818,394, filed on Nov. 20, 2017, now Pat. No. 10,918,398.

(60) Provisional application No. 62/423,890, filed on Nov. 18, 2016.

(51) Int. Cl.
| | |
|---|---|
| *A61B 34/10* | (2016.01) |
| *A61B 34/20* | (2016.01) |
| *G06T 7/00* | (2017.01) |
| *G06T 11/00* | (2006.01) |
| *G06T 11/60* | (2006.01) |
| *A61B 17/16* | (2006.01) |
| *A61B 90/00* | (2016.01) |
| *G06F 3/04845* | (2022.01) |
| *G06F 3/0488* | (2022.01) |

(52) U.S. Cl.
CPC ............. *A61B 34/20* (2016.02); *A61B 34/25* (2016.02); *G06T 7/0012* (2013.01); *G06T 11/00* (2013.01); *G06T 11/60* (2013.01); *A61B 2017/1602* (2013.01); *A61B 17/1659* (2013.01); *A61B 2034/107* (2016.02); *A61B 2034/2051* (2016.02); *A61B 2034/2065* (2016.02); *A61B 2090/067* (2016.02); *A61B 2090/365* (2016.02); *A61B 2090/3966* (2016.02); *G06F 3/04845* (2013.01); *G06F 3/0488* (2013.01); *G06T 2207/10116* (2013.01); *G06T 2207/30008* (2013.01)

(58) Field of Classification Search
CPC ...... A61B 2017/1602; A61B 2034/107; A61B 2034/2051; A61B 2034/2065; A61B 2090/067; A61B 2090/365; A61B 2090/3966; A61B 34/10; A61B 34/20; A61B 34/25; G06T 11/00; G06T 11/60; G06T 2207/10116; G06T 2207/30008; G06T 7/0012

See application file for complete search history.

(56) References Cited

U.S. PATENT DOCUMENTS

| | | | |
|---|---|---|---|
| 6,161,080 | A | 12/2000 | Aouni-Ateshian et al. |
| 6,205,411 | B1 | 3/2001 | Digioia, III et al. |
| 6,697,664 | B2 | 2/2004 | Kienzle, III et al. |
| 7,167,738 | B2 | 1/2007 | Schweikard et al. |
| 7,231,076 | B2 | 6/2007 | Fu et al. |
| 7,327,865 | B2 | 2/2008 | Fu et al. |
| 7,643,862 | B2 | 1/2010 | Schoenefeld |
| 7,689,042 | B2 | 3/2010 | Brunner et al. |
| 7,783,008 | B2 | 8/2010 | Jabri |
| 7,949,386 | B2 | 5/2011 | Buly et al. |
| 8,014,984 | B2 | 9/2011 | Iannotti et al. |
| 8,052,623 | B2 | 11/2011 | Haimerl et al. |
| 8,090,166 | B2 | 1/2012 | Rappaport et al. |
| 8,152,816 | B2 | 4/2012 | Tuma et al. |
| 8,328,816 | B2 | 12/2012 | Beaule |
| 8,369,593 | B2 | 2/2013 | Peng et al. |
| 8,594,397 | B2 | 11/2013 | Haimerl et al. |
| 8,611,697 | B2 | 12/2013 | Nathaniel et al. |
| 8,678,125 | B2 | 3/2014 | Kosugi et al. |
| 8,679,125 | B2 | 3/2014 | Smith et al. |
| 8,694,075 | B2 | 4/2014 | Groszmann |
| 8,696,603 | B2 | 4/2014 | Takahashi et al. |
| 8,702,805 | B2 | 4/2014 | Trabish |
| 8,715,289 | B2 | 5/2014 | Smith |
| 8,774,900 | B2 | 7/2014 | Buly et al. |
| 8,828,009 | B2 | 9/2014 | Allen et al. |
| 8,831,324 | B2 | 9/2014 | Penenberg |
| 8,858,563 | B2 | 10/2014 | Philippon et al. |
| 8,888,782 | B2 | 11/2014 | Smith et al. |
| 8,890,511 | B2 | 11/2014 | Belew |
| 8,900,320 | B2 | 12/2014 | Frederick et al. |
| 8,923,584 | B2 | 12/2014 | Chabanas et al. |
| 8,934,961 | B2 | 1/2015 | Lakin et al. |
| 8,958,611 | B2 | 2/2015 | Ikits |
| 8,965,108 | B2 | 2/2015 | Chabanas et al. |
| 9,020,223 | B2 | 4/2015 | Chabanas et al. |
| 9,082,319 | B2 | 7/2015 | Shimada et al. |
| 9,113,921 | B2 | 8/2015 | Lang et al. |
| 9,113,971 | B2 | 8/2015 | Metzger et al. |
| 9,122,670 | B2 | 9/2015 | Chabanas et al. |
| 9,123,155 | B2 | 9/2015 | Cunningham et al. |
| 9,173,716 | B2 | 11/2015 | Kasodekar et al. |
| 9,183,629 | B2 | 11/2015 | Chabanas et al. |
| 9,220,567 | B2 | 12/2015 | Sutherland et al. |
| 9,271,804 | B2 | 3/2016 | Wu |
| 9,320,421 | B2 | 4/2016 | Chabanas et al. |
| 9,345,495 | B2 | 5/2016 | Gibson et al. |
| 9,345,552 | B2 | 5/2016 | Janik et al. |
| 9,386,993 | B2 | 7/2016 | Meridew et al. |
| 9,402,726 | B2 | 8/2016 | Linderman et al. |
| 9,443,346 | B2 | 9/2016 | Ikits |
| 9,480,534 | B2 | 11/2016 | Bowling et al. |
| 9,514,533 | B2 | 12/2016 | Chabanas et al. |
| 9,672,662 | B2 | 6/2017 | Scanlan et al. |
| 10,070,903 | B2 | 9/2018 | Blau |
| 10,105,168 | B2 | 10/2018 | Blau |
| 10,709,394 | B2 | 7/2020 | Zhou et al. |
| 10,918,398 | B2 | 2/2021 | Fouts et al. |
| 2003/0176783 | A1 | 9/2003 | Hu |
| 2004/0242987 | A1 | 12/2004 | Liew et al. |
| 2005/0096535 | A1 | 5/2005 | de la Barrera |
| 2007/0016008 | A1 | 1/2007 | Schoenefeld |
| 2007/0129630 | A1 | 6/2007 | Shimko |
| 2007/0135706 | A1 | 6/2007 | Shimko et al. |
| 2007/0249967 | A1 | 10/2007 | Buly et al. |
| 2007/0260256 | A1 | 11/2007 | Beaule |
| 2008/0039717 | A1 | 2/2008 | Frigg et al. |
| 2008/0058641 | A1 | 3/2008 | Shimko |
| 2008/0300478 | A1 | 12/2008 | Zuhars |
| 2009/0000626 | A1 | 1/2009 | Quaid et al. |
| 2009/0209851 | A1 | 8/2009 | Blau |
| 2010/0049493 | A1 | 2/2010 | Haimerl |
| 2010/0284590 | A1 | 11/2010 | Krishnan et al. |
| 2011/0190774 | A1 | 8/2011 | Nikolchev et al. |
| 2011/0213374 | A1 | 9/2011 | Fitz et al. |
| 2011/0213377 | A1 | 9/2011 | Lang et al. |
| 2011/0213379 | A1 | 9/2011 | Blau et al. |
| 2011/0213428 | A1 | 9/2011 | Fitz et al. |
| 2011/0213429 | A1 | 9/2011 | Lang et al. |
| 2011/0238431 | A1 | 9/2011 | Cionni et al. |
| 2011/0270295 | A1 | 11/2011 | Litvack et al. |
| 2011/0301654 | A1 | 12/2011 | Wozencroft et al. |
| 2012/0066892 | A1 | 3/2012 | Lang et al. |
| 2012/0271147 | A1 | 10/2012 | Kim et al. |
| 2013/0083984 | A1 | 4/2013 | Chabanas et al. |
| 2013/0089253 | A1 | 4/2013 | Chabanas et al. |
| 2013/0114866 | A1* | 5/2013 | Kasodekar ........... A61B 5/1071 382/128 |
| 2013/0191099 | A1 | 7/2013 | Krekel |
| 2013/0211232 | A1 | 8/2013 | Murphy et al. |
| 2013/0211386 | A1 | 8/2013 | Blau et al. |
| 2013/0211408 | A1 | 8/2013 | Kather et al. |
| 2013/0211531 | A1 | 8/2013 | Steines et al. |
| 2013/0314440 | A1 | 11/2013 | Simon et al. |
| 2013/0315371 | A1 | 11/2013 | Simon et al. |
| 2014/0079303 | A1 | 3/2014 | Pfrengle et al. |
| 2014/0187908 | A1 | 7/2014 | Ellermann et al. |
| 2014/0243833 | A1 | 8/2014 | Smith |
| 2014/0278322 | A1 | 9/2014 | Jaramaz et al. |
| 2014/0316417 | A1 | 10/2014 | Kaiser et al. |
| 2014/0322197 | A1 | 10/2014 | Brooks |
| 2014/0378982 | A1 | 12/2014 | Philippon et al. |
| 2015/0066151 | A1 | 3/2015 | Frederick et al. |
| 2015/0106024 | A1 | 4/2015 | Lightcap et al. |
| 2015/0133945 | A1 | 5/2015 | Dushyant et al. |
| 2015/0182295 | A1 | 7/2015 | Bozung et al. |
| 2015/0185846 | A1 | 7/2015 | Otto et al. |

(56) References Cited

U.S. PATENT DOCUMENTS

| | | |
|---|---|---|
| 2015/0265266 A1 | 9/2015 | Sanchez et al. |
| 2015/0265362 A1 | 9/2015 | Andersson et al. |
| 2015/0269727 A1 | 9/2015 | Chabanas et al. |
| 2015/0355298 A1 | 12/2015 | Ben-Eliezer et al. |
| 2016/0038160 A1 | 2/2016 | Metzger et al. |
| 2016/0066770 A1 | 3/2016 | Barbato et al. |
| 2016/0074124 A1 | 3/2016 | Fitz et al. |
| 2016/0113720 A1 | 4/2016 | Lavallee et al. |
| 2016/0135816 A1 | 5/2016 | Lavallee et al. |
| 2016/0157751 A1 | 6/2016 | Mahfouz |
| 2016/0157936 A1 | 6/2016 | Netravali |
| 2016/0175054 A1 | 6/2016 | Kang et al. |
| 2016/0191887 A1 | 6/2016 | Casas |
| 2016/0235381 A1 | 8/2016 | Scanlan et al. |
| 2016/0242931 A1 | 8/2016 | Wong et al. |
| 2016/0253846 A1 | 9/2016 | Scanlan et al. |
| 2016/0262772 A1 | 9/2016 | Gibson et al. |
| 2016/0278787 A1 | 9/2016 | Axelson, Jr. et al. |
| 2016/0278793 A1 | 9/2016 | Meridew et al. |
| 2016/0324580 A1 | 11/2016 | Esterberg |
| 2016/0331467 A1 | 11/2016 | Slamin et al. |
| 2017/0306416 A1 | 10/2017 | Bedoya et al. |
| 2018/0035964 A1 | 2/2018 | Funabasama et al. |
| 2018/0318014 A1 | 11/2018 | Gangwar et al. |
| 2019/0133693 A1 | 5/2019 | Mahfouz |
| 2019/0167221 A1 | 6/2019 | Simon et al. |
| 2019/0231433 A1 | 8/2019 | Amanatullah |
| 2019/0231434 A1 | 8/2019 | Lambers et al. |
| 2020/0253667 A1 | 8/2020 | Fouts et al. |
| 2020/0312011 A1 | 10/2020 | Kopeinigg et al. |
| 2021/0251590 A1 | 8/2021 | Guo |
| 2021/0259774 A1 | 8/2021 | Fouts et al. |
| 2022/0183760 A1 | 6/2022 | Fouts et al. |
| 2023/0210599 A1 | 7/2023 | Lambers et al. |
| 2024/0390017 A1 | 11/2024 | Fouts |

FOREIGN PATENT DOCUMENTS

| | | |
|---|---|---|
| CN | 104185451 A | 12/2014 |
| CN | 104244860 A | 12/2014 |
| CN | 112037200 A | 12/2020 |
| DE | 10057023 A1 | 6/2002 |
| EP | 1844726 B1 | 10/2007 |
| EP | 2618313 A1 | 7/2013 |
| WO | 2011/158117 A2 | 12/2011 |
| WO | 2012/149964 A1 | 11/2012 |
| WO | 2013/174401 A1 | 11/2013 |
| WO | 2013/174402 A1 | 11/2013 |
| WO | 2014/048447 A1 | 4/2014 |
| WO | 2015/124171 A1 | 8/2015 |
| WO | 2016/154557 A1 | 9/2016 |
| WO | 2017218933 A1 | 12/2017 |
| WO | 2018236936 A1 | 12/2018 |
| WO | 2019/148154 A1 | 8/2019 |

OTHER PUBLICATIONS

Alignment Disorders, Radiology Key, 2015, https://radiologykey.com/alignment-disorders/.

Allen, D. et al., Prevalence of associated deformities and hip pain in patients with cam-type femoroacetabular impingement, J Bone Joint Surg, vol. 91-B. No. 5, May 2009, pp. 589-594.

Anderson, Lucas A. et al., Acetabular Carilage Delamination in Femoroacetabular Impingement: Risk Factors and Magnetic Resonance Imaging Diagnosis, J Bone Joint Surg Am, vol. 91, No., 2009, pp. 305-313.

Atlas of MSK Measurements: how to draw the alpha angle, Stanford MSK, http://xrayhead.com/measure/show_measurement.php?i=3.

Atlas of MSK Measurements: how to draw the femoral version, Stanford MSK, http://xrayhead.com/measure/show_measurement.php?i=5.

Audenaert et al. (May 2012). "Imageless versus image-based registration in navigated arthroscopy of the hip," The Journal of Bone & Joint Surgery 94-B(5) 624-629.

Audenaert, Emmanuel A. et al., Development of a three-dimensional detection method of cam deformities in femoroacetabular impingement, Skeletal Radiology, vol. 40, 2011, pp. 921-927.

Audenaert, Emmanuel A. et al., Three-Dimensional Assessment of Cam Engagement in Femoroacetabular Impingement, Arthroscopy, vol. 27, No. 2, 2011, pp. 167-171.

Beaule, Paul E. et al., Three-dimensional computed tomography of the hip in the assessment of femoroacetabular impingement, J Orthop Res, vol. 23, 2005, pp. 1286-1292.

Beck, M. et al., Hip morphology influences the pattern of damage to the acetabular cartilage: femoroacetabular impingement as a cause of early osteoarthritis of the hip, J Bone Joint Surg, vol. 87-B, No. 7, 2005, pp. 1012-1018.

Bei, Yanhong. et al., Multibody dynamic simulation of knee contact mechanics, Med Eng Phys., vol. 26, No. 9, Nov. 2004, pp. 777-789.

Bouma, Heinse W. et al., Can Combining Femoral and Acetabular Morphology Parameters Improve the Characterization of Femoroacetabular Impingement?, Clin Orthop Rel Res, vol. 473, No. 4, 2015, pp. 1396-1403.

Broughton, N. S. et al., Reliability of radiological measurements in the assessment of the child's hip, J Bone Joint Surg, vol. 71-B, No. 1, 1989, p. 6-8.

Butler, Mark H., Current Technologies for Device Independence, Hewlett Packard, 2001, pp. 1-28.

Cadet, Edwin R. et al., Inter- and intra-observer agreement of femoroacetabular impingement (FAI) parameters comparing plain radiographs and advanced, 3D computed tomographic (CT)-generated hip models in a surgical patient cohort, Knee Surg Sports Traumatol Arthrosc, vol. 27, No. 7, 2014, pp. 2324-2331.

Carlisle, John C. et al., Reliability of Various Observers in Determining Common Radiographic Parameters of Adult Hip Structural Anatomy, The Iowa Orthopaedic Journal, vol. 31, 2011, pp. 52-58.

Chadayammuri, Vivek et al., Measurement of lateral acetabular coverage: a comparison between CT and plain radiography, J Hip Preservation Surgery, vol. 2, No. 4, Oct. 22, 2015, pp. 392-400.

Chadayammuri, Vivek et al., Passive Hip Range of Motion Predicts Femoral Torsion and Acetabular Version, J Bone Joint Surg Am., vol. 98, 2016, pp. 127-134.

Chavhan, Govind B. et al., Principles, Techniques, and Applications of T2*-based MR Imaging and Its Special Applications, RadioGraphics, vol. 29, 2009, pp. 1433-1449.

Cheng, Hui et al., Comparison of 2.5D and 3D Quantification of Femoral Head Coverage in Normal Control Subjects and Patients with Hip Dyplasia, PLOS One, vol. 10, No. 11, Nov. 24, 2015, pp. 1-14.

Clohisy, John C. et al., A Systematic Approach to the Plain Radiographic Evaluation of the Young Adult Hip, J Bone Joint Surg Am., vol. 90, Supp. 4, 2008, pp. 47-66.

Clohisy, John C. et al., Radiographic Evaluation of the Hip has Limited Reliability, Clin Orthop Relat Res, vol. 467, 2009, pp. 666-675.

Clohisy, John C. et al., The Frog-leg Lateral Radiograph Accurately Visualized Hip Cam Impingement Abnormalities, Clin Orthop Relat Res, No. 462, Sep. 2007, pp. 115-121.

Cobb et al. (Apr. 30, 2010). "Cams and Pincer Impingement Are Distinct, Not Mixed," Clinical Orthopaedics and Related Research 468(8): 2143-2151.

Dandachli, W. et al., Analysis of cover of the femoral head in normal and dysplastic hips, J Bone Joint Surg, vol. 90-B, No. 11, 2008, pp. 1428-1434.

Dandachli, W. et al., Three-dimensional CT analysis to determine acetabular retroversion and the implications for the management of femoro-acetabular impingement, J Bone Joint Surg. vol. 91-B, No. 8, 2009, pp. 1031-1036.

Danz, J.C. et al., Three-dimensional portable document format: A simple way to present 3-dimensional data in an electronic publication, American Journal of Orthodontics and Dentofacial Orthopedics, vol. 140, No. 2, Aug. 2011, pp. 274-276.

Decision of Rejection dated Sep. 1, 2022, directed to CN Application No. 201780083846.8; 14 pages.

(56) References Cited

OTHER PUBLICATIONS

Dyonics Plan Hip Impingement Planning System: User Manual and Frequently Asked Questions, Smith & Nephew, Inc., 2014.
Eguizabal, Alma et al., A Weighting Strategy for Active Shape Models, IEEE International Conference on Image Processing, 2017.
Eijer, H. et al., Evaluation and Treatment of Young Adults with Femoro-Acetabular Impingement Secondary to Perthes' Disease, Hip Int., vol. 16, No. 4, 2006, pp. 273-280.
EOS Imaging. "EOS System," located at https://www.eos-imaging.com/us/our-expertise/imaging-solutions/eos-system, visited on Oct. 29, 2019. 8 pages.
Extended European Search Report dated May 13, 2020, directed to EP Application No. 17870894.7; 12 pages.
Fa, Lianggluo et al., Superiority of the modified Tonnis angle over the Tonnis angle in the radiographic diagnosis of acetabuular dysplasia, Experimental and Therapeutic Medicine, vol. 8, 2014, pp. 1934-1938.
Fabricant, Peter D. et al., Clinical Outcomes After Arthroscopic Psoas Lengthening: The Effect of Femoral Version, Arthroscopy, vol. 28, No. 7, 2012, pp. 965-971.
Fabricant, Peter D. et al., The Effect of Femoral and Acetabular Version on Clinical Outcomes After Arthroscopic Femoroacetabular Impingement Surgery, J Bone Joint Surg, vol. 97, No. 7, 2015, pp. 537-543.
First Office Action dated Aug. 31, 2021, directed to CN Application No. 201780083846.8; 25 pages.
Fouts et al., U.S. Notice of Allowance and Fee(s) Due mailed Nov. 3, 2022, directed to U.S. Appl. No. 17/143,091; 9 pages.
Fouts et al., U.S. Notice of Allowance and Fee(s) Due mailed Oct. 8, 2020, directed to U.S. Appl. No. 15/818,394; 7 pages.
Fouts et al., U.S. Office Action dated Apr. 21, 2020, directed to U.S. Appl. No. 15/818,394; 33 pages.
Fouts et al., U.S. Office Action dated Dec. 20, 2019, directed to U.S. Appl. No. 15/818,394: 28 pages.
Fouts et al., U.S. Office Action dated Dec. 8, 2023, directed to U.S. Appl. No. 16/785,367; 39 pages.
Fouts et al., U.S. Office Action dated Feb. 15, 2019, directed to U.S. Appl. No. 15/818,394; 21 pages.
Fouts et al., U.S. Office Action dated Mar. 1, 2022, directed to U.S. Appl. No. 16/785,367; 31 pages.
Fouts et al., U.S. Office Action dated Mar. 23, 2023, directed to U.S. Appl. No. 16/785,367; 18 pages.
Fouts et al., U.S. Office Action dated Sep. 23, 2022, directed to U.S. Appl. No. 16/785,367; 21 pages.
Gosvig, K. K. et al., A new radiological index for assessing asphericity of the femoral head in cam impingement, J Bone Joint Surg, vol. 89-B, No. 10, Oct. 2007, pp. 1309-1316.
Hanson, Joey A. et al., Discrepancies in measuring acetabular coverage: revisiting the anterior and lateral center edge angels, Journal of Hip Preservation Surgery, vol. 2, No. 3, 2015, pp. 280-286.
Hellman, Michael D. et al., Radiographic Comparison of Anterior Acetabular Rim Morphology Between Pincer Femoroacetabular Impingement and Control, Arthroscopy, vol. 32, No. 3, 2016, pp. 468-472.
Hernandez, Ramiro J. et al., CT Determination of Femoral Torsion, AJR, vol. 137, Jul. 1981, pp. 97-101.
Hetsroni, Iftach et al., Anterior Inferior Illiac Spine Morphology Correlates With Hip Range of Motion: A Classification System and Dtynamic Model, Clin Orthop Relat Res, vol. 471, No. 8, Aug. 2013, pp. 2497-2503.
Heyworth, Benton E. et al., Preoperative Three-dimensional CT Predicts Intraoperative Findings in Hip Arthroscopy, Clin Orthop Rlat Res, vol. 470, No. 7, Jul. 2012, pp. 1950-1957.
International Preliminary Report on Patentability dated Aug. 23, 2022, directed to International Application No. PCT/US2021/018911; 10 pages.
International Preliminary Report on Patentability dated Jun. 13, 2023, directed to International Application No. PCT. US2021/072917; 9 pages.
International Preliminary Report on Patentability mailed on May 31, 2019 for PCT Application No. PCT/US2017/062603 filed Nov. 20, 2017, 11 pages.
International Search Report and Written Opinion mailed Jun. 1, 2021, directed to International Application No. PCT/US2021/018911; 17 pages.
International Search Report and Written Opinion mailed May 10, 2022, directed to International Application No. PCT/US2021/072917; 13 pages.
International Search Report and Written Opinion mailed on Feb. 1, 2018 for PCT Application No. PCT/US2017/062603 filed Nov. 20, 2017, 12 pages.
Ito, K. et al., Femoroacetabular impingement and the cam-effect: a MRI-based quantitative anatomical study of the femoral head-neck offset, J Bone Joint Surg, vol. 83-B, No. 2, Mar. 2001, pp. 171-176.
Jesse, Mary Kristen et al., Normal Anatomy and Imaging of the Hip: Emphasis on Impingement Assessment, Seminars in Musculoskeletal Radiology, vol. 17, No. 3, 2013, pp. 229-247.
Johnston, Todd L. et al., Relationship Between Offset Angle Alpha and Hip Chondral Injury in Femoroacetabular Impingement, Arthoroscopy, vol. 24, No. 6, 2008, pp. 669-675.
Kasten et al. (Apr. 2020). "End-To-End Convultional Neural Network for 3D Reconstruction of Knee Bones from Bi-Planar X-Ray Images," 12 pages.
Kelkar, Rajeev, Normal and Abnormal Mechanics of the Shoulder: Studies of Articular Geometry, Contact, and Kinematics, ProQuest Dissertations and Theses, 1996.
Kelly, Bryan T. et al., Alterations in Internal Rotation and Alpha Angles Are Associated With Arthroscopic Cam Decompression in the Hip, The American Journal of Sports Medicine, 2012, pp. 1-6.
Konishi, N. et al., Determination of acetabular coverage of the femoral head with use of a single anteroposterior radiograph. A new computerized technique, J Bone Joint Surg Am, vol. 75-A, No. 9, 1993, pp. 1318-1333.
Kraeutler, Matthew J. et al., Femoral Version Abnormalities Significantly Outweigh Effect of Cam Impingement on Hip Internal Rotation, J Bone Joint Surg Am., vol. 100-A, No. 3, 2018, pp. 205-210.
Krekel, P.R. et al., Interactive simulation and comparative visualisation of the bone-determined range of motion of the human shoulder, SimVis, 2006, pp. 1-13.
Laborie, Lene Bjerke et al., Radiographic measurements of hip dysplasia at skeletal maturity—new reference intervals baed on 2,036 19-yea-old Norwegians, Skeletal Radiol, vol. 42, No. 7, Jul. 2013, pp. 925-935.
Lambers et al., U.S. Advisory Action dated Oct. 21, 2021, directed to U.S. Appl. No. 16/261,464; 5 pages.
Lambers et al., U.S. Notice of Allowance and Fee(s) Due mailed May 13, 2022, directed to U.S. Appl. No. 16/261,464; 5 pages.
Lambers et al., U.S. Notice of Allowance and Fee(s) Due mailed Nov. 24, 2023, directed to U.S. Appl. No. 18/045,449; 6 pages.
Lambers et al., U.S. Office Action dated Dec. 15, 2020 directed U.S. Appl. No. 16/261,464; 16 pages.
Lambers et al., U.S. Office Action dated Dec. 20, 2021, directed to U.S. Appl. No. 16/261,464; 15 pages.
Lambers et al., U.S. Office Action dated Jul. 7, 2023, directed to U.S. Appl. No. 18/045,449; 14 pages.
Lambers et al., U.S. Office Action dated Jun. 11, 2021, directed to U.S. Appl. No. 16/261,464; 13 pages.
Larson, Christopher M. et al., Are Normal Hips Being Labeled as Pathologic? A CT-based Method for Defining Normal Acetabular Coverage, Clin Orthop Relat Res, vol. 473, No. 4, Apr. 5, 2015. pp. 1247-1254.
Larson, Christopher M. et al., Arthroscopic Hip Revision Surgery for Residual Femoroacetabular Impingement (FAI): Surgical Outcomes Compared With a Matched Cohort After Primary Arthroscopic FAI Correction, The Am J of Sports Med. vol. 42, No. 8, 2014, pp. 1785-1790.
Leboeuf, Fabien, Using LATEX to produce multi-media clinical reports, The PracTeX Journal, No. 1, 2011, pp. 1-14.
Lequesne, M. et al., The normal hip joint space: variations in width, shape, and architecture on 223 pelvic radiographs, Ann Rheum Dis, vol. 63, 2004, pp. 1145-1151.

(56) References Cited

OTHER PUBLICATIONS

Levy, David M. et al., Prevalence of Cam Morphology in Females with Femoroacetabular Impingement, Front. Surg., vol. 2, No. 61, Dec. 2015, pp. 1-5.
Linder et al. (Aug. 2013). "Fully Automatic Segmentation of the Proximal Femur Using Random Forest Regression Voting," IEEE Transactions on Medical Imaging 32(8):1462-1472.
Mardones, Rodrigo M. et al., Surgical Correction of "Cam-Type" Femoroacetabular Impingement: A Cadaveric Comparison of Open Versus Arthroscopic Debridement, Arthroscopy, vol. 25, No. 2, 2009, pp. 175-182.
Mardones, Rodrigo M. et al., Surgical Treatment of Femoroacetabular Impingement: Evaluation of the Effect of the Size of the Resection, J Bone Joint Surg Am, vol. 88A, Supp. 1, Mar. 2006, pp. 84-91.
Matsuda et al., Acute Iatrogenic Dislocation Following Hip Impingement Arthroscopic Surgery, Arthroscopy, vol. 25, No. 4, 2009, pp. 400-404.
Matsuda et al., Closed Intramedullary Derotational Osteotomy and Hip Arthroscopy for Cam Femoroacetabular Impingement From Femoral Retroversion, Arthroscopy Techniques, vol. 3, No. 1, 2014, pp. e83-e88.
McCarthy, Joseph et al., Anatomy, pathologic features, and treatment of acetabular labral tears, Clin Orthop Relat Res, No. 406, 2003, pp. 38-47.
Meyer, Dominik C. et al., Comparison of Six Radiographic Projections to Assess Femoral Head/Neck Ashpericity, Clin Orthop Relat Res. No. 445, 2006, pp. 181-185.
Milone, Michael T. et al., Novel CT-based Three-dimensional Software Improves the Characterization of Cam Morphology, Clin Orthop Relat Res, vol. 471, No. 8, Aug. 2013, pp. 2484-2491.
Minciullo et al. "Fully Automated Shape Analysis for Detection of Osteoarthritis from Lateral Knee Radiographs," 2016 23rd International Conference on Pattern Recognition (ICPR), Dec. 4-8, 2016, Cancún Center, Cancún, México; pp. 3787-3791.
Miyasaka, Dai et al., Three-dimensional Assessment of Femoral Head Coverage in Normal and Dysplastic Hips: A Novel Method, Acta Med., vol. 68, No. 5, 2014, pp. 277-284.
Murphy, S.B. et al., The prognosis in untreated dysplasia of the hip: A study of radiographic factors that predict the outcome, J Bone Joint Surg Am, vol. 77-A, No. 7, 1995, pp. 985-989.
Nepple, Jeffrey J. et al., Clinical and Radiographic Predictors of Intra-articular Hip Disease in Arthroscopy, Am J Sports Med, vol. 39, No. 2, 2011, pp. 296-303.
Nepple, Jeffrey J. et al., Diagnostic Imaging of Femoroacetabular Impingement, J Am Acad Orthop Surg, vol. 21, Suppl. 1, 2013, pp. S20-S26.
Nepple, Jeffrey J. et al., Do Plain Radiographs Correlate With CT for Imaging of Cam-type Femoroacetabular Impingement ?. Clin Orthop Relat Res, vol. 470, No. 12, Dec. 2012, pp. 3313-3320.
Notzli, H.P. et al., The contour of the femoral head-neck junction as a predictor for the risk of anterior impingement, J Bone Joint Surg, vol. 84-B, 2002, pp. 556-560.
Office Action dated Aug. 23, 2023, directed to EP Application No. 17 870 894.7; 6 pages.
Ogata, S. et al., Acetabular cover in congenital dislocation of the hip, J Bone Joint Surg, vol. 72-B, No. 2, 1990, pp. 190-196.
Omeroglu, Hakan et al., Analysis of a radiographic assessment method of acetabular cover in developmental dysplasia of the hip, Arch Orthop Trauma Surg, vol. 122, No. 6, 2002, pp. 334-337.
Omeroglu, Hakan et al., Measurement of center-edge angle in developmental dysplasia of the hip: a comparison of two methods in patients under 20 years of age, Skeletal Radiol, vol. 31, No. 1, 2002, pp. 25-29.
Outerbridge, R.E., The etiology of chondromalacia patellae, J Bone Joint Surg, vol. 43-B, No. 4, 1961, pp. 556-560.
Ozcelik, Abdurrahman et al., Definition of a quantitative measurement method for acetabular version in a plain radiograph in the healthy adult hip, Eklem Hastalik Cerrahisi, vol. 26, No. 1, 2015, pp. 2-5.

Panoramic Fluoro, Radlink Inc., 2017, http:--www.radlink.com-index.php-products-software-surgeons-checklist-software-panoramic-fluoro-.
Perreira, Aimee C. et al., Multilevel Measurement of Acetabular Version Using 3-D CT-generated Models, Clin Orthop Relat Res, vol. 469, No. 2, Feb. 2011, pp. 552-561.
Phelps, A. et al., Embedding 3D Radiology Models in Portable Document Format, American Journal of Roentgenology, vol. 199, No. 6, Dec. 2012, pp. 1342-1344.
Rakhra, Kawan S. et al., Comparison of MRI Alpha Angle Measurement Planes in Femoroacetabular Impingement, Clin Orthop Relat Res, vol. 467, No. 3, 2009, pp. 660-665.
Reikeras, Olav et al., Cross table lateral radiography for measurement of acetabular cup version, Ann Transl Med., vol. 4, No. 9, 2016, pp. 1-4.
Reynolds, D. et al., Retroversion of the acetabulum: a cause of hip pain, J Bone Joint Surg, vol. 81-B, No. 2, Mar. 1999, pp. 281-288.
Ross, James R. et al., Intraoperative Fluoroscopic Imaging to Treat Cam Deformities: Correlation With 3-Dimensional Computed Tomography, Am J. Sports Med. Vol. 42, No. 6, 2014, pp. 1370-1376.
Ruthensteiner, B. et al., Embedding 3D Models of Biological Specimens in PDF Publications, Microscopy Research and Technique, vol. 71, No. 11, 2008, pp. 778-786.
Schumann et al. (2013). "An Integrated System for 3D Hip Joint Reconstruction from 2D X-rays: A Preliminary Validation Study," Annals of Biomedical Engineering, 41(10): 2077-2087.
Second Office Action dated Mar. 16, 2022, directed to CN Application No. 201780083846.8; 17 pages.
Siebenrock, K.A. et al., Effect of Pelvic Tilt on Acetabular Retroversion: A Study of Pelves From Cadavers, Clin Orthop Relat Res. No. 407, Feb. 2003, pp. 241-248.
Stahelin, Lisca et al., Arthroscopic Offset Restoration in Femoroacetabular Cam Impingement: Accuracy and Early Clinical Outcome, Arthroscopy: The J of the Arthroscopic and Rel Surg, vol. 24, No. 1, 2008, pp. 51-57.
Stelzeneder, David et al., Can Radiographic Morphometric Parameters for the Hip Be Assessed on MRI?, Clin Orthop Relat Res, vol. 471, No. 3, Mar. 2013, pp. 989-999.
Stubbs, Allston J. et al., Classic measures of hip dysplasia do not correlate with three-dimensional computer tomographic measures and indices, Hip Int, vol. 21, No. 5, 2011, pp. 549-558.
Tannast, Moritz et al., Conventional radiographs to assess femoroacetabular impingement, Instr Course Lect, vol. 58, 2009, pp. 203-212.
Tannast, Moritz et al., Femoroacetabular Impingement: Radiographic Diagnosis—What the Radiologist Should Know, Am J Radiology, vol. 188, Jun. 2007, pp. 1540-1552.
Tannast, Moritz et al., Noninvasive Three-Dimensional Assessment of Femoroacetabular Impingement, J Orthop Res, vol. 25, No. 1, 2007, pp. 122-131.
Tannast, Moritz et al., Which Radiographic Hip Parameters Do Not Have to Be Corrected for Pelvic Rotation and Tilt?, Clin Orthop Relat Res, vol. 473, No. 4, Apr. 2015, pp. 1255-1266.
Tannenbaum, Eric et al., Gender and racial differences in focal and global acetabular version, J Arthroplasty, vol. 29, No. 2, Feb. 2014, pp. 373-376.
Tannenbaum, Eric P. et al., A Computed Tomography Study of Gender Differences in Acetabular Version and Morphology: Implications for Femoroacetabular Impingement, The J of Arthroscopic and Rel Surg, vol. 31, No. 7, 2015, pp. 1247-1254.
Thaler et al. "Volumetric Reconstruction from a Limited Number of Digitally Reconstructed Radiographs Using CNNs," Proceedings of a OAGM Workshop, 2018; pp. 13-19.
Tonnis, D. et al., Acetabular and Femoral Anteversion: Relationship with Osteoarthritis of the Hip, J Bone Joint Surg Am, vol. 81-A, No. 12, 1999, pp. 1747-1770.
Tonnis, D., Congenital Dysplasia and Dislocation of the Hip in Children and Adults, Chapter 9, 1987, pp. 100-142.
Uchida, Soshi et al., Clinical and Radiographic Predicators for Worsened Clinical Outcomes After Hip Arthroscopic Labral Preservation and Capsular Closure in Developmental Dysplasia of the Hip, Am J Sports Med. vol. 44, No. 1, 2016, pp. 28-38.

(56) References Cited

OTHER PUBLICATIONS

Van Bosse, Harold J. P. et al., Pelvic Positioning Creates Error in CT Acetabular Measurements, Clin Orthop Relat Res, vol. 469, No. 6, Jun. 2011, pp. 1683-1691.
Werner, Clement M. L. et al., Normal values of Wiberg's lateral center-edge angle and Lequesne's acetabular index—a coxometric update, Skeletal Radiol, vol. 41, 2012, pp. 1273-1278.
Wiberg, Gunnar, Studies on Dysplastic Acetabula and Congenital Subluxation of the Hip Joint with Special Reference to the Complication of Osteoarthritis, Orthopedic Clinic of Karolinska Institutet, 1939, pp. 1-39 and 129-135.
Wilson, J. D. et al., To what degree is digital imaging reliable? Validation of femoral neck shaft angle measurement in the era of picture archiving and communication systems, The British Journal of Radiology, vol. 84, Apr. 2011, pp. 375-379.
Zaltz, Ira et al., The Crossover Sign Overestimates Acetabular Retroversion, Clin Orthop Relat Res, vol. 471, 2013, pp. 2463-2470.
Zhao et al. "Automated Analysis of Femoral Artery Calcification Using Machine Learning Techniques," 2019 International Conference on Computational Science and Computational Intelligence (CSCI), Dec. 5-7, 2019, Las Vegas, Nevada, United States; pp. 584-589.
Ziegler, A. et al., Effectively incorporating selected multimedia content into medical publications, BMC Medicine, vol. 9, No. 17, 2011, pp. 1-6.
Fouts et al., U.S. Election of Species Requirement dated Jun. 4, 2024, directed to U.S. Appl. No. 17/180,573; 6 pages.
Fouts et al., U.S. Office Action dated Jun. 3, 2024, directed to U.S. Appl. No. 16/785,367; 43 pages.
Fouts et al., U.S. Office Action dated Jun. 6, 2024, directed to U.S. Appl. No. 17/644,335; 14 pages.
Fouts et al., U.S. Advisory Action dated Oct. 18, 2024, directed to U.S. Appl. No. 16/785,367; 5 pages.
Fouts et al., U.S. Notice of Allowance and Fee(s) Due mailed Nov. 25, 2024, directed to U.S. Appl. No. 17/644,335; 10 pages.
Fouts et al., U.S. Office Action dated Nov. 1, 2024, directed to U.S. Appl. No. 17/180,573; 17 pages.
Jansen, Mylène. (Sep. 15, 2017). "A Novel 3D joint space quantification method in patients with osteoarthritis in the knee." 64 pages.
Fouts et al., U.S. Office Action dated Jan. 23, 2025, directed to U.S. Appl. No. 16/785,367; 34 pages.

\* cited by examiner

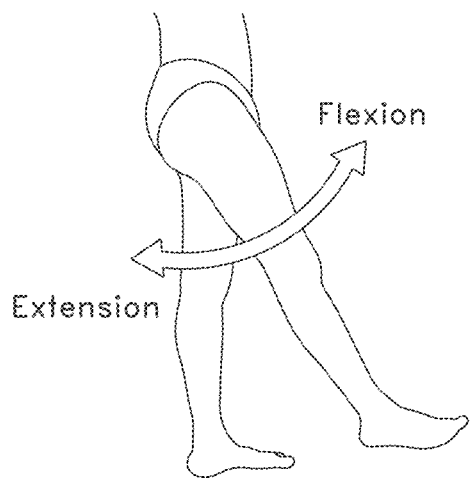
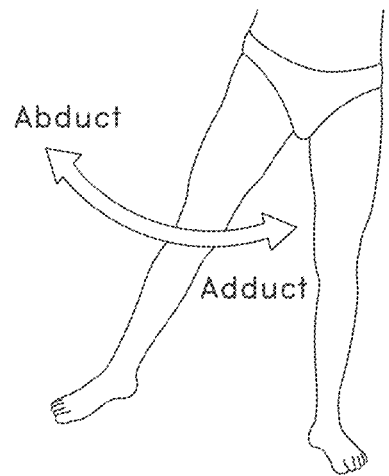
FIG. 1A  FIG. 1B
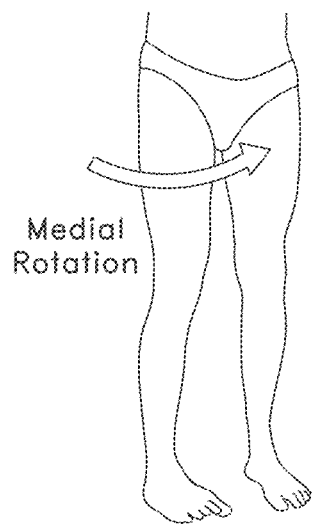
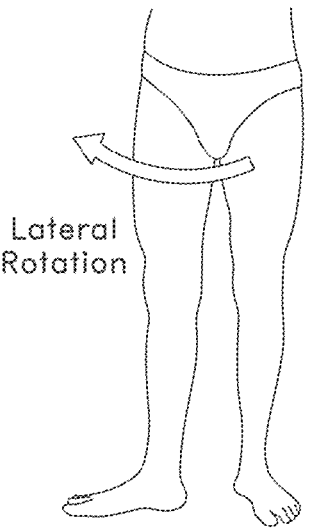
FIG. 1C  FIG. 1D

CAM-TYPE FEMOROACETABULAR IMPINGEMENT (FAI)

CAM INJURY TO THE LABRUM

PINCER-TYPE FEMOROACETABULAR IMPINGEMENT (FAI)

PINCER INJURY TO THE LABRUM

130

165  170

METHOD AND APPARATUS FOR TREATING A JOINT, INCLUDING THE TREATMENT OF CAM-TYPE FEMOROACETABULAR IMPINGEMENT IN A HIP JOINT AND PINCER-TYPE FEMOROACETABULAR IMPINGEMENT IN A HIP JOINT

CROSS-REFERENCE TO RELATED APPLICATIONS

This application is a continuation of U.S. patent application Ser. No. 17/143,091, filed Jan. 6, 2021, which is a continuation of U.S. patent application Ser. No. 15/818,394, filed Nov. 20, 2017, now U.S. Pat. No. 10,918,398, which claims the benefit of U.S. Provisional Application No. 62/423,890, filed Nov. 18, 2016, each of which are hereby incorporated by reference in their entireties.

FIELD OF THE INVENTION

This invention relates to surgical methods and apparatus in general, and more particularly to surgical methods and apparatus for treating a hip joint.

BACKGROUND OF THE INVENTION

The hip joint movably connects the leg to the torso. The hip joint is a ball-and-socket joint, and is capable of a wide range of different motions, e.g., flexion and extension, abduction and adduction, internal and external rotation, etc. See FIGS. 1A-1D. With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases an existing pathology may be exacerbated by the dynamic nature of the hip joint and the substantial weight loads imposed on the hip joint.

The pathology may, either initially or thereafter, significantly interfere with patient comfort and lifestyle. In some cases the pathology may be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more precise understanding of the anatomy of the hip joint.

Anatomy of the Hip Joint

The hip joint is formed at the junction of the femur and the hip. More particularly, and looking now at FIG. 2, the ball of the femur is received in the acetabular cup of the hip, with a plurality of ligaments and other soft tissue serving to hold the bones in articulating condition.

As seen in FIG. 3, the femur is generally characterized by an elongated body terminating, at its top end, in an angled neck which supports a hemispherical head (also sometimes referred to as the ball). As seen in FIGS. 3 and 4, a large projection known as the greater trochanter protrudes laterally and posteriorly from the elongated body adjacent to the neck. A second, somewhat smaller projection known as the lesser trochanter protrudes medially and posteriorly from the elongated body adjacent to the neck. An intertrochanteric crest extends along the periphery of the femur, between the greater trochanter and the lesser trochanter.

Looking next at FIG. 5, the hip is made up of three constituent bones: the ilium, the ischium and the pubis. These three bones cooperate with one another (they typically ossify into a single "hip bone" structure by the age of 25) so as to form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIG. 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition, and looking now at FIG. 10, a fibrous capsule extends between the neck of the femur and the rim of the acetabular cup, effectively sealing off the ball-and-socket members of the hip joint from the remainder of the body. The foregoing structures are encompassed and reinforced by a set of three main ligaments (i.e., the iliofemoral ligament, the ischiofemoral ligament and the pubofemoral ligament) which extend between the femur and the hip. See FIGS. 11 and 12.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as a cam-type femoroacetabular impingement (i.e., a cam-type FAI). In other cases, and looking now at FIG. 14, the impingement can occur due to irregularities in the geometry of the acetabular cup. This latter type of impingement is sometimes referred to as a pincer-type femoroacetabular impingement (i.e., a pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce or exacerbate arthritic conditions and, in some cases, cause significant deterioration of the hip joint.

By way of further example but not limitation, one important type of injury-related pathology of the hip joint involves trauma to the labrum. More particularly, in many cases, an accident or a sports-related injury can result in the labrum being torn, typically with a tear running through the body of the labrum. See FIG. 15. These types of injuries can be painful for the patient and, if left untreated, can lead to substantial deterioration of the hip joint.

The General Trend Toward Treating Joint Pathologies Using Minimally-Invasive, And Earlier, Interventions The current trend in orthopedic surgery is to treat joint pathologies using minimally-invasive techniques. By way of example but not limitation, it is common to re-attach ligaments in the shoulder joint using minimally-invasive, "keyhole" techniques which do not require "laying open" the capsule of the shoulder joint. By way of further example but not limitation, it is common to repair torn meniscal cartilage in the knee joint, and/or to replace ruptured ACL ligaments in the knee joint, using minimally-invasive techniques. While such minimally-invasive approaches can require additional training on the part of the surgeon, such procedures generally offer substantial advantages for the patient and have now become the standard of care for many shoulder joint and knee joint pathologies.

In addition to the foregoing, due to the widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged behind minimally-invasive treatments for pathologies of the shoulder joint and knee joint. This is generally due to (i) the geometry of the hip joint itself, and (ii) the nature of the pathologies which must typically be addressed in the hip joint.

More particularly, the hip joint is generally considered to be a "tight" joint, in the sense that there is relatively little room to maneuver within the confines of the joint itself. This is in marked contrast to the knee joint, which is generally considered to be relatively spacious when compared to the hip joint. As a result, it is relatively difficult for surgeons to perform minimally-invasive procedures on the hip joint.

Furthermore, the natural pathways for entering the interior of the hip joint (i.e., the pathways which naturally exist between adjacent bones) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures. By way of example but not limitation, consider a typical tear of the labrum in the hip joint. In this situation, instruments must generally be introduced into the joint space using a line of approach which is set, in some locations, at an angle of 25 degrees or more to the line of repair. This makes drilling into bone, for example, much more complex than where the line of approach is effectively aligned with the line of repair, such as is frequently the case in the shoulder joint. Furthermore, the working space within the hip joint is typically extremely limited, further complicating repairs where the line of approach is not aligned with the line of repair.

As a result of the foregoing, minimally-invasive hip joint procedures are still relatively difficult, and patients must frequently manage their hip joint pathologies for as long as possible, until a partial or total hip replacement can no longer be avoided, whereupon the procedure is generally done as a highly-invasive, open procedure, with all of the disadvantages associated with highly-invasive, open procedures.

As a result, there is a pressing need for improved methods and apparatus for repairing the hip joint.

Issues Relating To The Treatment Of Cam-Type Femoroacetabular Impingement

As noted above, hip arthroscopy is becoming increasingly more common in the diagnosis and treatment of various hip pathologies. However, due to the anatomy of the hip joint and the pathologies associated with the same, hip arthroscopy is currently practical for only selected pathologies and, even then, hip arthroscopy has generally met with limited success.

One procedure which is sometimes attempted arthroscopically relates to femoral debridement for treatment of cam-type femoroacetabular impingement (i.e., cam-type FAI). More particularly, with cam-type femoroacetabular impingement, irregularities in the geometry of the femur can lead to impingement between the femur and the rim of the acetabular cup. Treatment for cam-type femoroacetabular impingement typically involves debriding the femoral neck and/or head, using instruments such as burrs and osteotomes, to remove the bony deformities causing the impingement. In this respect it should be appreciated that it is important to debride the femur carefully, since only bone which does not conform to the desired geometry should be removed, in order to ensure positive results as well as to minimize the possibility of bone fracture after treatment.

For this reason, when debridement is performed as an open surgical procedure, surgeons generally use debridement templates having a pre-shaped curvature to guide them in removing the appropriate amount of bone from the femur.

However, when the debridement procedure is attempted arthroscopically, conventional debridement templates with their pre-shaped curvature cannot be passed through the narrow keyhole incisions, and hence debridement templates are generally not available to guide the surgeon in reshaping the bone surface. As a result, the debridement must generally be effected "freehand." In addition to the foregoing, the view of the cam pathology is also generally limited. Primarily, the surgeon uses a scope and camera to view the resection area, but the scope image has a limited field of view and is somewhat distorted. Also, because the scope is placed close to the bone surface, the surgeon cannot view the entire pathology "all at once." Secondarily, the surgeon also utilizes a fluoroscope to take X-ray images of the anatomy. These X-ray images supplement the arthroscopic view from the scope, but it is still limited to a 2D representation of the 3D cam pathology.

As a result of the foregoing, it is generally quite difficult for the surgeon to determine exactly how much bone should be removed, and whether the shape of the remaining bone has the desired geometry. In practice, surgeons tend to err on the side of caution and remove less bone. Significantly, under-resection of the cam pathology is the leading cause of revision hip arthroscopy.

Accordingly, a primary object of the present invention is to provide the surgeon with a novel method and apparatus for guiding the surgeon during an arthroscopic debridement procedure to treat cam-type femoroacetabular impingement.

Issues Relating to the Treatment of Pincer-Type Femoroacetabular Impingement

Another procedure which is sometimes attempted arthroscopically relates to treatment of pincer-type femoroacetabular impingement (i.e., pincer-type FAI). More particularly, with pincer-type femoroacetabular impingement, irregularities in the geometry of the acetabulum can lead to impingement between the femur and the rim of the acetabular cup. Treatment for pincer-type femoroacetabular impingement typically involves debriding the rim of the acetabular cup using instruments such as burrs and osteotomes to remove the bony deformities causing the impingement. In some cases, the labrum is released from the acetabular bone so as to expose the underlying rim of the acetabular cup prior to debriding the rim of the acetabular cup, and then the labrum is reattached to the debrided rim of the acetabular cup. In this respect it should be appreciated that it is important to debride the rim of the acetabular cup carefully, since only bone which does not conform to the desired geometry should be removed, in order to alleviate impingement while minimizing the possibility of removing too much bone from the rim of the acetabular cup, which could cause joint instability.

However, when the debridement procedure is attempted arthroscopically, the debridement must generally be effected freehand. In this setting, it is generally quite difficult for the surgeon to determine exactly how much bone should be removed, and whether the remaining bone has the desired geometry. In practice, surgeons tend to err on the side of caution and remove less bone. Significantly, under-resection of the pincer pathology may necessitate revision hip arthroscopy.

Accordingly, another object of the present invention is to provide the surgeon with a novel method and apparatus for guiding the surgeon during an arthroscopic debridement procedure to treat pincer-type femoroacetabular impingement.

Alpha Angle and Center Edge Angle Measurements

Two common anatomical measurements used in diagnosing femoroacetabular impingement (FAI) are the Alpha Angle (FIG. 16) for cam-type impingement and the Center Edge Angle (FIG. 17) for pincer-type impingement. These measurements are typically measured from pre-operative images (e.g., pre-operative X-ray images). These measurements are used to determine the degree to which the patient's hip anatomy deviates from normal, healthy hip anatomy.

For example, a healthy hip typically has an Alpha Angle of anywhere from less than approximately 42 degrees to approximately 50 degrees; thus, a patient with an Alpha Angle of greater than approximately 42 degrees to approximately 50 degrees may be a candidate for FAI surgery. During an initial examination of a patient, the surgeon will typically take an X-ray of the patient's hip. If the patient has an initial diagnosis of FAI, the patient may also obtain an MRI or CT scan of their hip for further evaluation of the bony pathology causing the FAI.

Most of today's imaging techniques (e.g., X-ray, CT, MRI) are digital, and hence the images can be imported into, and manipulated by, computer software. Using the imported digital images, the surgeon is able to measure the Alpha Angle (and/or the Center Edge Angle). For example, the surgeon imports the digital image into one of the many available software programs that use the DICOM (Digital Imaging and Communications in Medicine) standard for medical imaging. In order to make the Alpha Angle (or the Center Edge Angle) measurements with the digital image, the surgeon must first manually create and overlay geometric shapes onto the digital medical image.

For example, and looking now at FIG. 16, to measure the Alpha Angle, the surgeon manually creates a circle 5 and places it over the femoral head 10, and then manually sizes the circle such that the edge of the circle matches the edge of the femoral head. The surgeon then manually creates a line 15 and places it along the mid-line of the femoral neck 20. The surgeon then manually draws a second line 25 which originates at the center of the femoral head and passes through the location which signifies the start of the cam pathology 30 (i.e., the location where the bone first extends outside the circle set around the femoral head). The surgeon then manually selects the two lines and instructs the software to calculate the angle between the two lines; the result is the Alpha Angle 35.

Correspondingly, and looking now at FIG. 17, to measure the Center Edge Angle, the surgeon manually creates a vertical line 40 which originates at the center of the femoral head, and then manually draws a second line 45 which originates at the center of the femoral head and passes through the location which signifies the start of the pincer pathology 50 (i.e., the rim of the acetabular cup). The surgeon then manually selects the two lines and instructs the software to calculate the angle between the two lines; the result is the Center Edge Angle 55.

With 3D medical images (e.g., CT, MRI, etc.), the surgeon can position one or more planes through the femoral head, and then performs the same operations within the one or more planes to measure the Alpha Angle for a given plane.

These Alpha Angle measurements (or Center Edge Angle measurements) are typically performed around the time that the patient is initially examined, which typically occurs weeks or months prior to surgery.

At the time of surgery, the surgeon may bring a copy (e.g., a printout) of the Alpha Angle measurements (or the Center Edge Angle measurements) to the operating room so that the printout is available as a reference during surgery. The surgeon may also have access to these measurements with a computer located in or near the operating room, which is connected to the hospital's PACS system (Picture Archiving and Communication System). Either way, the surgeon can have the pre-operative measurements available as a reference during surgery.

However, while the surgeon is debriding bone on the cam (or pincer), the surgeon cannot get an updated measurement of the Alpha Angle (or the Center Edge Angle) to determine if more bone needs to be removed. In order to achieve this, the patient would have to be moved out of the operating room to the imaging room, the necessary image(s) obtained, the measurements (Alpha Angle or Center Edge Angle) calculated, and then the patient moved back to the operating room. The time necessary to do this, while requiring the operating room staff to wait, in addition to the inability to maintain sterility of the patient's surgical site, make this an impractical solution. As a result, the surgeon lacks the ability to measure the Alpha Angle (and/or the Center Edge Angle) during surgery. Therefore, the surgeon cannot make these anatomical measurements while bone is being removed to assess if sufficient bone has been removed or if additional bone removal is required. The surgery is completed without updated anatomical measurements to confirm that the cam (and/or pincer) pathologies have been adequately treated.

Accordingly, another object of the present invention is to provide the surgeon with a novel method and apparatus to take images at multiple time points during a surgery, measure the anatomy using the images, and then continue the surgery, all without disrupting the surgical procedure.

SUMMARY OF THE INVENTION

The present invention comprises a novel method and apparatus for treating a joint.

In one preferred form of the invention, there is provided a novel method and apparatus for guiding the surgeon during an arthroscopic debridement procedure to treat cam-type femoroacetabular impingement. In one preferred form of the invention, there is provided a novel computer visual guidance system wherein a 2D image obtained from an ordinary C-arm X-ray device is automatically analyzed and annotated so as to provide the surgeon with additional information for guiding the surgeon through an arthroscopic debridement procedure to treat cam-type femoroacetabular impingement. In one particularly preferred form of the invention, the surgeon lines up the C-arm X-ray device with the patient's hip, captures an X-ray image of the hip (femur and acetabulum), and the computer visual guidance system then automatically detects the edges of the femur and acetabulum, and computes and displays measurements of the cam pathology. The computer visual guidance system may additionally identify the cam pathology which is to be removed, and then annotate the C-arm image so as to show the surgeon the bone which is to be removed.

The surgeon preferably utilizes this tool iteratively during the resection until the cam pathology is completely removed, thereby ensuring that the appropriate bone is resected. This iterative approach can be repeated with the patient's leg in multiple positions so that the 2D projection of the cam pathology is visible under a variety of fluoroscopic visualizations.

In one form of the invention, automatic Alpha Angle measurement is performed and an Alpha Angle diagram is displayed. The advantage of utilizing the Alpha Angle measurement is that it is already commonly used to diagnose patients with cam-type impingement. However, Alpha Angle measurements have practical limitations. The Alpha Angle describes where the femoral head stops being round, but it does not define how far a resection should go around the head (e.g., further medial or lateral or posterior), nor does it define how far distally down the neck that resection should be smoothed and extended.

Further embodiments of the invention address these limitations. First, a second line is drawn for the Alpha Angle, with the second line designating the target Alpha Angle (in addition to the currently-measured Alpha Angle). The area outside the femoral head circle and between the currently-measured Alpha Angle line and the target Alpha Angle line describes the initial cam pathology which is to be removed, which is roughly triangular. Furthermore, a smooth transition is preferably provided between the bone resection and the remaining bone. This process is then preferably repeated by either re-positioning the patient's leg or moving the C-arm so as to obtain additional projections. It will be appreciated that obtaining a plurality of projections allows the surgeon to approximate the total 3D resection.

In another preferred form of the present invention, there is provided a novel method and apparatus for guiding the surgeon during an arthroscopic debridement procedure to treat pincer-type femoroacetabular impingement. In one preferred form of the invention, there is provided a novel computer visual guidance system wherein a 2D image obtained from an ordinary C-arm X-ray device is analyzed and annotated so as to provide the surgeon with additional information for guiding the surgeon through an arthroscopic debridement procedure to treat pincer-type femoroacetabular impingement. In one particularly preferred form of the invention, the surgeon lines up the C-arm X-ray device with the patient's hip, captures an X-ray image of the hip (femur and acetabulum), and then the computer visual guidance system automatically detects the edges of the femur and acetabulum, and then computes and displays measurements of the pincer pathology. The computer visual guidance system may additionally identify the pincer pathology which is to be removed, and then annotate the C-arm image so as to show the surgeon the bone which is to be removed.

In one form of the invention, an automatic Center Edge Angle measurement is performed and a Center Edge Angle diagram is displayed. Due to the fact that the Center Edge Angle requires proper vertical orientation of the pelvis, additional anatomy must be present in the X-ray image. The system can either utilize the contralateral femoral head to establish the horizontal plane for the Center Edge Angle measurement, or the system can use the pubic synthesis to establish the vertical plane for the Center Edge Angle measurement (however, this latter approach is typically less preferred since it is generally less accurate).

Similar to the Alpha Angle measurement, a simple measurement of the Center Edge Angle has its limitations. More particularly, a simple measurement of the Center Edge Angle does not define how far a resection should go, nor does it describe how the resection should be smoothed and extended. Therefore, in further embodiments of the invention, a target line and resection smoothing may be provided. Furthermore, an iterative approach to both resection and orientation are desirable to ensure a precise resection.

It should be appreciated that annotating X-ray images is not, in itself, novel. Alpha Angle, Center Edge Angle and other resection measurements and annotations are routinely conducted pre-operatively. However, these measurements and annotations are done manually by the surgeon or by the radiologist. And, significantly, these resection measurements and annotations are done pre-operatively—once a surgeon has scrubbed into surgery and the patient is under anesthesia, time is limited and the surgeon is busy manipulating the arthroscope and the resection instruments. Prior to the present invention, surgeons were not able to take resection measurements and have annotations on the X-ray images in real time during surgery. The computer visual guidance system of the present invention makes assisted surgery quick, accurate and hands-free.

In one form of the invention, there is provided a computer visual guidance system for guiding a surgeon through an arthroscopic debridement of a bony pathology, wherein the computer visual guidance system is configured to:
 (i) receive a 2D image of the bony pathology from a source;
 (ii) automatically analyze the 2D image so as to determine at least one measurement with respect to the bony pathology;
 (iii) automatically annotate the 2D image with at least one annotation relating to the at least one measurement determined with respect to the bony pathology so as to create an annotated 2D image; and
 (iv) display the annotated 2D image to the surgeon so as to guide the surgeon through the arthroscopic debridement of the bony pathology.

In another form of the invention, there is provided a method for guiding a surgeon through an arthroscopic debridement of a bony pathology, wherein the method comprises:

providing a computer visual guidance system, wherein the computer visual guidance system is configured to:
(i) receive a 2D image of the bony pathology from a source;
(ii) automatically analyze the 2D image so as to determine at least one measurement with respect to the bony pathology;
(iii) automatically annotate the 2D image with at least one annotation relating to the at least one measurement determined with respect to the bony pathology so as to create an annotated 2D image; and
(iv) display the annotated 2D image to the surgeon so as to guide the surgeon through the arthroscopic debridement of the bony pathology;

providing a 2D image of the bony pathology to the computer visual guidance system; and displaying the annotated 2D image to the surgeon.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 1A-1D are schematic views showing various aspects of hip motion;

DETAILED DESCRIPTION OF THE PREFERRED EMBODIMENTS

The present invention comprises a novel method and apparatus for treating a joint.

In one preferred form of the invention, there is provided a novel method and apparatus for guiding the surgeon during an arthroscopic debridement procedure to treat cam-type femoroacetabular impingement.

In another preferred form of the invention, there is provided a novel method and apparatus for guiding the surgeon during an arthroscopic debridement procedure to treat pincer-type femoroacetabular impingement.

Figure 2:
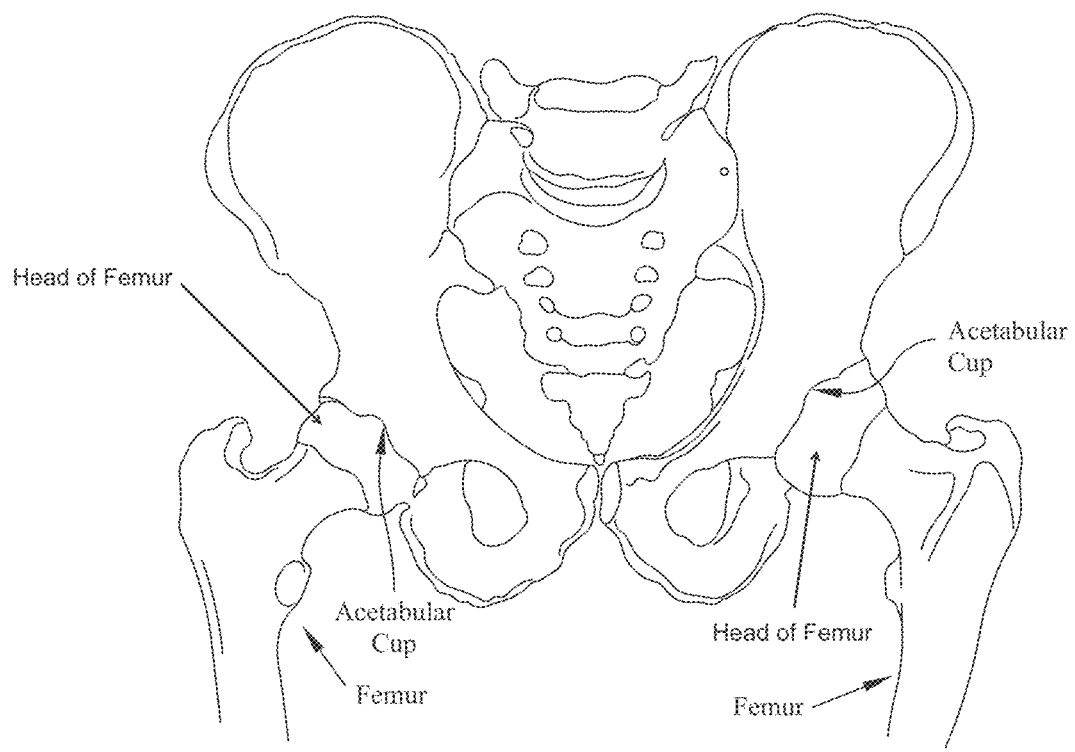
FIG. 2 is a schematic view showing bone structures in the region of the hip joint.
Figure 3:
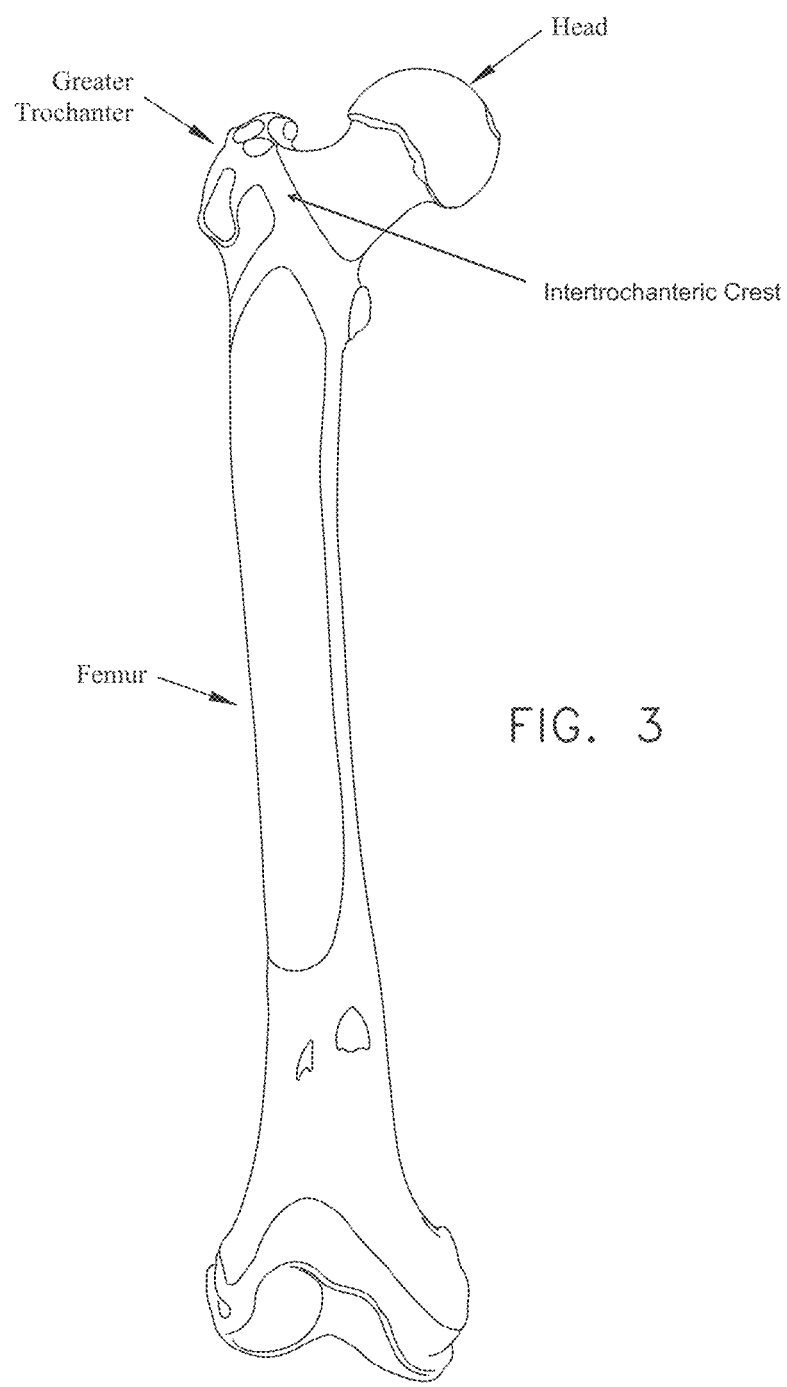
FIG. 3 is a schematic anterior view of the femur.
Figure 4:
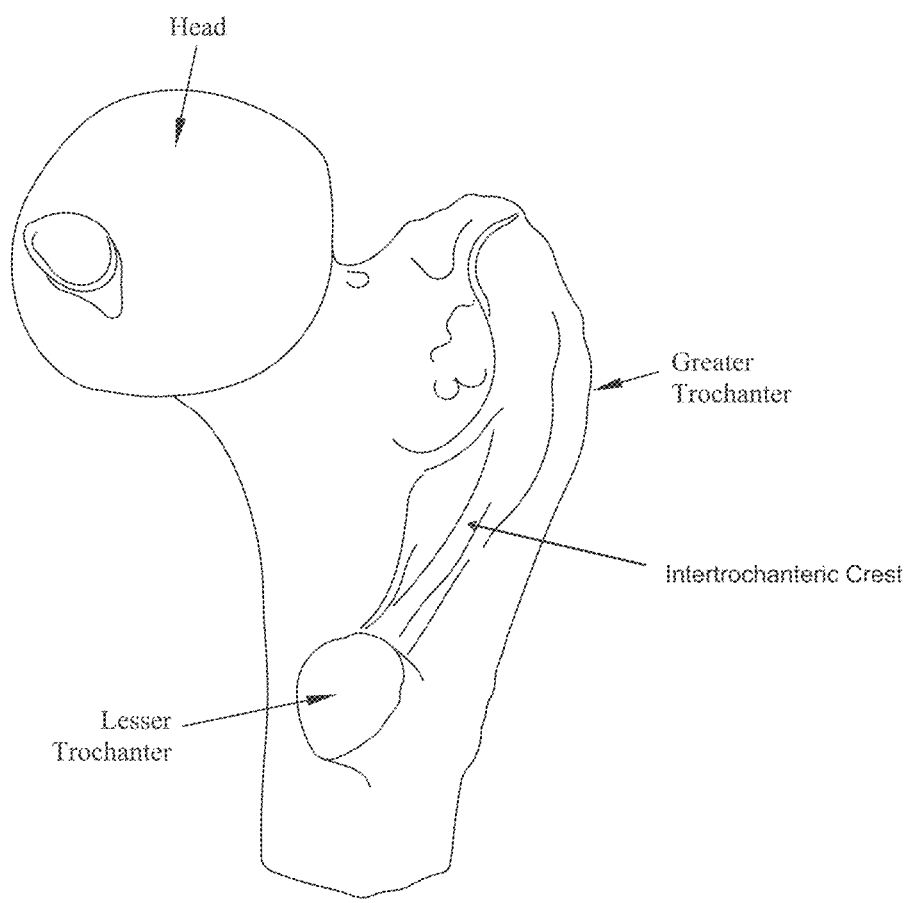
FIG. 4 is a schematic posterior view of the top end of the femur.
Figure 5:
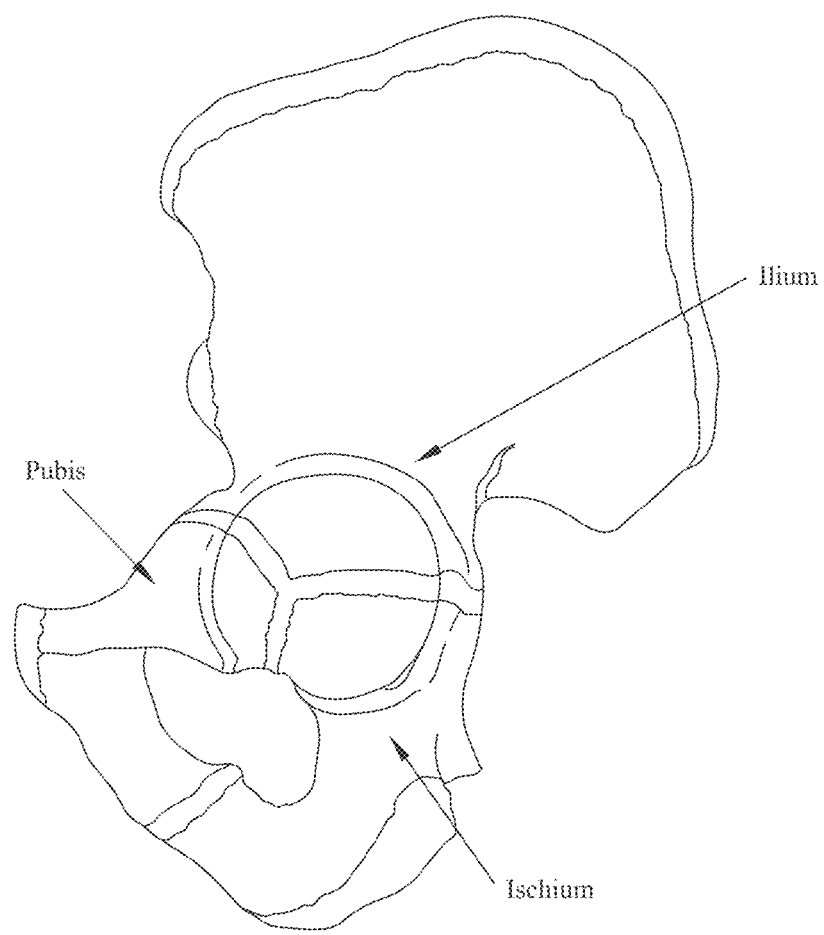
FIG. 5 is a schematic view of the pelvis.
Figure 6:
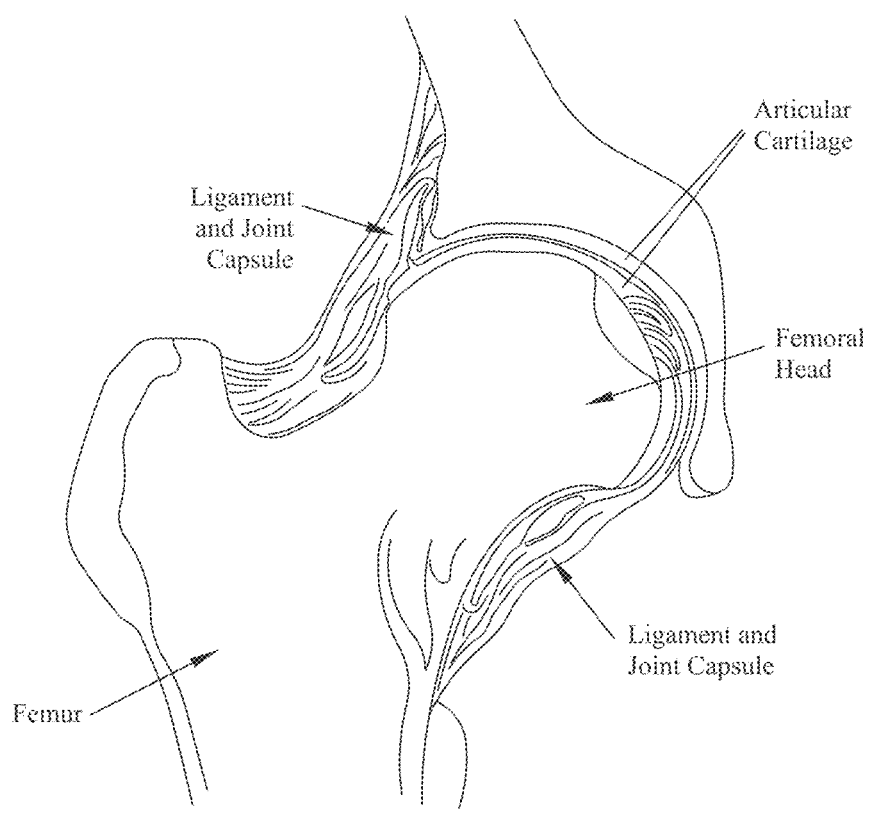
FIGS. 6-12 are schematic views showing bone and soft tissue structures in the region of the hip joint.
Figure 7:
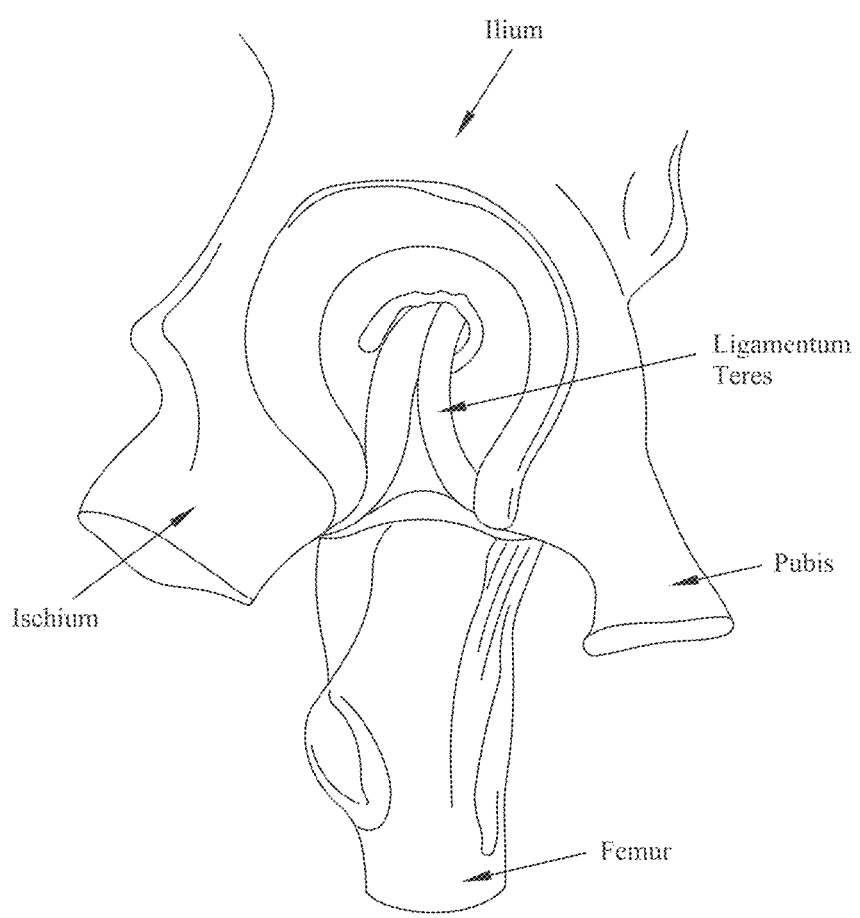
Figure 8:
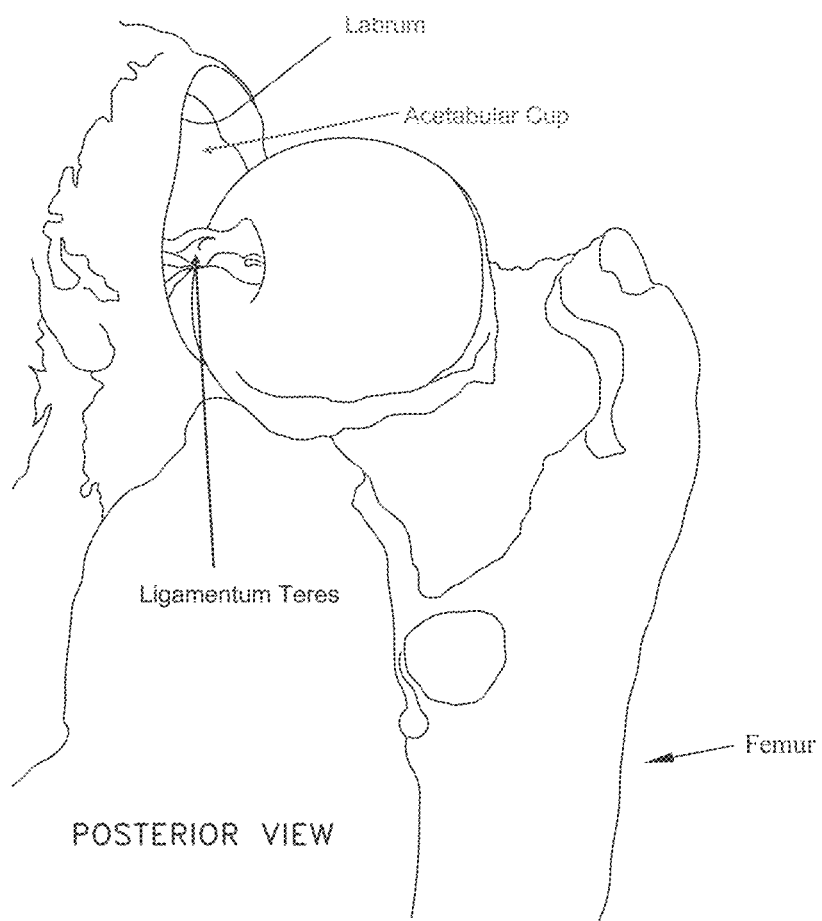
Figure 9:
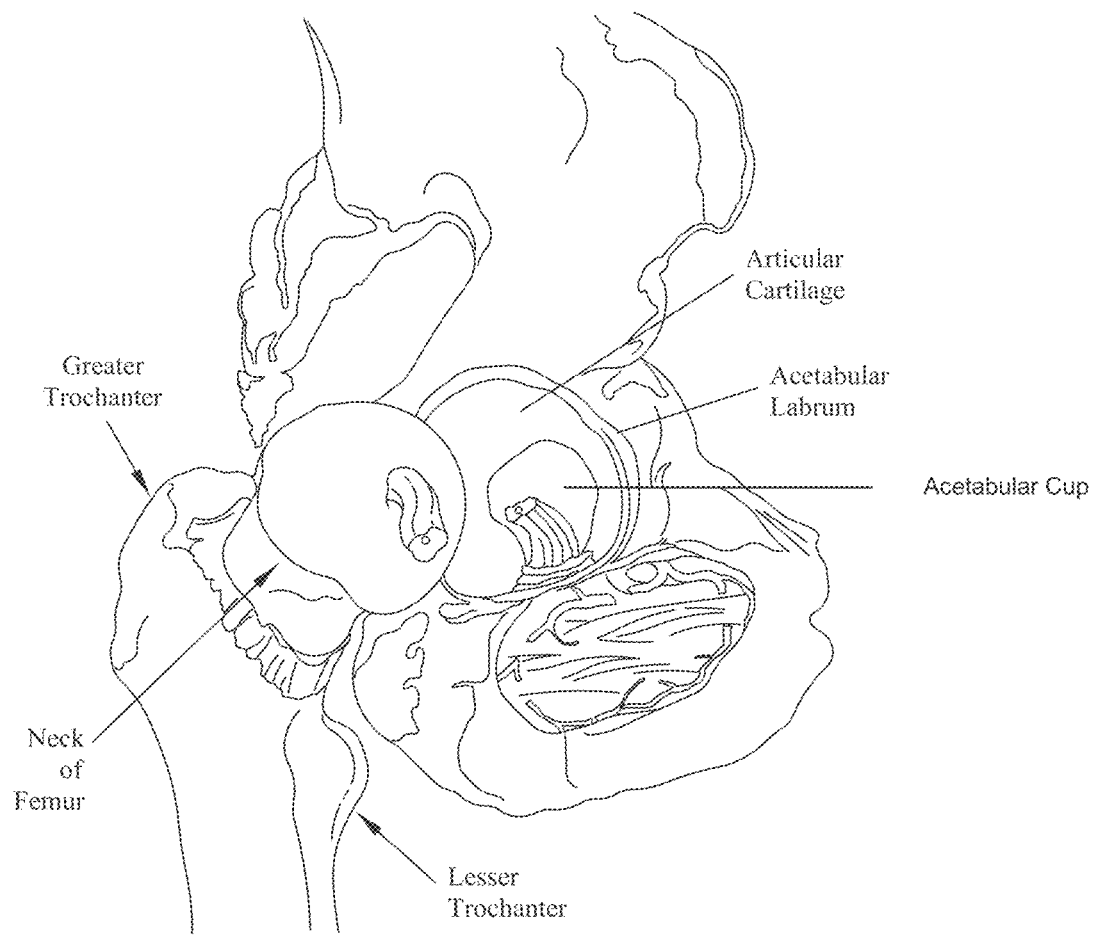
Figure 10:
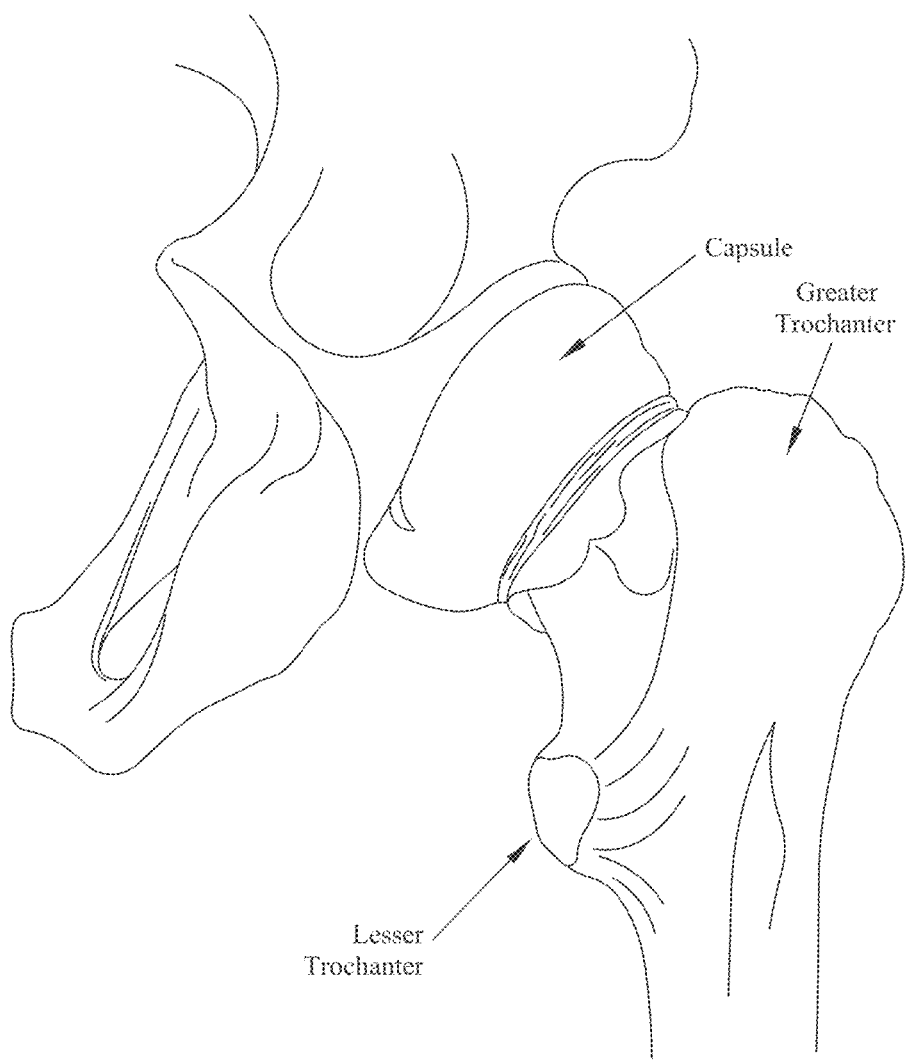
Figure 11:
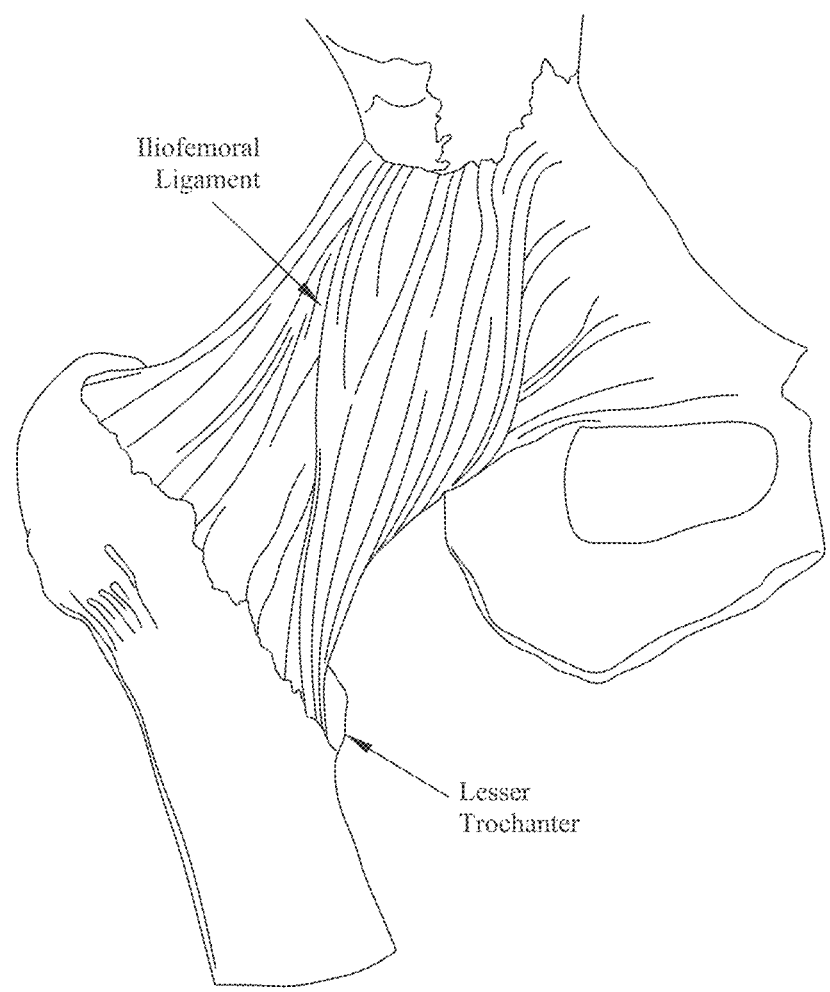
Figure 12:
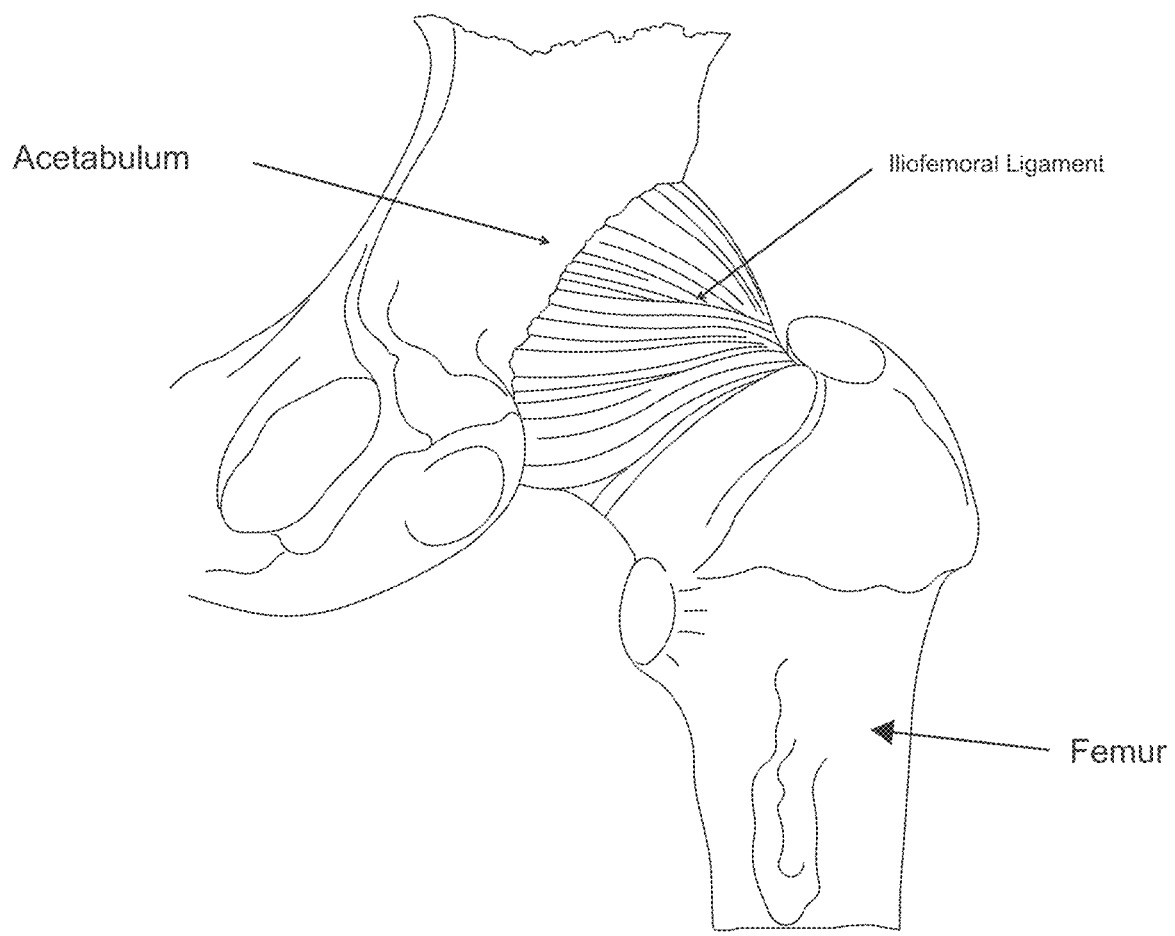
Figure 13:
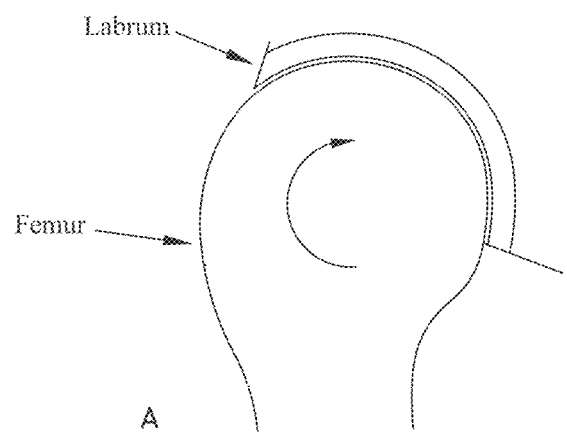
FIG. 13 is a schematic view showing cam-type femoroacetabular impingement (i.e., cam-type FAI)
Figure 13:
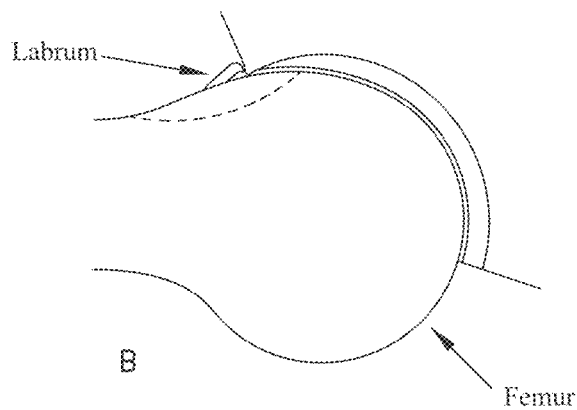
Figure 14:
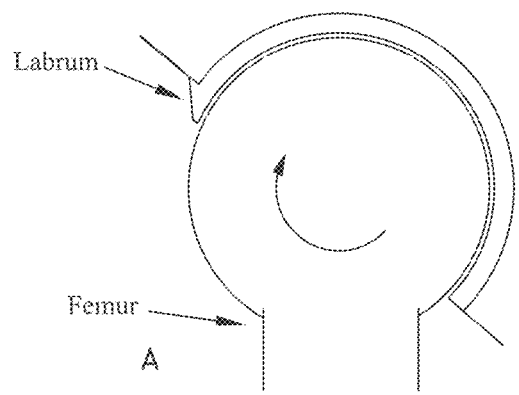
FIG. 14 is a schematic view showing pincer-type femoroacetabular impingement (i.e., pincer-type FAI)
Figure 14:
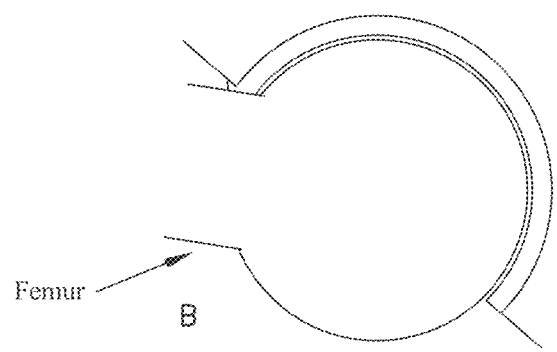
Figure 15:
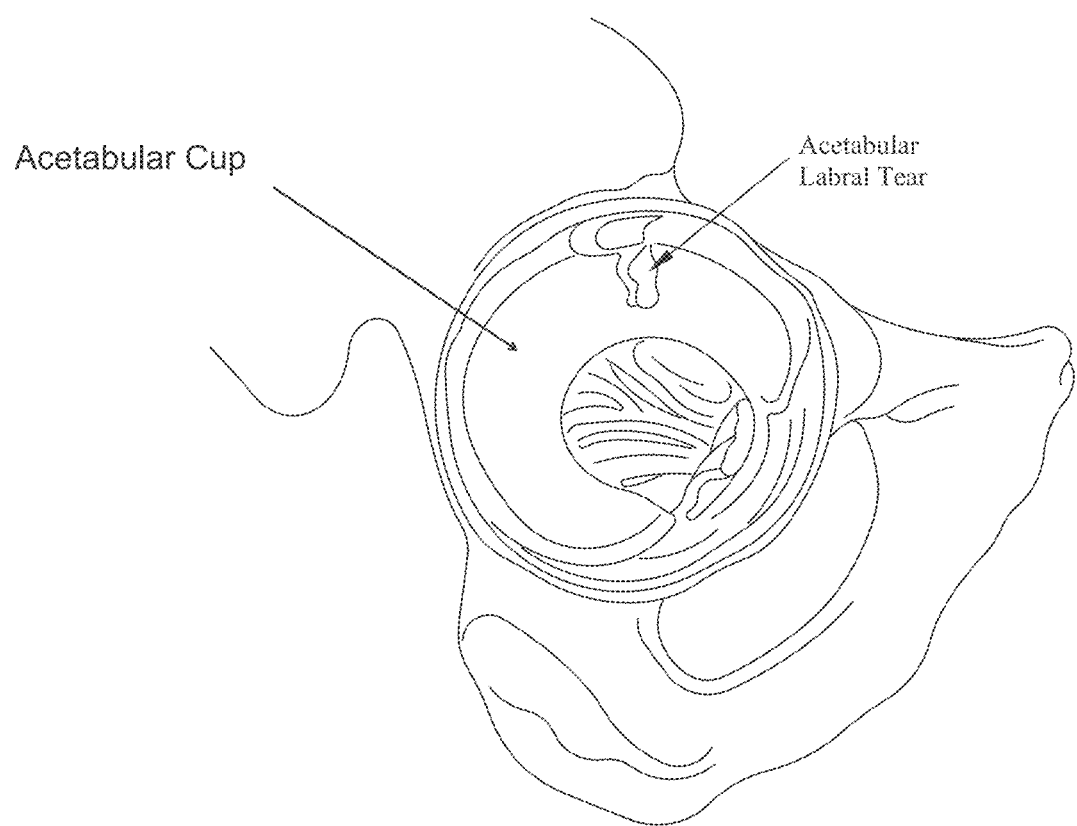
FIG. 15 is a schematic view showing a labral tear.
Figure 16:
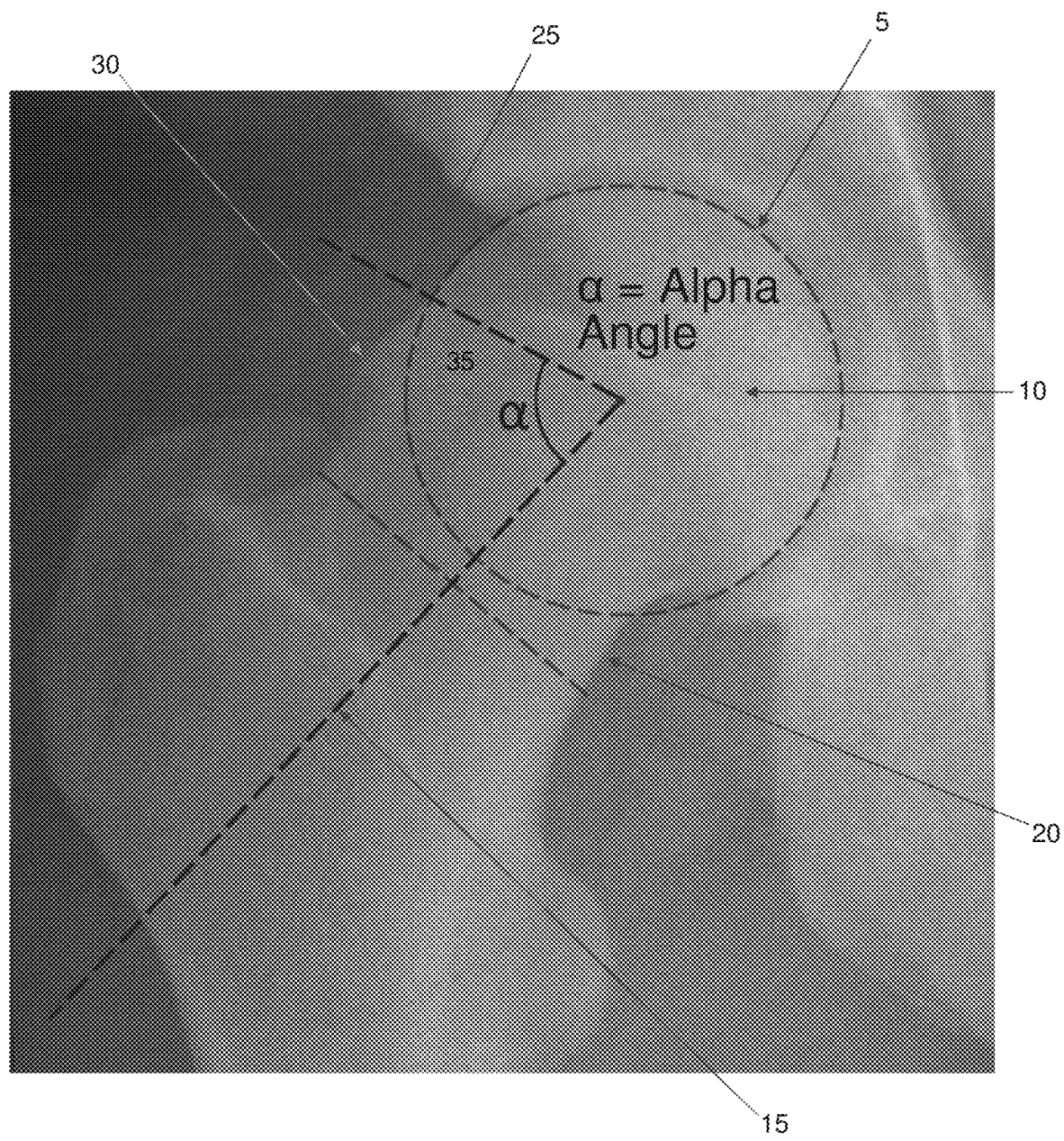
FIG. 16 is a schematic view showing an Alpha Angle determination on the hip of a patient.
Figure 17:
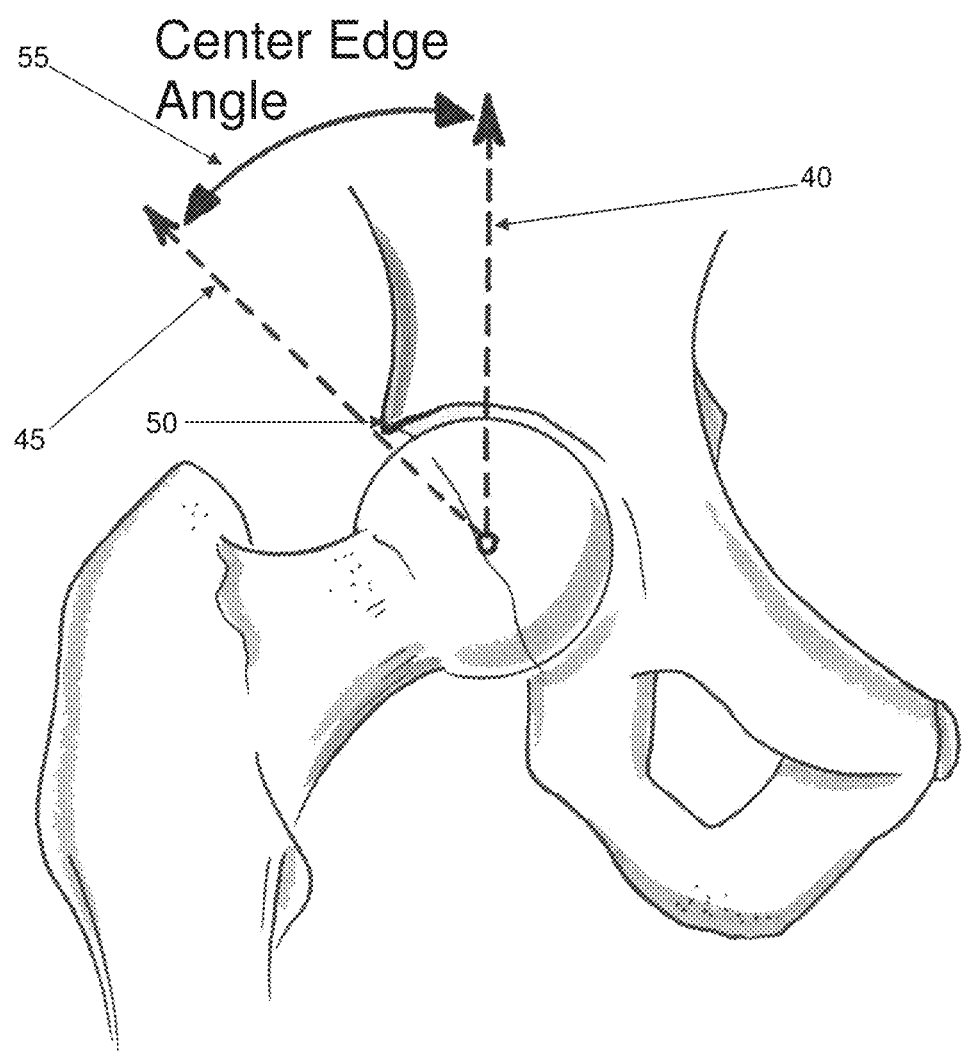
FIG. 17 is a schematic view showing a Center Edge Angle determination on the hip of a patient.
Figure 18:
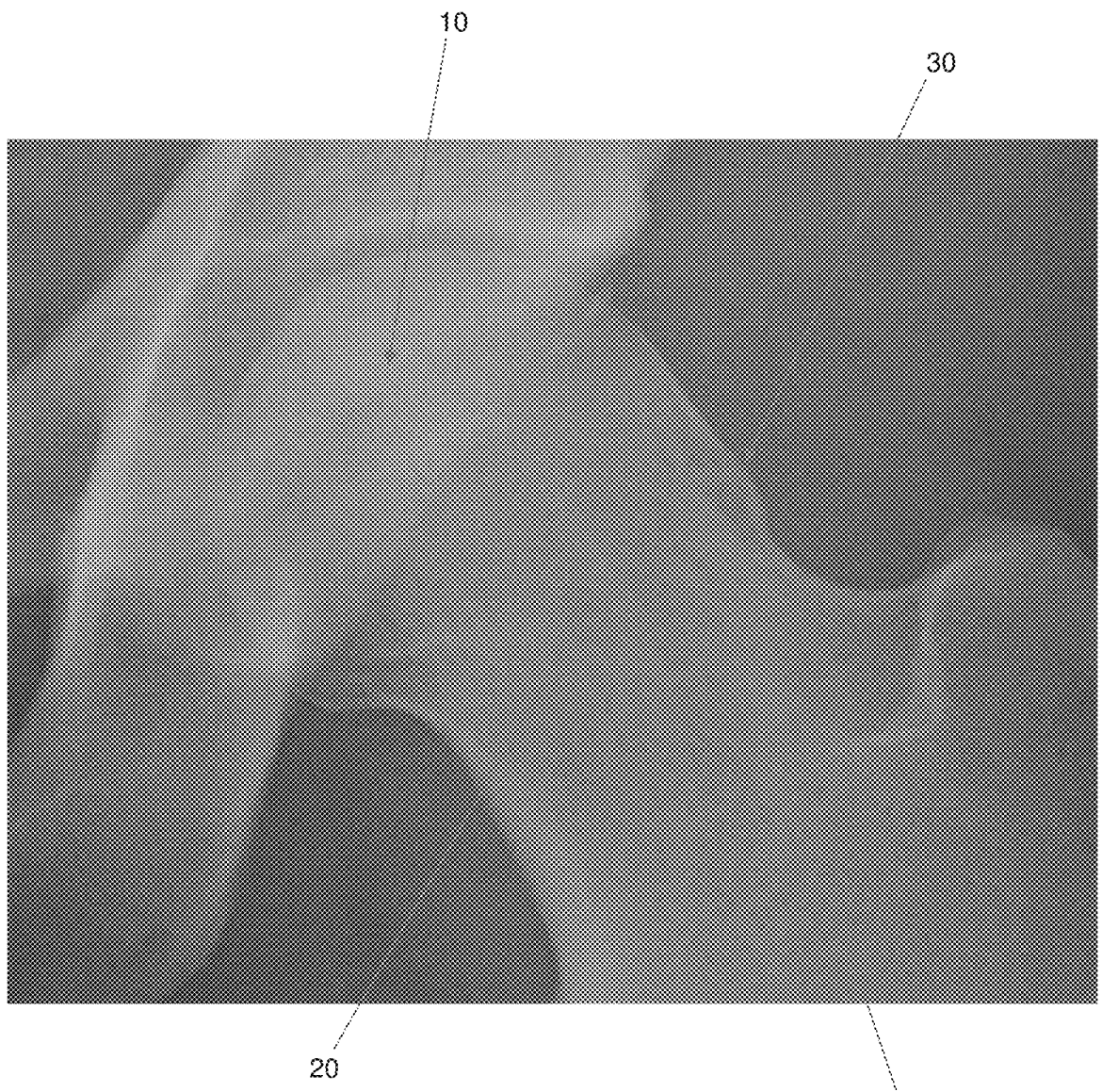
FIG. 18 is a schematic view showing the head and neck of a femur and a cam-type femoroacetabular impingement site.

Method and Apparatus for the Treatment of Cam-Type Femoroacetabular Impingement in a Hip Joint FIG. 18 is a schematic view of a femur 60 comprising the femoral head 10 and the femoral neck 20, and illustrates the cam-type femoroacetabular impingement site 30 which needs to be debrided in order to treat the cam-type femoroacetabular impingement.

The present invention comprises the provision and use of a novel computer visual guidance system which analyzes an X-ray image (e.g., an intra-operative C-arm X-ray image) to automatically measure features of the hip, such as the cam pathology (e.g., by using an "Alpha Angle" calculation, see below), and then annotates the X-ray image for use by the surgeon in treating the cam pathology. The purpose of this invention is to guide the surgeon to an optimal resection of the pathology which is causing the impingement. As noted above, arthroscopic resections are currently "eye-balled" and the surgeon has no objective way to define completion of the boney resection. This leads to over-resection and, most commonly, under-resection of the cam—which is the leading cause of revision hip arthroscopy. Furthermore, surgeons currently have no ability to measure Alpha Angle during surgery, so there is no means to determine if sufficient bone has been removed. The present invention addresses this problem by providing means which automatically analyze an X-ray image with respect to a cam pathology and then automatically annotate the X-ray image with guidance features which can be used by the surgeon in treating the cam pathology.

More particularly, the present invention comprises a series of steps which start with an X-ray image and yields a measurement of a feature of the hip (e.g., the Alpha Angle) and an annotation which is correctly displayed on that X-ray image for the surgeon to be able to assess the pathology and progress towards proper resection.

Figure 19:
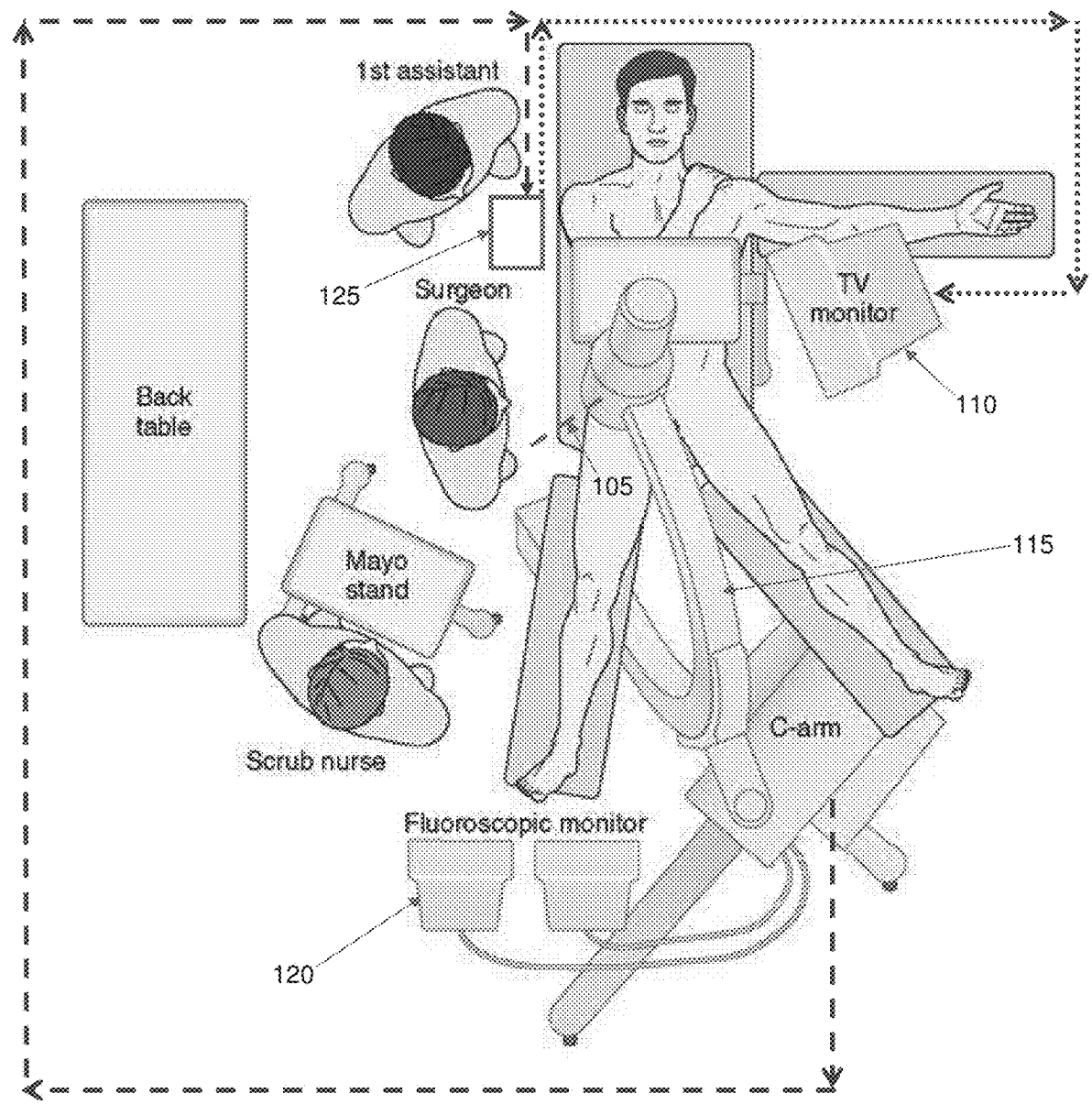
FIG. 19 is a schematic view showing a surgical suite incorporating the present invention.

FIG. 19 shows a surgical suite incorporating the present invention. More particularly, in a typical arthroscopic surgical suite, the surgeon uses an arthroscope 105 and a monitor 110 to directly view an internal surgical site. In addition, the surgeon also uses a C-arm X-ray machine 115 and a fluoroscopic monitor 120 to image the internal surgical site. In accordance with the present invention, there is also provided a novel computer visual guidance system 125 which automatically analyzes an X-ray image obtained from C-arm X-ray machine 115 with respect to selected features of the hip associated with a cam pathology and then automatically annotates the X-ray image displayed on computer visual guidance system 125 with guidance features for use by the surgeon in treating the cam pathology. In one preferred form of the invention, computer visual guidance system 125 comprises a general purpose computer having input and output means and which is appropriately programmed so as to provide the functionality disclosed herein. In one preferred form of the invention, computer visual guidance system 125 comprises a tablet device with an integrated computer processor and user input/output functionality, e.g., a touchscreen. In this form of the invention, the computer visual guidance system 125 may be located in the sterile field, for example, the computer visual guidance system 125 may comprise a touchscreen tablet mounted to the surgical table or to a boom-type tablet support. The computer visual guidance system 125 may be covered by a sterile drape to maintain the surgeon's sterility as he or she operates the touchscreen tablet. Alternatively, computer visual guidance system 125 may comprise other general purpose computers with appropriate programming and input/output functionality, e.g., a desktop or laptop computer with a keyboard, mouse, touchscreen display, heads-up display, voice activation feature, pupil reading device, etc.

Figure 20:
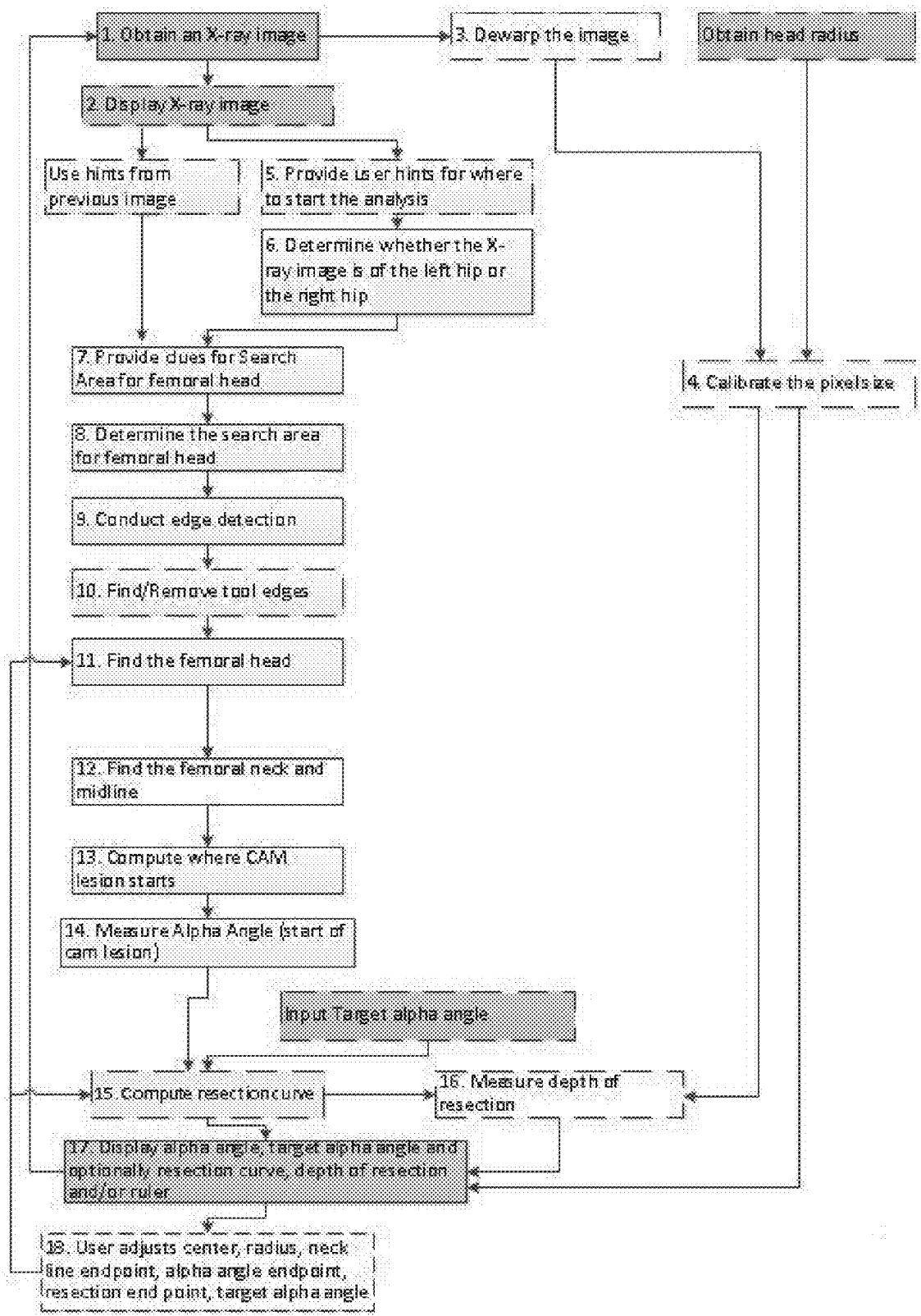
FIG. 20 is a flowchart which shows one preferred implementation of the present invention.

In one preferred form of the invention, the invention comprises the steps discussed below and shown in flowchart form in FIG. 20.

Step 1: Obtain The X-ray Image

In the preferred form of the invention, the first step is to obtain the X-ray image. There are multiple ways to effect this.

1A. Directly From A C-Arm X-ray Machine

In one form of the invention, the X-ray image is obtained directly from a C-arm X-ray device, e.g., C-arm X-ray machine 115 (FIG. 19). This may be done by wire or wireless connection between C-arm X-ray machine 115 and computer visual guidance system 125.

Figure 21:
FIG. 21 is a schematic view showing a typical image acquired by a C-arm X-ray device.

These images from the C-arm X-ray device are typically circular with a black background. Bones are dark, soft tissue is lighter, no X-ray absorption is white. See FIG. 21.

Since the computer visual guidance system 125 (FIG. 19) is separate from the C-arm X-ray device, it is necessary to detect when a new image has been taken by the C-arm X-ray device. This may be done by connecting the computer visual guidance system 125 directly to the video output of the C-arm X-ray device, and using the method described in International (PCT) Patent Application Publication No. WO 2012/149664A1 (which corresponds to International (PCT) Patent Application No. PCT/EP2011/057105) to detect when a new image is taken. In essence, this method looks at image blocks to see if there is a significant change between one image block and the previous image block. If there is a large change between image blocks, then an image is captured and this captured image is the image used in the method of the present invention.

Alternatively, other approaches well known in the art of X-ray imaging may be used to detect when a new image is taken.

The X-ray image may also be transmitted from C-arm X-ray machine 115 to computer visual guidance system 125 over a local area network. In this form of the invention, C-arm X-ray machine 115 communicates with the local area network with, for example, a wireless or wired connection. In this form of the invention, computer visual guidance system 125 receives the X-ray image from the local area network. Depending on the network speed, this can occur substantially instantaneously.

1B. Previous Image From Surgery

A surgeon may also want to use an image taken earlier in the surgical procedure. In this scenario, a previous image can be retrieved from, for example, the C-arm X-ray machine 115 and imported into computer visual guidance system 125. A previous image may, alternatively, be retrieved from the computer visual guidance system 125 and used for further analysis.

1C. Previous Image Taken Prior to Surgery

Figure 22:
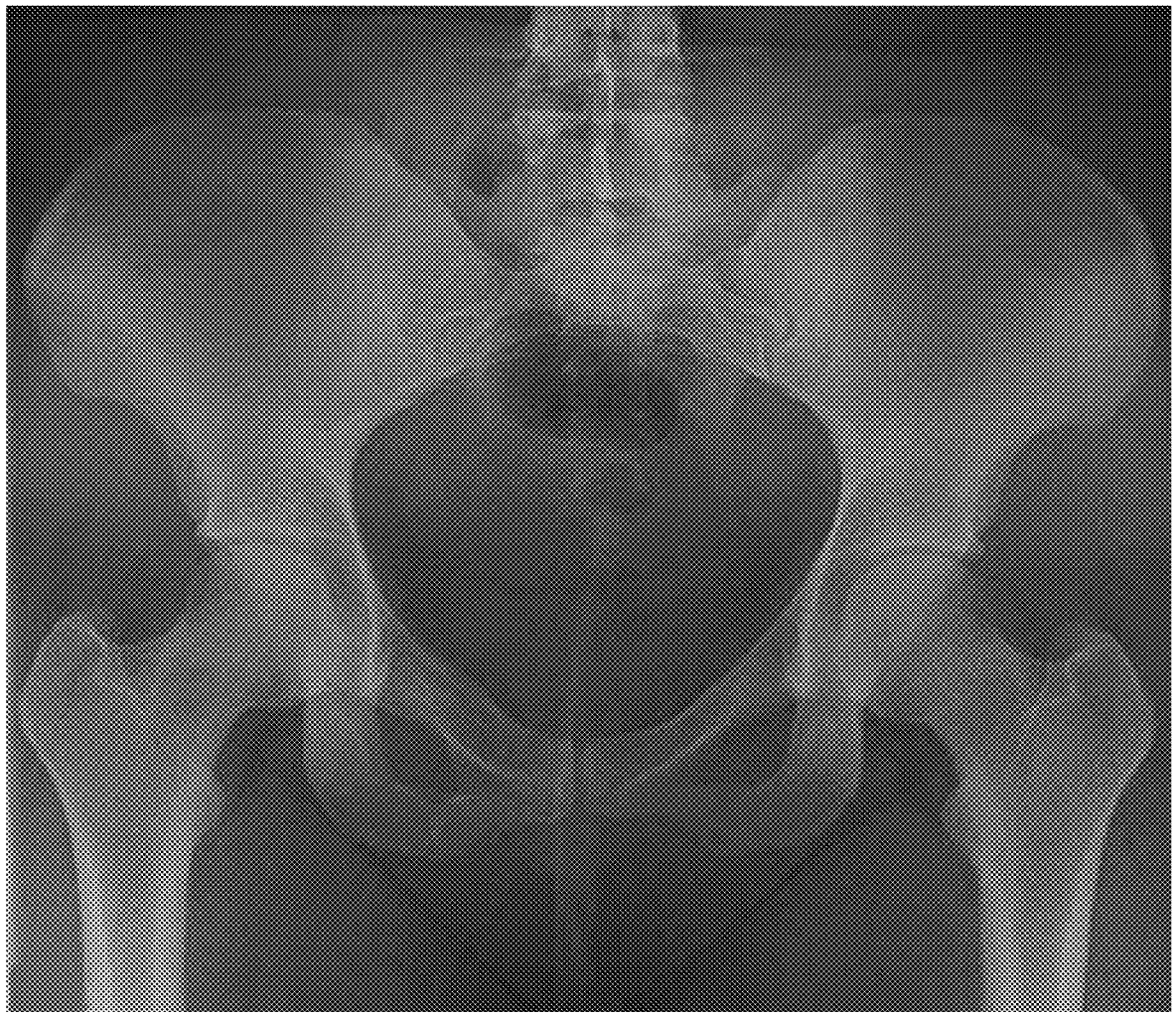
FIG. 22 is a schematic view showing a typical image acquired from a medical center's PACS servers.

A surgeon may also want to use an image taken during pre-operative diagnostic X-rays, etc. In this form of the invention, computer visual guidance system 125 communicates with the hospital's PACS servers, and an image taken previously is downloaded and the image used in the method of the present invention. Where a pre-operative image is used, the pre-operative image is typically rectangular with no black background. The pre-op images are inverted relative to the C-arm images. Bones are light, soft tissue is darker, no X-ray absorption is black. A pre-op image needs to be inverted for analysis (i.e., so as to be similar to a C-arm image) and then inverted back after analysis for viewing. See FIG. 22.

It should be appreciated that other pre-operative image configurations may also be used—what is important is that both pre-operative and intra-operative images can be utilized with computer visual guidance system 125. It should also be appreciated that a pre-operative image may be provided to computer visual guidance system 125 by other means, e.g., a USB drive or other static drive or portable storage device, etc.

Step 2: Display

After the X-ray image is acquired, it is displayed to the surgeon on computer visual guidance system 125 and/or monitor 110. See FIGS. 21 and 22. The advantage of displaying the X-ray image to the surgeon prior to making measurements from that X-ray image is that the surgeon can view the acquired image and determine if it is an appropriate image to analyze and, if not, take another X-ray image without losing valuable operating room (OR) time while waiting for computer visual guidance system 125 to process the image.

Step 3: De-warp The Image

In one preferred form of the invention, the next step is to de-warp the intra-operative X-ray image.

Figure 23:
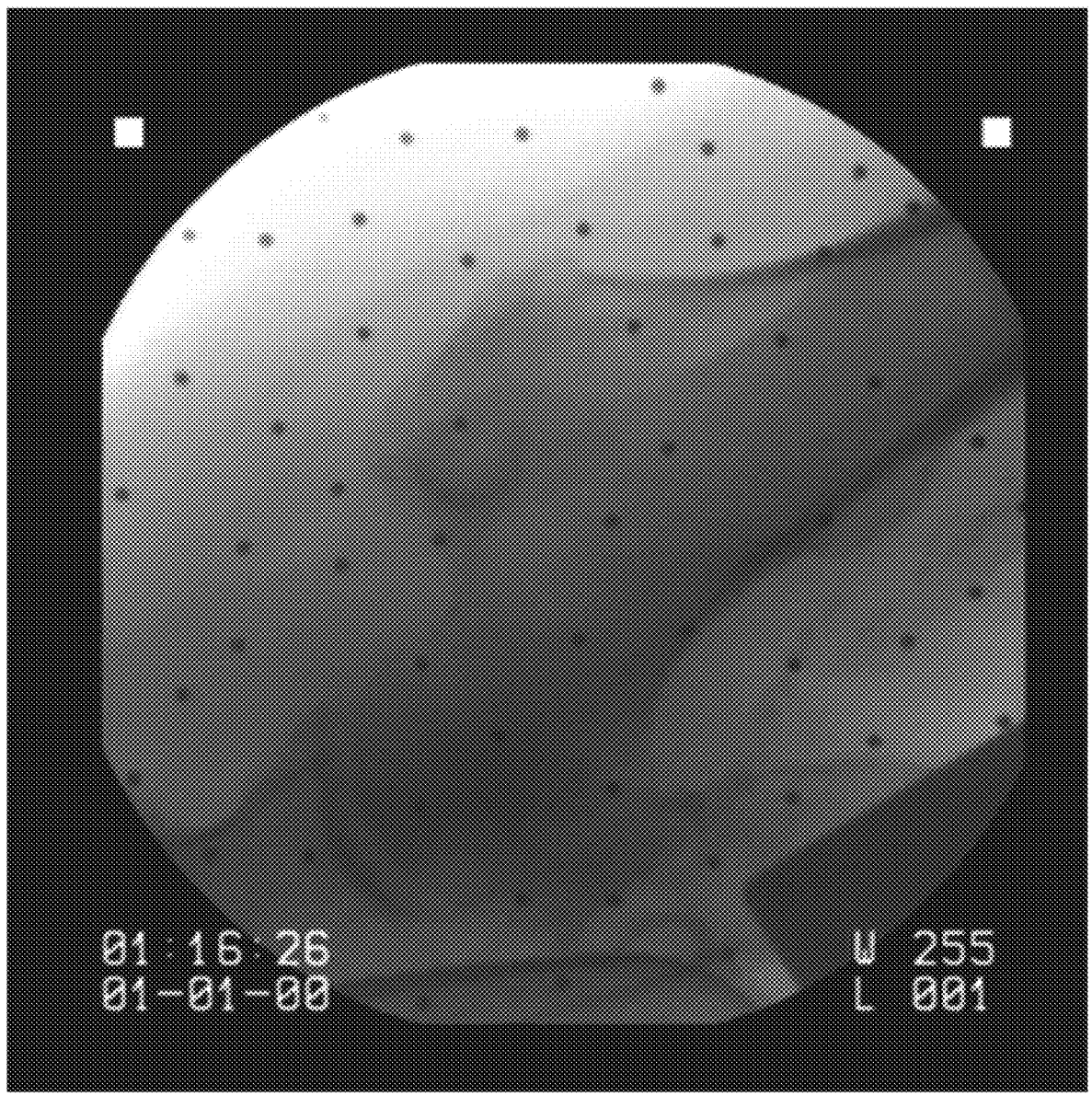
FIG. 23 is a schematic view showing how an X-ray image can be de-warped.

More particularly, images from some C-arm X-ray machines 115 are often distorted ("warped") such that every object in the image may not be scaled identically. This is due to the fact that the X-ray beam is not perfectly linear. Typically, objects closer to the X-ray source of the C-arm X-ray device appear larger (and comprise more pixels). Correspondingly, other objects of the same size located further away from the X-ray source of the C-arm X-ray device will appear smaller (and comprise less pixels). To make precise measurements, this warping needs to be removed. For example, the Stryker "Fluoro Disc" product provides this de-warping function by projecting a predetermined pattern onto the intra-operative X-ray image. See FIG. 23.

It should be appreciated that this de-warping step is optional, however, it makes calibration and any subsequent measurements more accurate (e.g., see Step 16 below), and is generally desirable since it makes the Alpha Angle measurement more accurate by correcting for image distortion via the de-warping process. Some newer C-arm X-ray devices (e.g., those with a flat panel detector) may automatically provide de-warped images and therefore may not require this de-warping step.

Step 4: Calibrate The Pixel Size

In the preferred form of the invention, the next step is to calibrate the pixel size. It should be appreciated that this pixel calibration step is optional, however, it is required for the measurement function in Step 16, and is generally desirable since it makes measurements of features shown on an X-ray image more accurate. Some newer C-arm X-ray devices (e.g., those with a flat panel detector with integrated DICOM) may provide calibrated pixel sizes and therefore may not require this pixel calibration step.

More particularly, in order to accurately measure distances in the image, pixels must first be calibrated (i.e., so that a pixel in a given image is correlated to a real-world dimension). It is also helpful to know the pixel size when trying to limit the diameters of the femoral head that are being analyzed (see Step 11A below).

It is important to note that de-warping the image (as described above in Step 3) will improve the accuracy of pixel calibration.

There are multiple ways to calibrate pixel size. Some preferred approaches will now be discussed.

4A. External Calibration Marker

Figure 24:
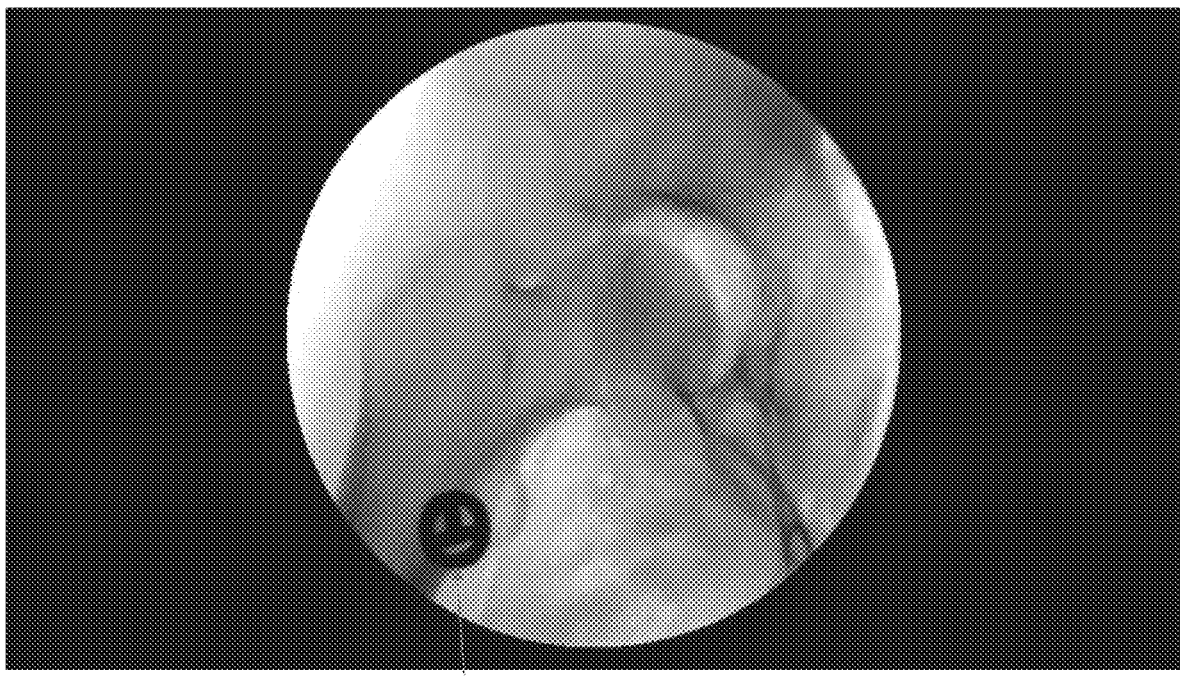
FIG. 24 is a schematic view showing one way for calibrating pixel size.

A first way to calibrate pixel size is to put a radio-opaque marker on the skin of the patient that is visible in the X-ray image. This radio-opaque marker can be large and placed a few centimeters distal from the greater trochanter. The radio-opaque marker has an adhesive on its rear side to stick to the patient's skin. The radio-opaque marker is preferably disposable. In one preferred form of the invention, the marker is flat, circular and simple to identify with computer vision. Since the marker is of known size (mm), and the number of pixels can be counted on the X-ray (px), it is a simple matter to calculate mm/px (i.e., to calculate the pixel size). Note that, in practice, it is best to treat the circle as an ellipse, since the radio-opaque marker does not always lie flat on the patient—therefore, one can use the major axis of the ellipse for calibration. Note also that this approach for calibrating pixel size is the furthest "out of plane" (i.e., out of the plane of the object of interest, since the marker is on the surface of the skin and the object of interest is at an internal site), so it likely has calibration error without de-warping the image. See FIG. 24, which shows a radio-opaque marker 130 visible in the X-ray image.

4B. Internal Calibration Marker

Figure 25:
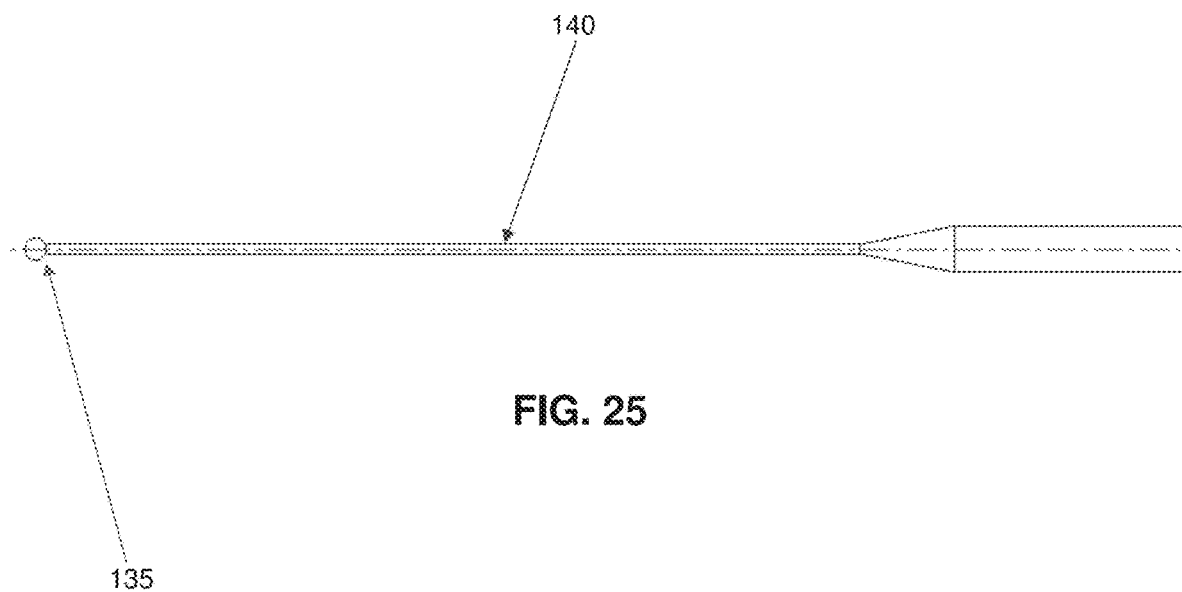
FIGS. 25 and 26 are schematic views showing another way for calibrating pixel size.
Figure 26:
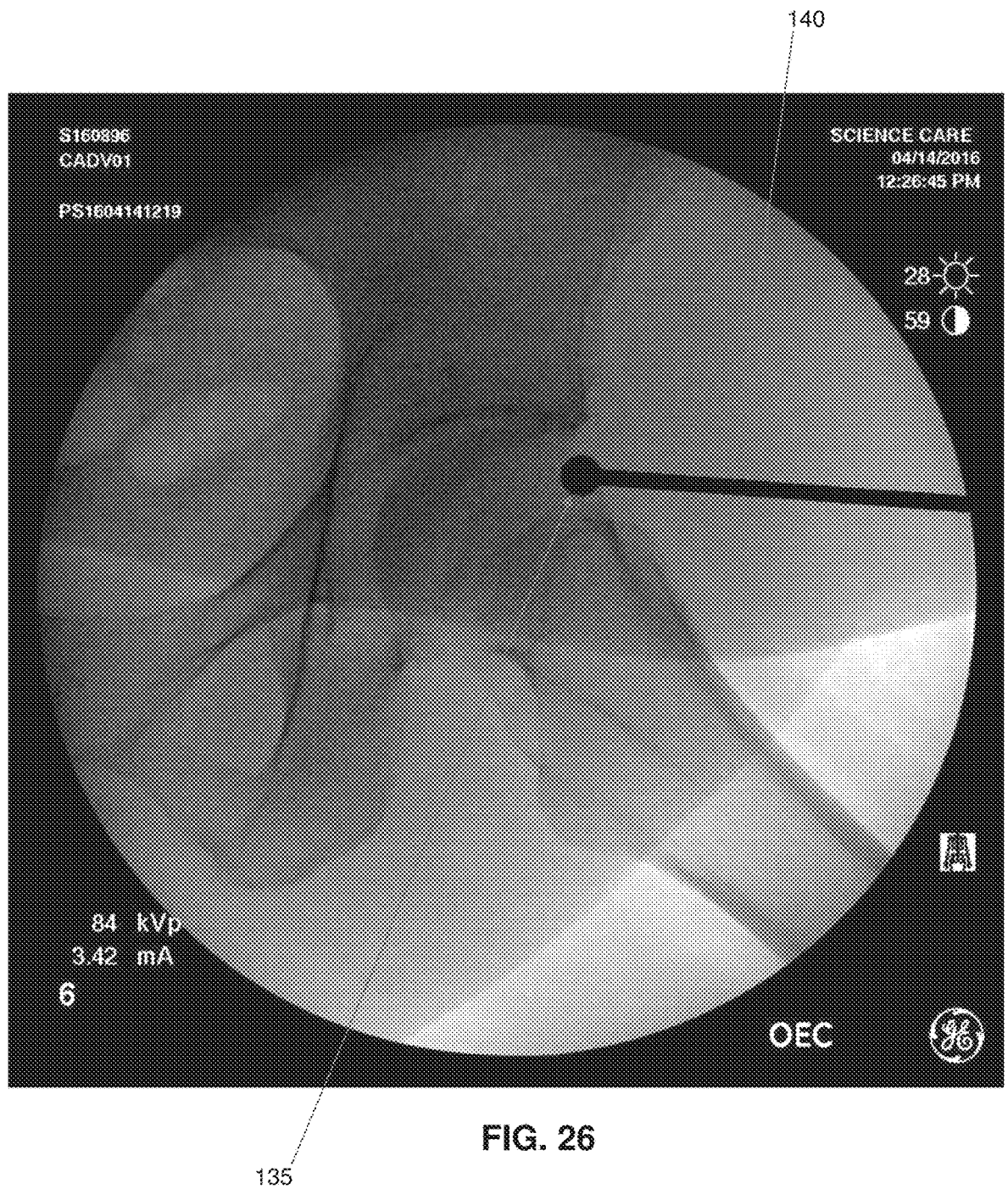

Instead of using an external calibration marker, pixel calibration can be effected by placing a calibration marker of known size into the joint space and, more preferably, directly on the bone. The calibration marker is radio-opaque and thus will be visible on X-ray. It is preferably highly radio-opaque, for example constructed of solid metal, and thus will have high contrast with the anatomy. This would make the "plane" of the pixel calibration more accurate, i.e., the calibration marker will lie closer to the plane of the object of interest. This calibration marker can be re-usable and sterilized by almost any method due to its simplicity. See FIGS. 25 and 26, which show a radio-opaque calibration marker 135 at the distal end of an instrument 140.

4C. Using The Burr/Scope In The X-ray Image

Figure 27:
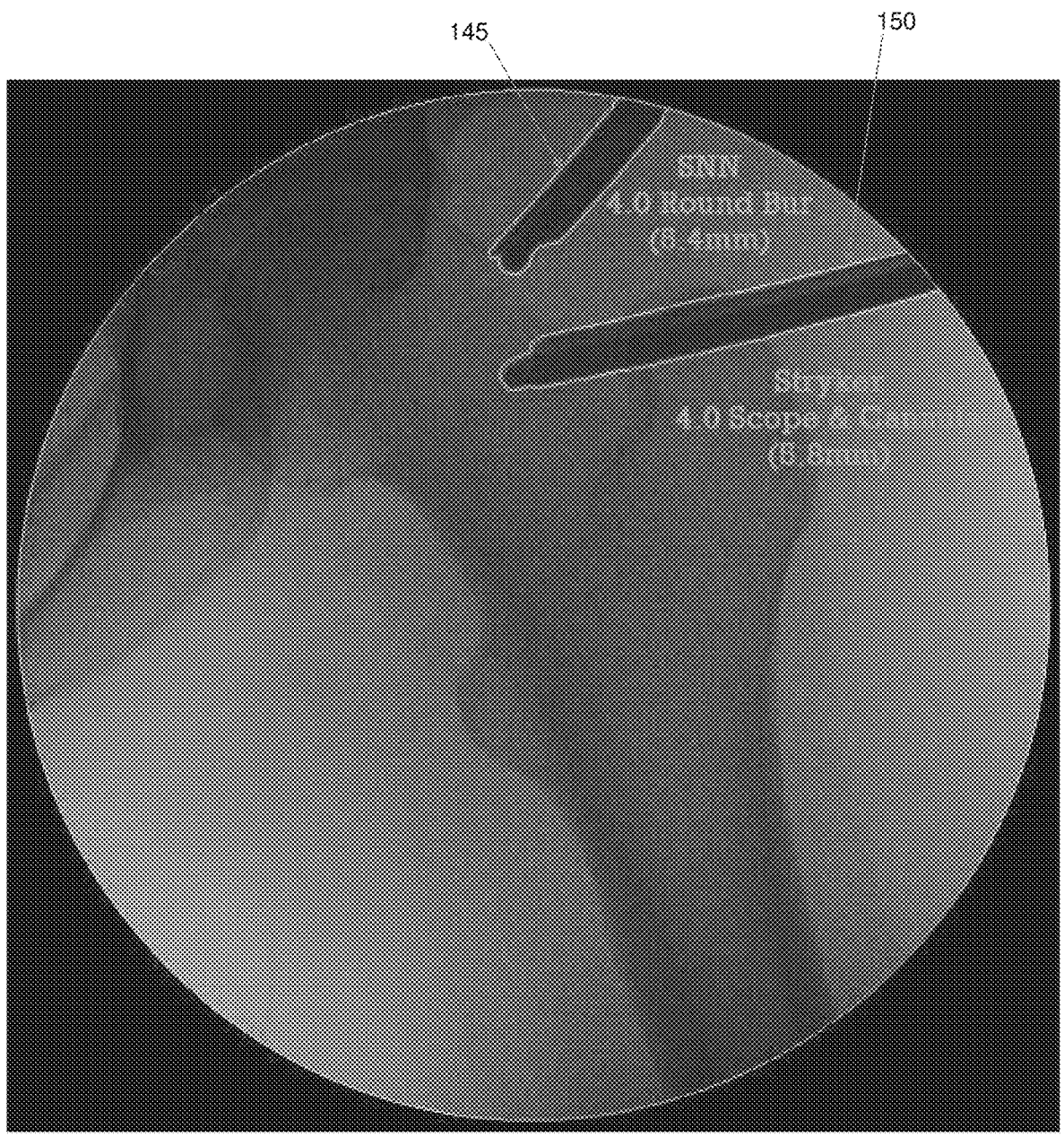
FIG. 27 is a schematic view showing still another way for calibrating pixel size.

One downside of using a dedicated calibration marker is that it adds an additional instrument to the procedure, and can disrupt the natural workflow of the medical procedure. If, instead, surgical instruments of known size that are already present in the image (e.g., the burr and scope) can be used, this disruption can be avoided. These surgical instruments (e.g., burr and scope) are much more complex shapes, however, and tend to be more difficult to identify with computer vision. Fortunately, 3D computer models of these surgical instruments are generally available, so these 3D models can be matched up to the 2D X-ray images from the C-arm X-ray machine 115 to first identify the surgical instruments, and then their known dimensions can be used for pixel calibration. Alternatively, some surgical instruments include encoded information that identifies the surgical instrument; by way of example but not limitation, this information can be encoded into the surgical instrument by way of an EPROM carried by the surgical instrument. This identifying information can include the make and model number of the surgical instrument, or may include physical dimensions. This information can be passed to computer visual guidance system 125 so that a known dimension of the surgical instrument can be used for pixel calibration. If the information is in the form of a make and model number, then computer visual guidance system 125 may comprise a table of dimensions associated with that particular surgical instrument. See FIG. 27, which shows a burr 145 and a scope 150.

4D. Using A Pre-Operative Image

The pixel size in the image may also be calibrated based on pre-operative images that have a known scale, such as MRI or CT images. More particularly, if the pre-operative image has a known scale, then an object appearing in both the pre-operative image and intra-operative image can be compared to determine pixel calibration. For example, the radius of the femoral head can be measured. The femoral head radius can be determined from the X-ray image in number of pixels and, using the known femoral head radius measured pre-operatively, the pixel size relative to real-world distance can be computed. However, if the pre-operative and intra-operative images are not taken in the same plane, a small error may be present due to imperfect femoral head symmetry. Creating 2D images from a 3D computer model increases the ability to match the images well and minimize error.

In one preferred form of the invention, the pixel size in the X-ray image obtained from C-arm X-ray machine 115 is calibrated by (i) first obtaining a measurement of the radius of the femoral head from a pre-operative image, and then (ii) correlating the pixel count of the radius of the femoral head with the previously-obtained measurement of the radius of the femoral head in order to calibrate the pixel size in the X-ray image obtained from C-arm X-ray machine 115. In this form of the invention, the measurement from the pre-operative image can be manually input into computer visual guidance system 125 by the operator (for example, the surgeon). In another embodiment, computer visual guidance system 125 can read the measurement from a file that it accesses. For example, the femoral head size could be meta data associated with a pdf file that computer visual guidance system 125 accesses. In this embodiment, the pdf file can be a pre-operative plan generated from a pre-operative 3D image (e.g., a CT scan).

In order to calibrate pixel size by this method, the sequence of steps must be changed. This Step 4D would come after the femoral head has been found using computer vision, e.g., after Step 11 below.

Step 5: Provide Hints

The next step is to provide "hints" to the system. These "hints" generally serve to speed up the analysis, however, they can also be used for other purposes, e.g., to help identify whether the X-ray image is of the left hip or the right hip, or to help in computing the resection curve (see below), etc.

Figure 28:
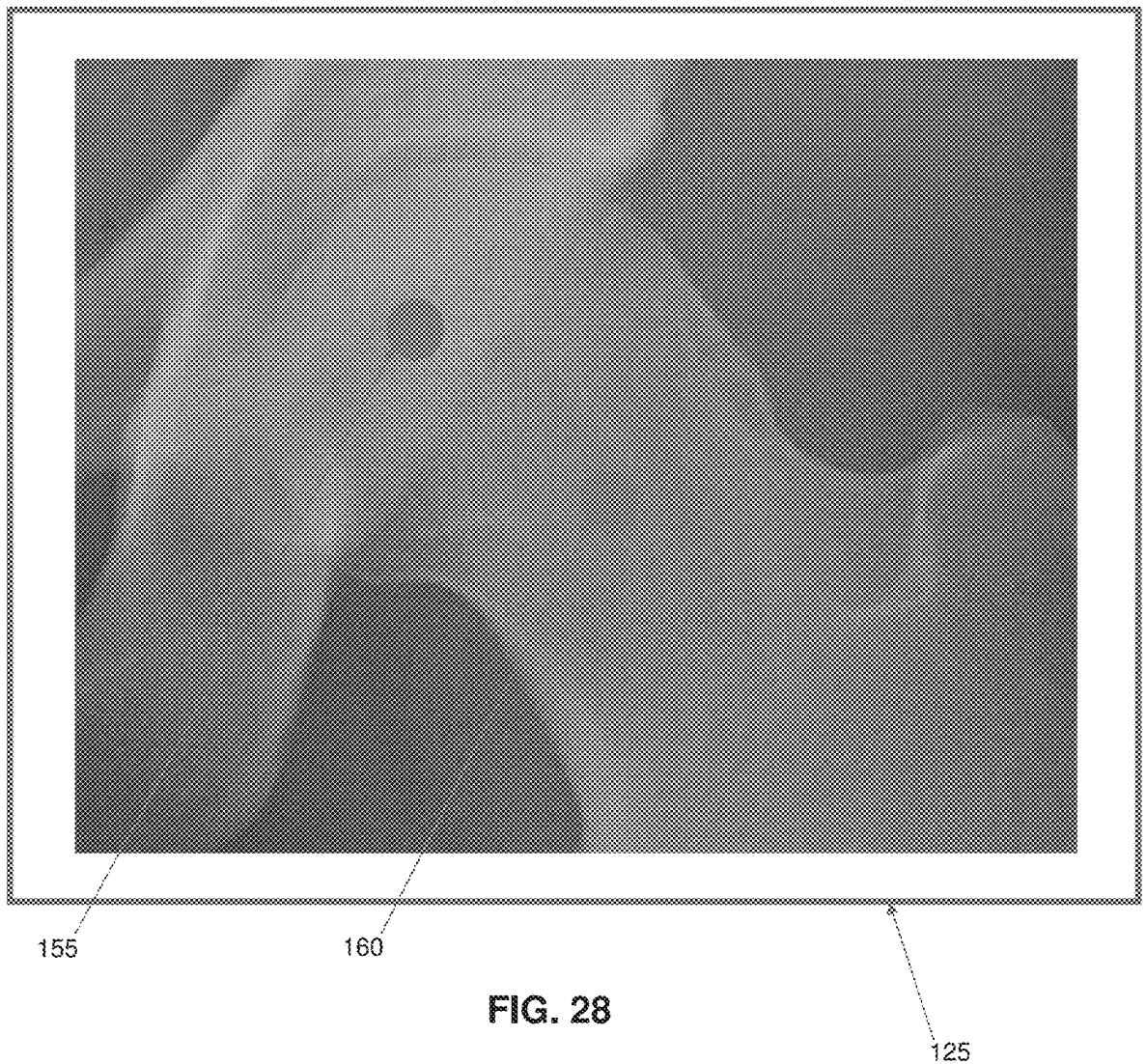
FIG. 28 is a schematic view showing how a surgeon can provide "hints" to the system using touchscreen tablet 130.

In one preferred form of the invention, and looking now at FIG. 28, the surgeon preferably provides two hints to the system: a femoral head hint 155 and a femoral neck hint 160. This is preferably done by displaying the X-ray image obtained by C-arm X-ray machine 115 onto an output screen of computer visual guidance system 125 (e.g., the touch-screen of a tablet comprising computer visual guidance system 125), and then prompting the surgeon to (i) touch the center of the femoral head so as to provide a femoral head hint 155, and (ii) prompting the surgeon to touch the mid-line of the femoral neck so as to provide a femoral neck hint 160.

Note that once the surgeon provides the femoral head hint 155 and the femoral neck hint 160 to the system, these hints may be automatically incorporated into subsequent images obtained by C-arm X-ray machine 115. More particularly, in this form of the invention, a new X-ray image is compared to a previous image containing the femoral head hint 155 and the femoral neck hint 160. If the new image is sufficiently similar to the previous image, then the femoral head hint 155 and the femoral neck hint 160 from the previous image are used for the new image. This will save valuable OR time and be convenient for the surgeon in that the surgeon will not have to provide new hints to computer visual guidance system 125 for each new image acquired.

Step 6: Determine Whether The X-ray Image Is Of The Left Hip Or The Right Hip

In the preferred form of the invention, the next step is to determine whether the X-ray image is of the left or the right hip.

More particularly, knowing whether a left hip or right hip is being imaged enables computer visual guidance system 125 to more efficiently analyze the X-ray image; for example, to search for the femoral neck, computer visual guidance system 125 only need look on the right side of the femoral head for a left hip or on the left side of the femoral head for a right hip.

There are multiple ways to determine whether the X-ray image is of the left or the right hip. In any method, it is assumed that the X-ray image is provided to the visual guidance system in the correct manner, and has not been flipped (e.g., reversed), and is generally oriented with the top of the image being in the superior (i.e., cephalad) direction of the patient.

6A. Patient Data

Prior to surgery, patient data entry may include identification of the left hip or the right hip. Computer visual guidance system 125 can subsequently read this data. For example, a patient data file may include the hip type, and computer visual guidance system 125 obtains this information by accessing the patient data file. Alternatively, the left or the right hip can be ascertained by pre-operative software from a 3D image (e.g., CT, MRI) or 2D image (e.g., X-ray) and subsequently read by computer visual guidance system 125

6B. Light/Dark Side

Figure 29:
FIG. 29 is a schematic view showing one way of determining whether the X-ray image is of the left hip or the right hip.

X-ray technicians will usually rotate the C-arm image so that "up" on the image correlates to "superior" on the anatomy—if one assumes that this is true, then one can just look at the left and right sides of the beam cone to see which is darker on average. If the left side of the X-ray image is darker, then the image is of the left hip. If the left side of the X-ray image is lighter, then the image is of the right hip. This is because bone tissue absorbs X-rays and appears darker on the image. Air or soft tissue attenuates less X-rays, so they appear much lighter on the image. See FIG. 29, where the left side 165 of the X-ray image is darker and the right side 170 of the X-ray image is lighter.

The Light/Dark Side method is not useful if the C-arm image is not rotated so that "up" on the image correlates to "superior" on the anatomy.

6C: Using The Surgeon-Supplied Hints

Figure 30:
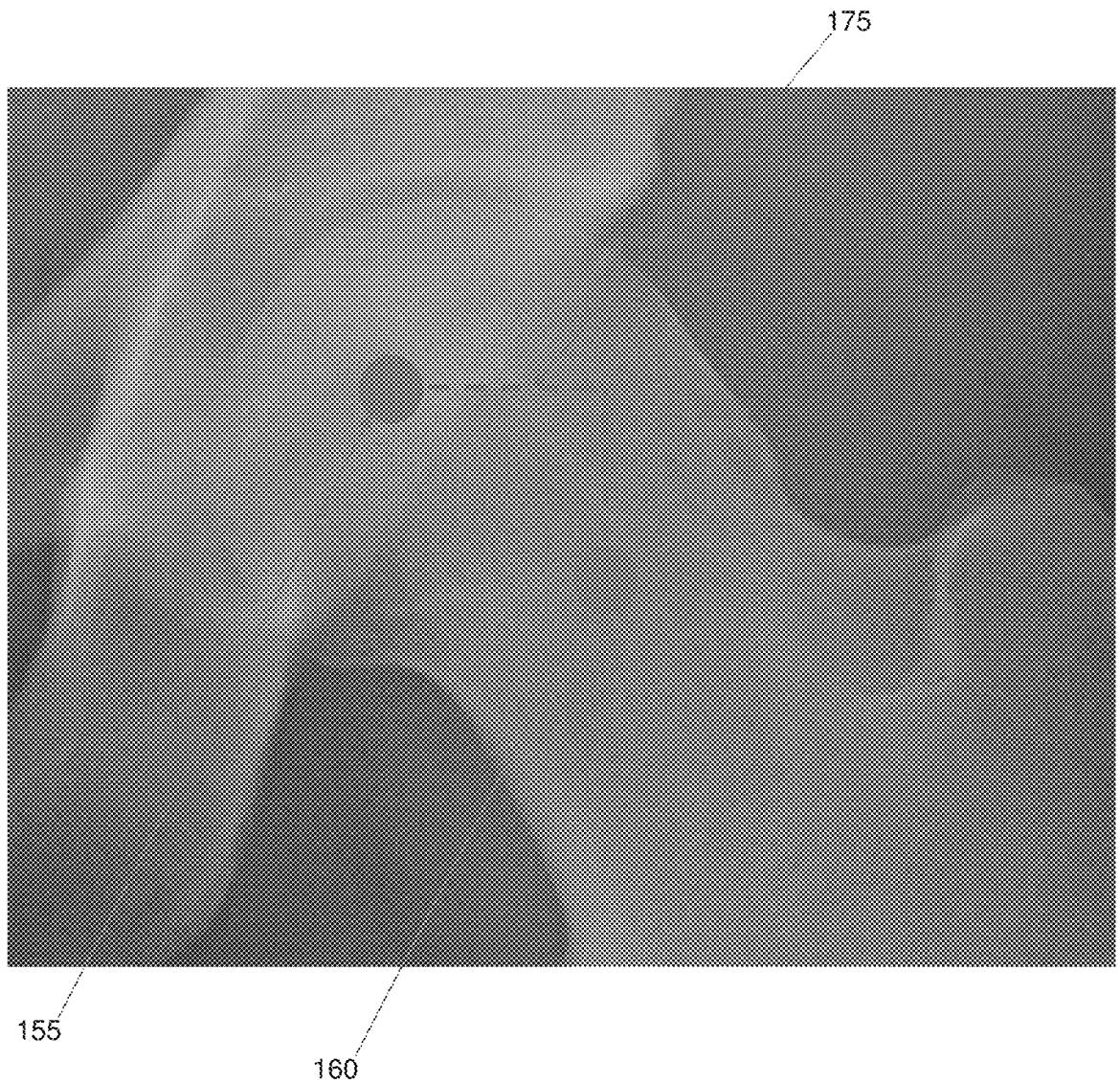
FIG. 30 is a schematic view showing how the surgeon-supplied "hints" may be used to determine whether the X-ray image is of the left hip or the right hip.

In one preferred form of the invention, femoral head hint 155 and femoral neck hint 160 are used to determine whether the X-ray image is of the left hip or the right hip. More particularly, and looking now at FIG. 30, the horizontal distance 175 from femoral head hint 155 and femoral neck hint 160 is determined. If femoral head hint 155 is to the left of femoral neck hint 160, the X-ray image is of the left hip, if femoral head hint 155 is to the right of femoral neck hint 160, the X-ray image is of the right hip.

6D: Instrument Position

In another form of the invention, if an instrument is in the X-ray image, computer visual guidance system 125 can use the location and orientation of the instrument to determine if the hip being imaged is a left hip or a right hip. Typically, instruments are introduced on the lateral side of the femoral head, with a trajectory from lateral to medial. Given this fact, computer visual guidance system 125 can first locate an instrument in the X-ray image, then identify the location and orientation of the instrument within the X-ray image so as to determine if the hip being imaged is a left hip or a right hip.

Step 7: Provide Clues For Where To Create The Search Area For Femoral Head

In the preferred form of the invention, the next step is to provide computer visual guidance system 125 with clues for where to start its analysis of the anatomy. This is desirable because processing will run faster if the analysis starts with an intelligent "guess" of the anatomy to center on.

There are multiple ways to provide clues for where to start.

7A. Center Of Search Area

In one approach, it is possible to simply use femoral head hint 155 (at the center of the femoral head) as the place to start the analysis.

7B. Tips Of Instruments

Figure 31:
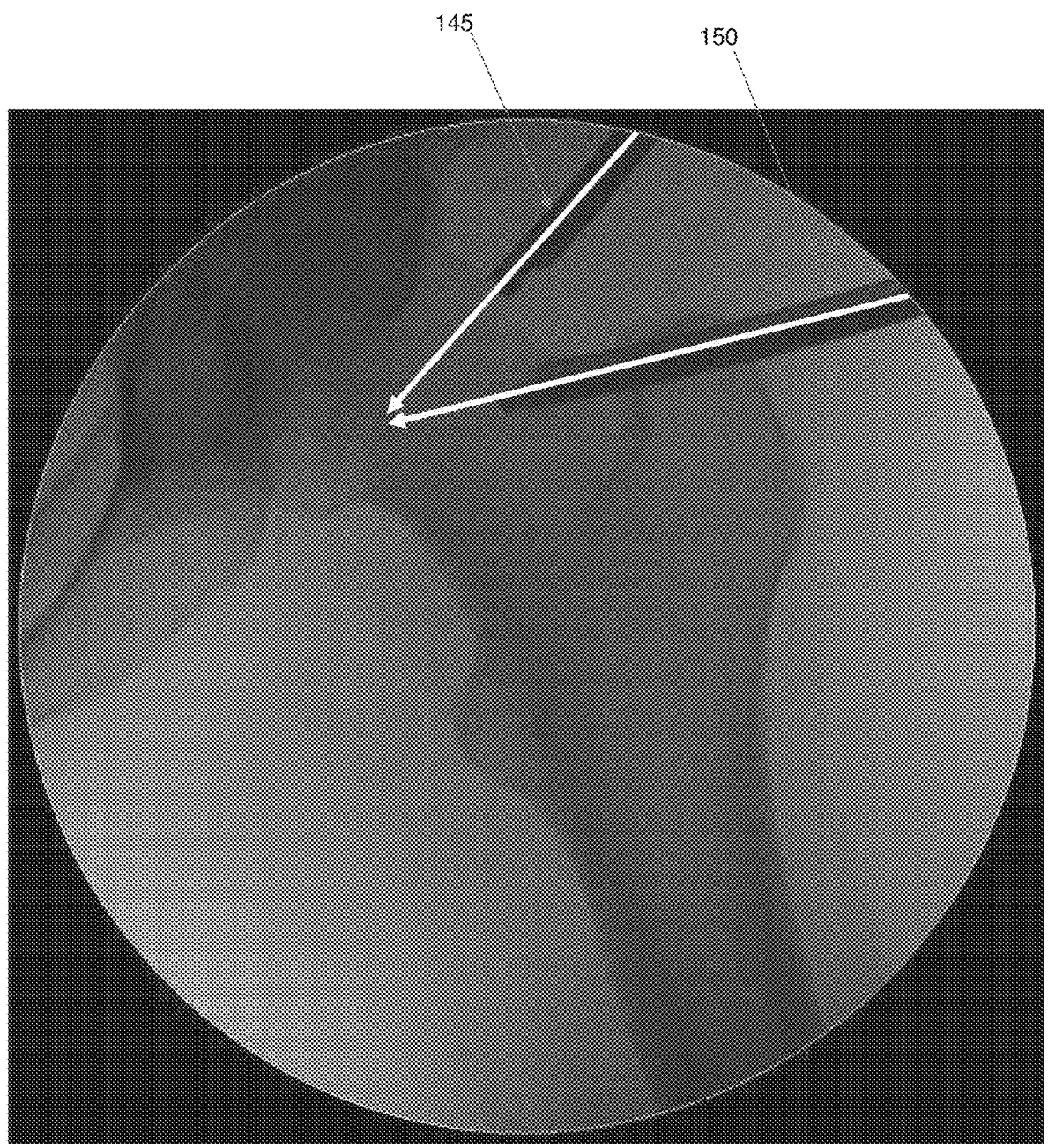
FIG. 31 is a schematic view showing one way for providing a clue of where to start the analysis of the anatomy.

Another way to intelligently guess where to start the analysis is to use the tips of the medical instruments present in the surgical field. Even if one does not know what the medical instruments are, they typically have an elongated shape and a Hough transform can be used to look for parallel lines (which indicate the profiles of the elongated medical instruments). The center of the femoral head will typically be somewhere near the tips of the medical instruments, at least within one diameter of the largest possible femoral head, and usually in front of the medical instruments. If two medical instruments are present in the X-ray image (there typically will be), then the estimate of where to start the analysis becomes more accurate, since one can limit the region of interest to the intersection of the parallel lines of the medical instruments (i.e., the side profiles of the medical instruments). See FIG. 31, where the tips of burr 145 and scope 150 are used to provide a clue as to where to start the analysis of the anatomy.

Step 8: Determine The Search Area For Femoral Head

In the preferred form of the invention, the next step is to determine the search area. This is desirable because the more pixels that computer visual guidance system 125 has to look at, the longer the search time. So anything that can reduce the search area will speed up processing time.

Figure 32:
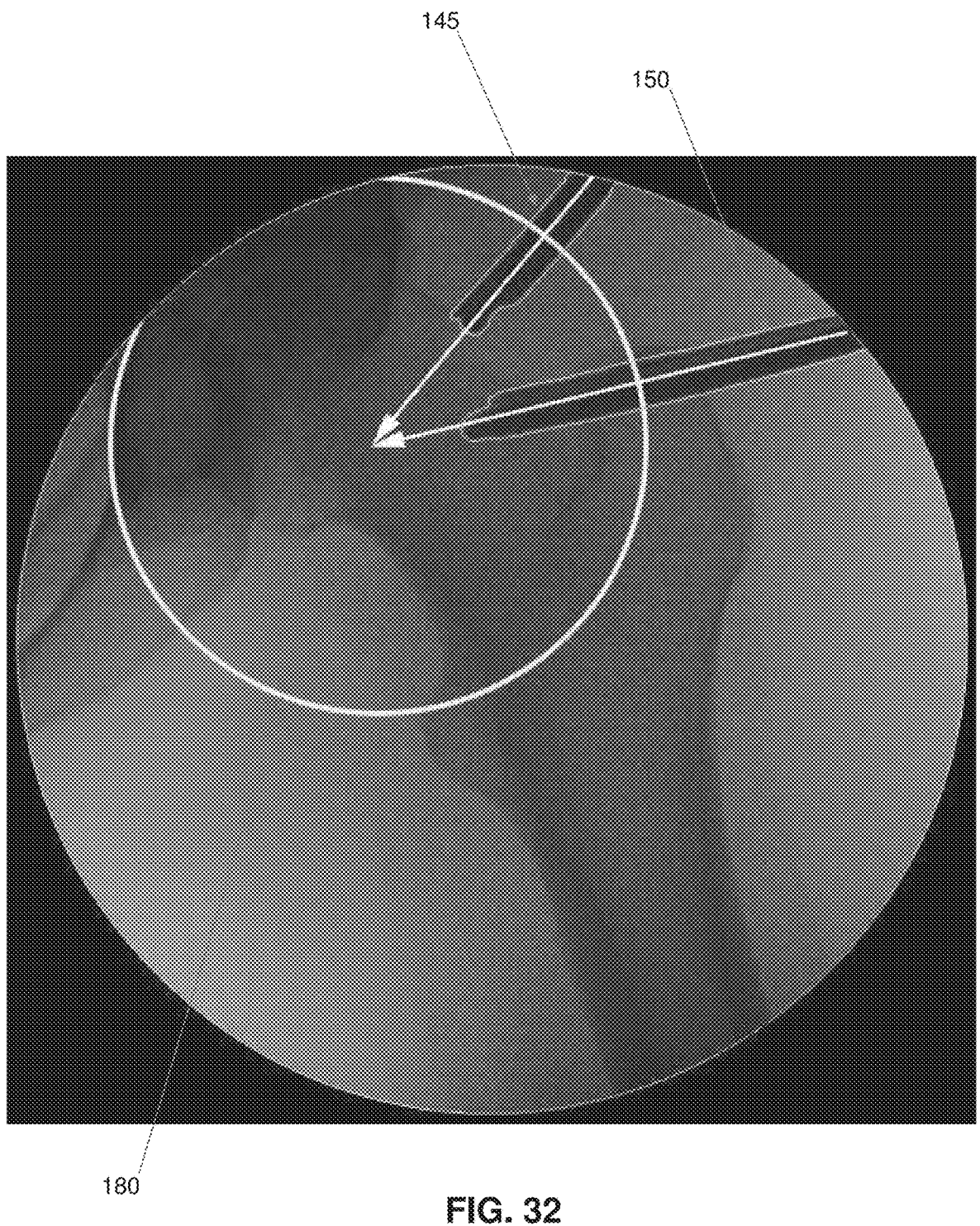
FIG. 32 is a schematic view showing one way for determining the search area.

There are multiple ways to determine the search area. In one preferred form of the invention, the image area outside the beam cone is eliminated. Most C-arms provide a circular image on a black background. This is because the beam of X-rays is arranged in a cone, and is received by a circular image intensifier. It is not necessary to search the black areas of the X-ray image. In fact, it can be assumed that the femoral head will be mostly, if not entirely, inside the beam cone of the X-ray image. It is possible, therefore, to narrow the search for the femoral head to those structures that have a center point well inside the beam cone. A search area is defined around the clue from Step 7. See FIG. 32, where a search area 180 is shown defined around the clue from Step 7.

Step 9: Conduct Edge Detection

Figure 33:
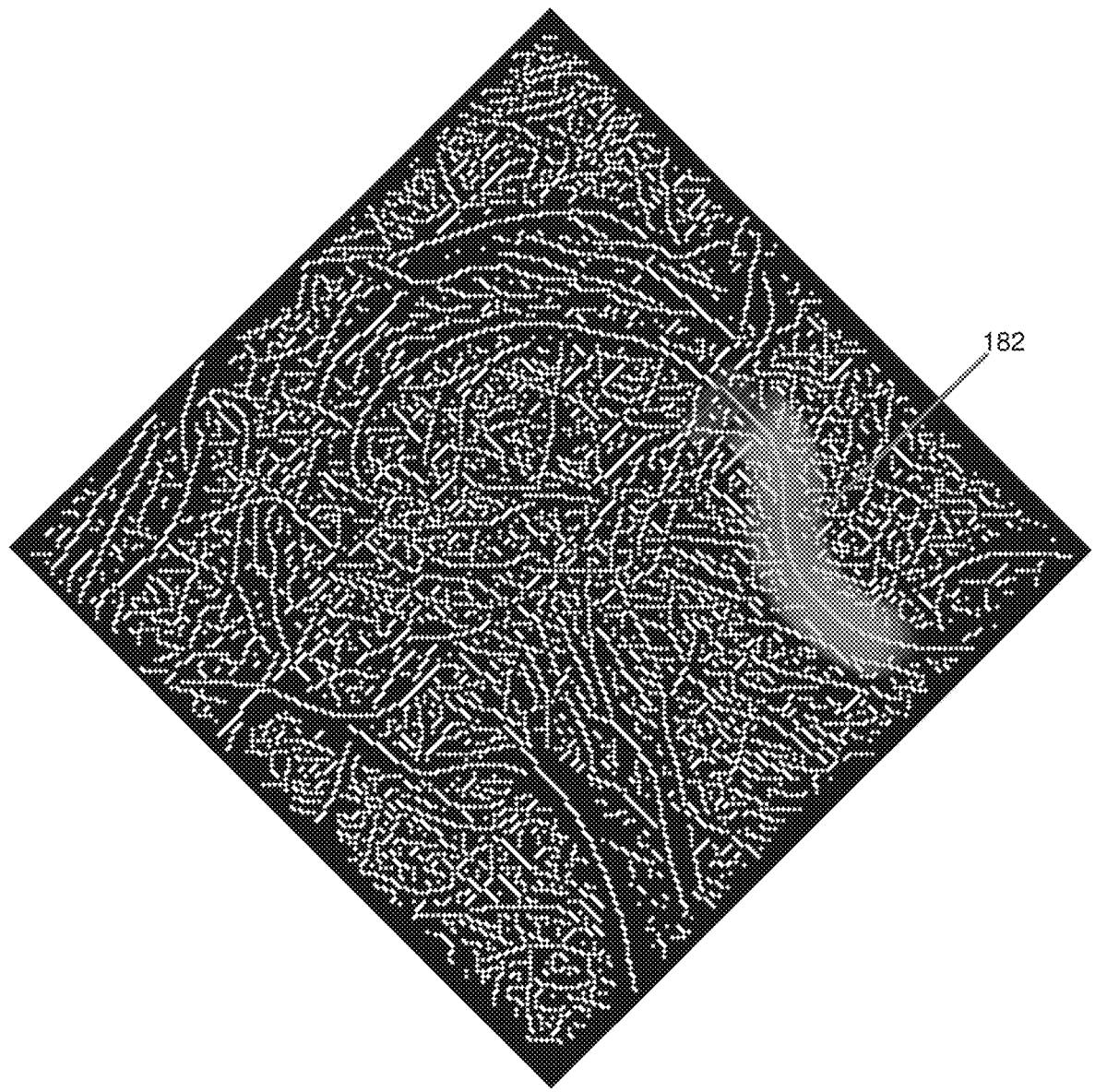
FIG. 33 is a schematic view showing edge detection.

In the preferred form of the invention, the next step is to conduct edge detection of the relevant anatomy to determine the edges of the femoral head. There are multiple ways to carry this out including industry standard methods such as canny edge detection. See FIG. 33, which shows edge detection for the femoral head.

Step 10: Find/Remove Instrument Edges

After edge detection has been effected, it is desirable to find and remove the edges of any instruments that are in the search area, since the presence of instrument edges in the image can complicate subsequent processing steps (e.g., finding the femoral head, finding the femoral neck, etc.). Finding and removing instrument edges may be effected in ways well known in the art of image processing.

Step 11: Find The Femoral Head

In the preferred form of the invention, the next step is to find the femoral head. There are multiple ways to find the femoral head.

11A. Hough Transform

Figure 33A:
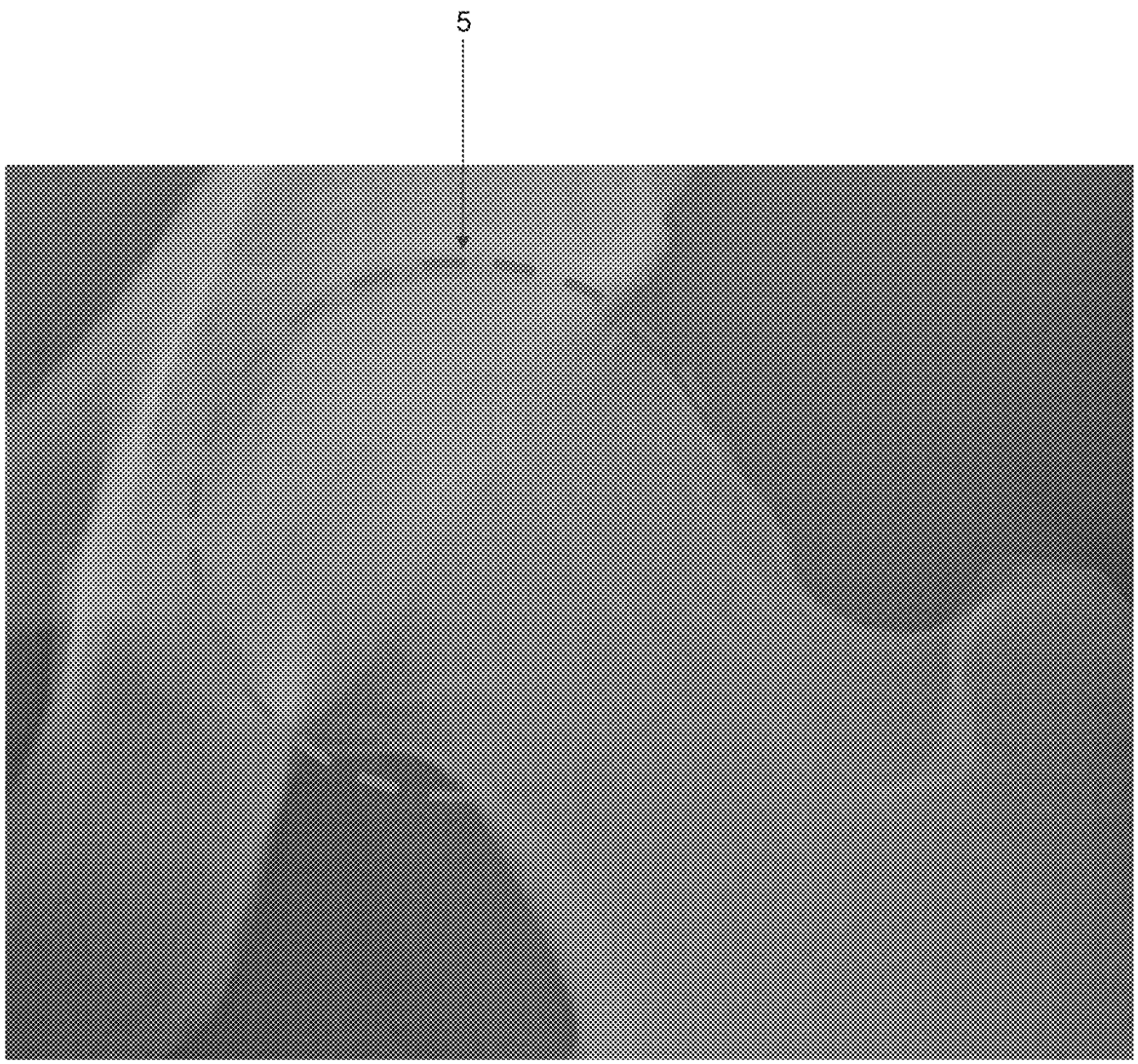
FIG. 33A is a schematic view showing estimation of the femoral head.

The simplest method to find the femoral head is to use a Hough transform, looking for circles. These circles are limited in the range of the smallest and largest possible femoral heads. The Hough transform produces a list of possible answers and the best possible answer is selected. This method works well in high quality images, although it can fail in low quality images. See FIG. 33A, which shows circle 5 encircling the femoral head.

11B. Ray Tracing

One problem with the aforementioned Hough transform approach is that it is looking for circles that perfectly overlap with edges in the X-ray image. In some cases, there is almost no perfect circle in the X-ray image, especially with poor image quality and a large cam pathology.

Therefore, in another approach, a center point is picked, and then computer visual guidance system 125 starts tracing along lines looking for edges between the minimum and maximum possible radii (which correlates to the smallest and largest possible femoral head). In this approach, computer visual guidance system 125 selects the point that has the strongest edge in each ray, and then checks to see if these points end up in a circle. Then another point is selected, and the process is repeated. This is done iteratively until the best point is found, using previous points as a guide for where to look next.

This approach can be further improved in the following ways:
- perform a radial blur at each point before running edge detection—this will obscure hard edges that are not circles;
- look for strong edges, and check their gradients to see if they are dark→light (femoral head) or light→dark (acetabulum); and
- look for partial circles, rather than full circles—the correct outline of the femoral head will not have an edge where the femoral neck connects to the femoral head.

11C. Active Shape Modeling (ASM)

Figure 34:
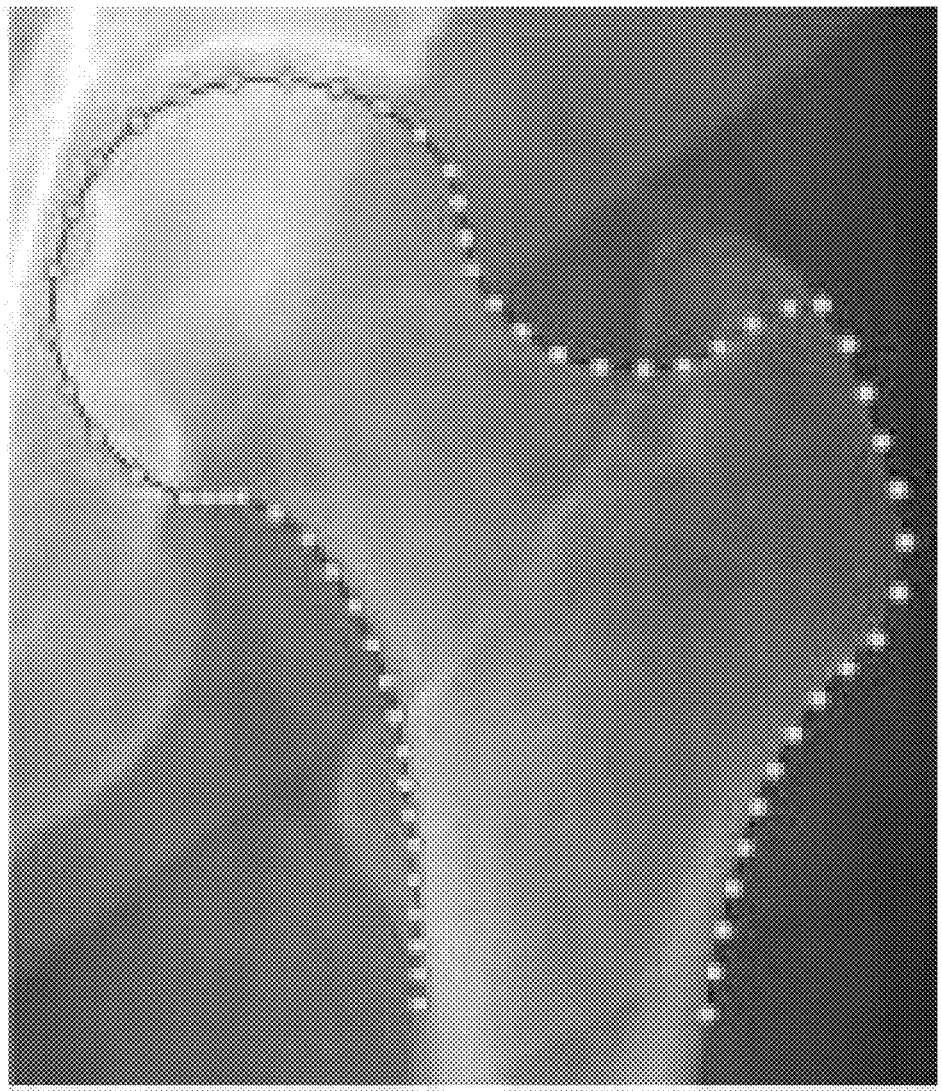
FIG. 34 is a schematic view showing another way for finding the femoral head.

In Active Shape Modeling (ASM), computer visual guidance system 125 is trained with hundreds (or thousands) of hip X-ray images, where dozens of specific locations are selected around the profile of the femoral head. Then computer visual guidance system 125 is presented with a new X-ray image and a "good guess" as to where the femur is in that image. This "good guess" does not have to be highly accurate, it simply needs to be in the right ballpark. Step 7 (provide clues where to start) must be completed for this approach to be used. Once computer visual guidance system 125 has the image and the "good guess" of where to start, the ASM process will overlay a set of points in the shape of a femur and then work to reduce the error between the set of points and the strong edges in the image. See FIG. 34. Once the ASM process is completed by the computer visual guidance system, one can just select the specific points from the femur and calculate a best-fit circle for the femoral head.

Step 12: Find the Femoral Neck and its Mid-Line

In the preferred form of the invention, the next step is to find the femoral neck and its mid-line. There are multiple ways to find the femoral neck and its mid-line.

12A. Box Sweep

It is generally easier to find the femoral neck once the femoral head has been identified. With the Box Sweep method, computer visual guidance system 125 sweeps a box around the femoral head (where the box has its mid-line passing through the center of the femoral head) and looks to see if the sides of that box line up with the edges of the femoral neck (edge detection is used to identify the edges of the femoral neck). This is repeated for boxes of multiple sizes. The box that lines up with the strongest edges of the femoral neck is chosen. The center of the box is then used to determine the mid-line of the femoral neck.

12B. Active Shape Modeling (ASM)

This approach works in a manner similar to how ASM is used to find the femoral head, except that one selects the points on the femoral neck, then determines a mid-line, and then finds the average location of those points to determine the mid-line of the femoral neck.

Step 13: Find Where The Femoral Neck Stops Being Round And The Cam Pathology Starts In the preferred form of the invention, the next step is to find where the femoral head stops being round and the cam pathology starts.

Figure 35:
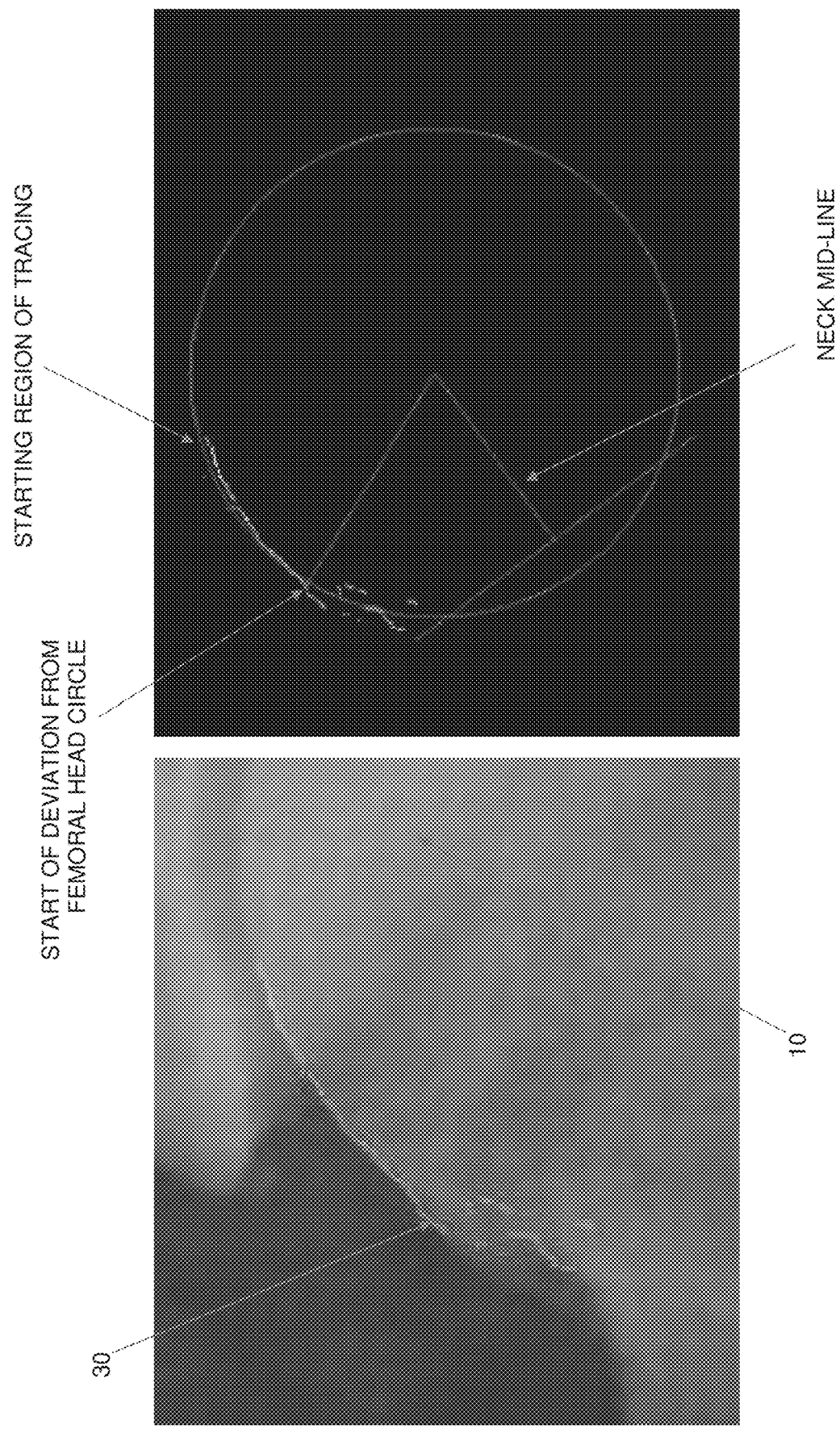
FIG. 35 is a schematic view showing one way for finding where the femoral neck stops being round and the cam legion starts.

In one preferred approach, the strongest edges (e.g., as shown at 182 in FIG. 33) of the bone surface are traced (e.g., using the results of edge detection) until a deviation from the circle around the femoral head is found. As the region of interest is known, the tracing does not need to include the entire femoral head but rather just the region of interest. In one preferred embodiment, the region of interest starts at a location on the femoral head which is approximately 110 degrees from the femoral neck mid-line in the superior direction (in other words, for a right hip as shown in FIG. 35, between the 9 o'clock position and the 12 noon position). In identifying a deviation, a threshold level for the deviation can be used to ignore small deviations which may be a result of imperfections in edge detection rather than being the actual cam pathology. In one preferred embodiment, the deviation threshold is a small percentage of the femoral head diameter, for example, 3-6% of the femoral head diameter, and more preferably 4% of the femoral head diameter. In another embodiment, the deviation threshold is a fixed value, for example, 0.5-2 mm, and more preferably 1 mm. In this embodiment, it is preferable to have calibrated the pixels of the image, so that the relative pixel size to the size of the anatomy is known. See FIG. 35.

Step 14: Measure The Alpha Angle And Input The Target Alpha Angle

In the preferred form of the invention, the next step is to measure the Alpha Angle.

Figure 36:
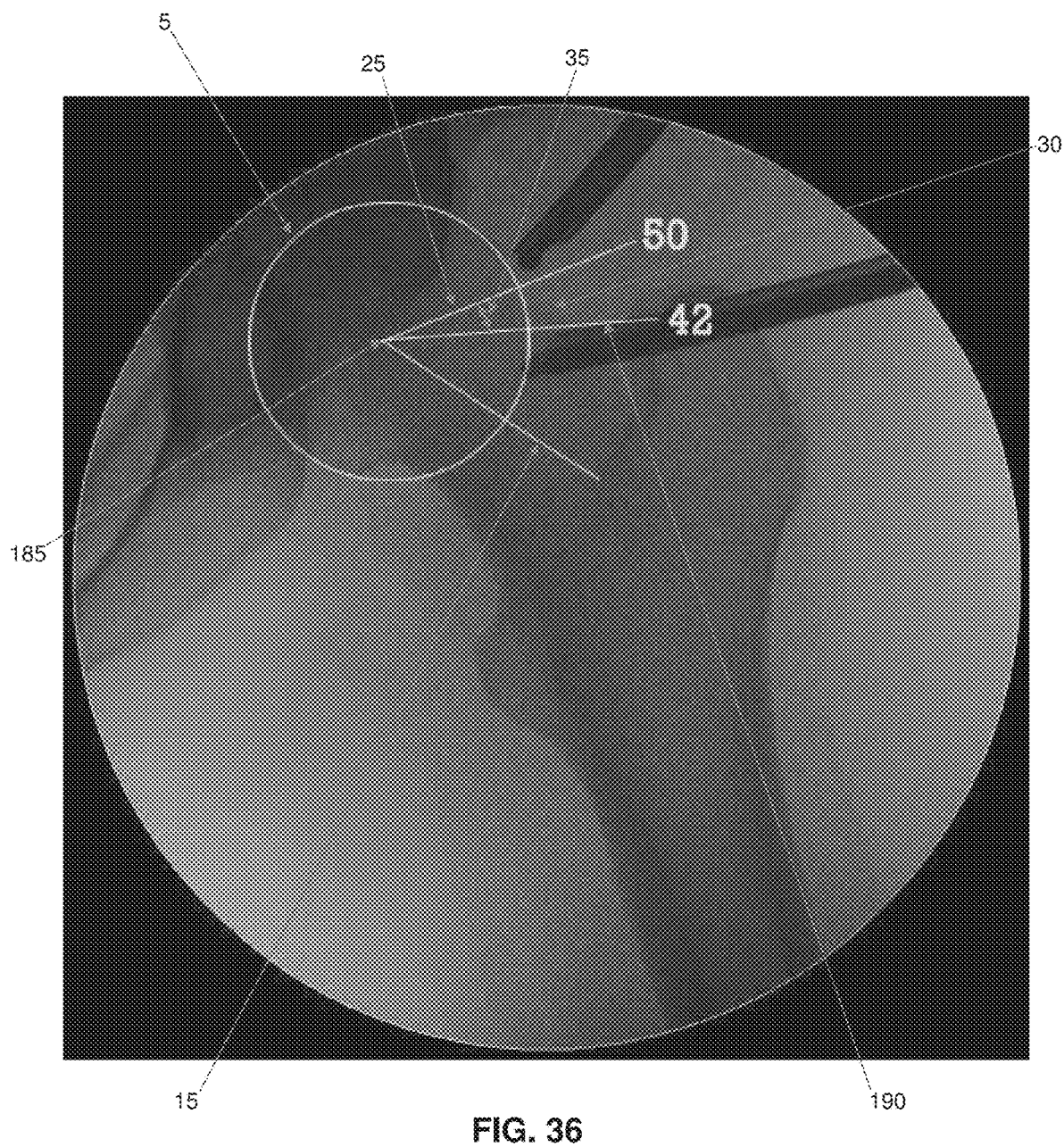
FIG. 36 is a schematic view showing one way of measuring the Alpha Angle and for drawing extra features on the X-ray image.

As seen in FIG. 36, the Alpha Angle 35 is calculated as the angle between these image features:

the center line 15 of the femoral neck;

the center point 185 of the femoral head; and the location of the start of the cam pathology 30 at the femoral head/neck junction.

In other words, the Alpha Angle is the angle measured between (i) the line 15 originating at the center of the femoral head and extending along the center of the femoral neck, and (ii) the line 25 originating at the center of the femoral head and passing through the location at the start of the cam pathology.

This Alpha Angle can be annotated onto the X-ray image, as shown in FIG. 36, along with circle 5 enscribing the femoral head and line 15 showing the center of the femoral neck, and this annotated X-ray image can be presented to the surgeon on computer visual guidance system 125 or monitor 110.

The surgeon may also find it useful to know the size of the cam pathology by way of the angle subtended between the Alpha Angle and the target Alpha Angle (i.e., the desired Alpha Angle). The target Alpha Angle is established, either with input from the surgeon or another source. The computer visual guidance system 125 then displays the target Alpha Angle (line 190 in FIG. 36). The greater the difference between the current Alpha Angle line 25 and the target Alpha Angle line 190, the larger the cam pathology and hence more bone removal is required. See FIG. 36, where the target Alpha Angle of 42 degrees is presented as line 190 on the X-ray image, along with the actual Alpha Angle line 25, circle 5 enscribing the femoral head, and line 15 showing the center of the femoral neck.

Step 15: Compute The Resection Curve

Figure 37:
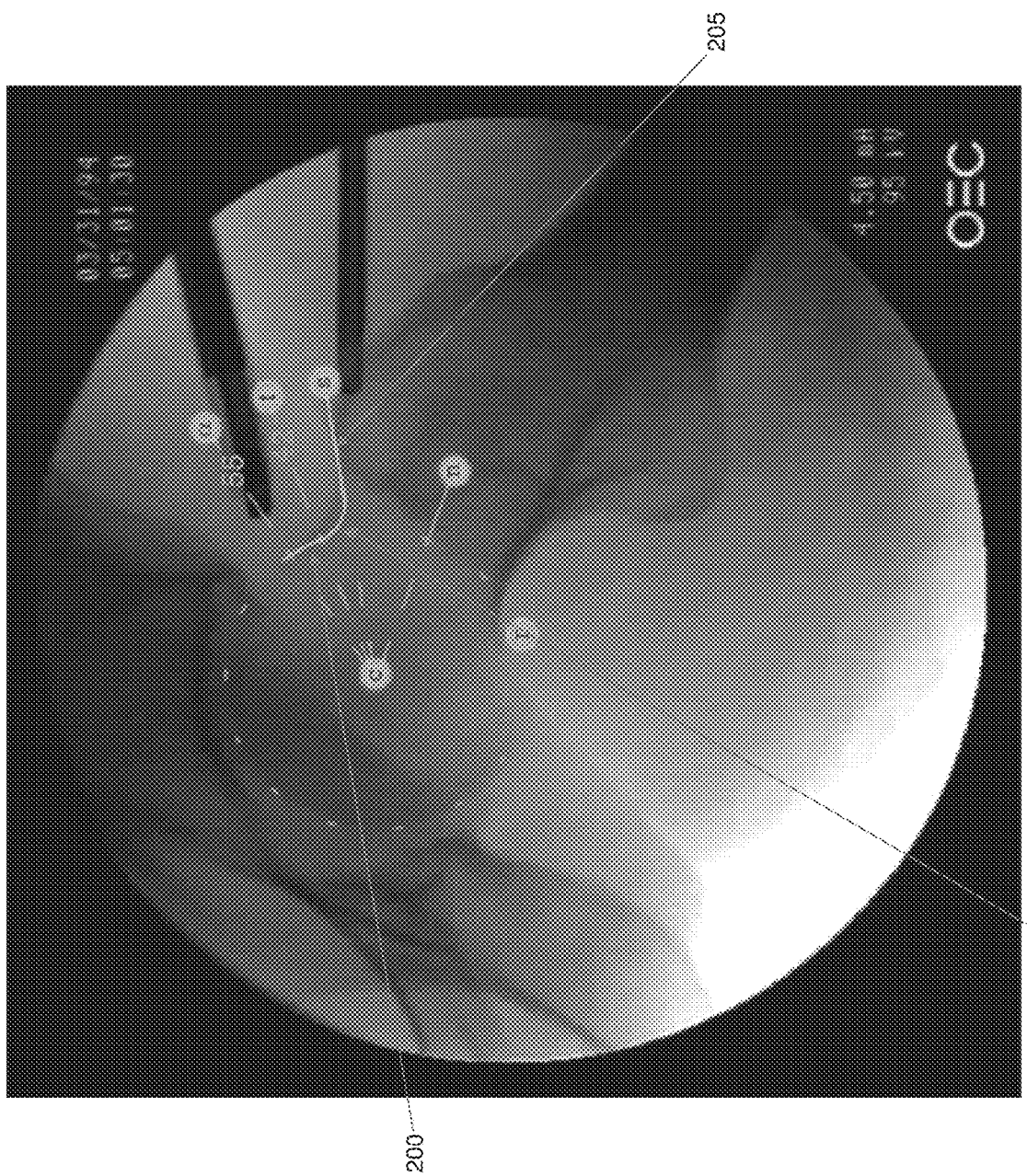
FIG. 37 is a schematic view showing the resection curve for treating cam-type femoroacetabular impingement.

Looking now at FIG. 37, the resection curve 195 comprises a first resection curve 200 adjacent to the femoral head, and a second resection curve 205 adjacent to the femoral neck.

First resection curve 200 starts at the Alpha Angle Line 25 and ends at the target Alpha Angle line 190. Note that first resection curve 200 is simply the continuation of the circle of the femoral head.

Second resection curve 205 starts at the end of first resection curve 200 (i.e., at the target Alpha Angle line 190) and extends down the neck.

Figure 38:
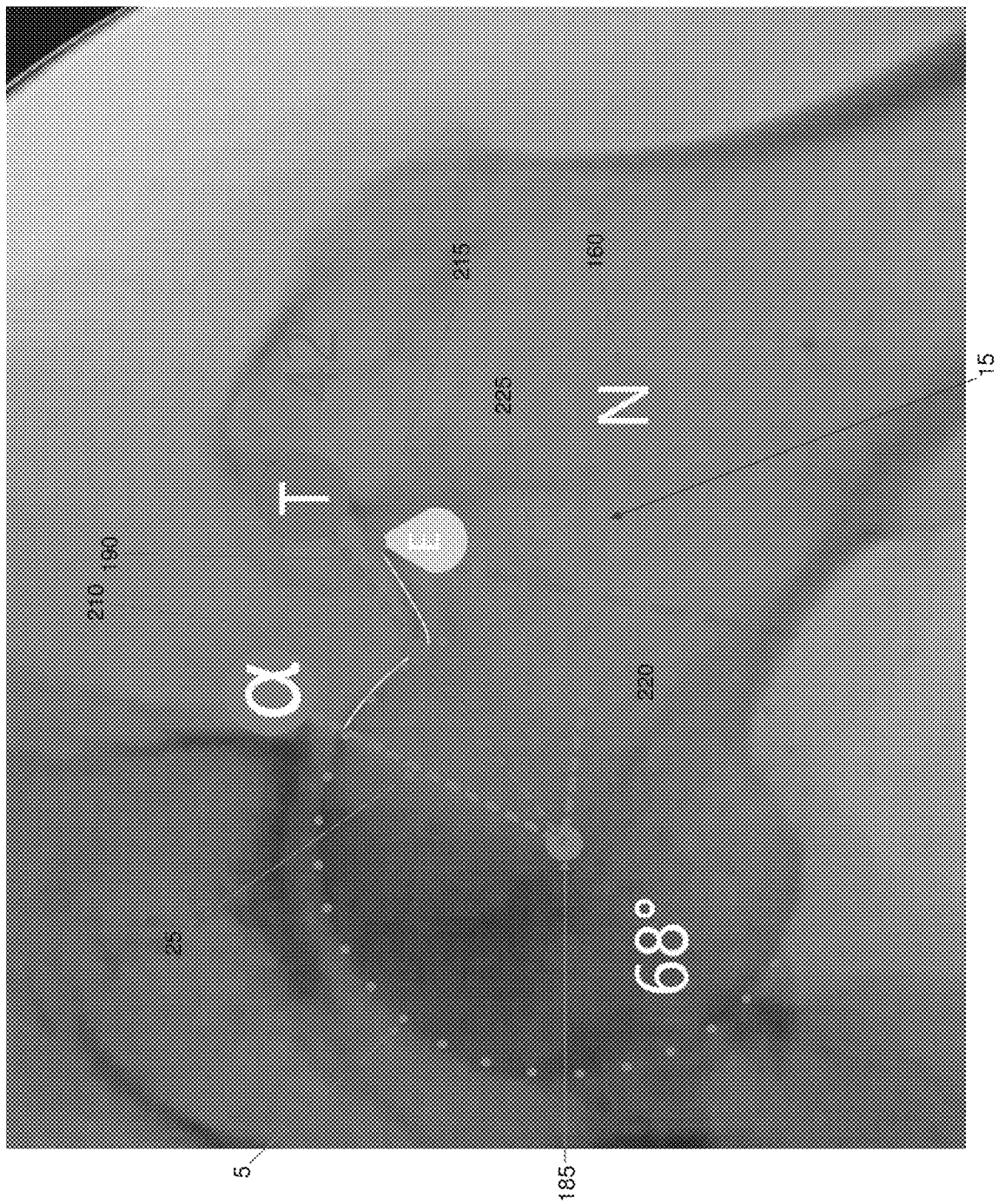
FIG. 38 is a schematic view showing another way of drawing extra features on the X-ray image.

In the preferred form of the invention, second resection curve 205 is calculated as follows. First, and looking now at FIG. 38, the start point 210 and end point 215 of second resection curve 205 are found. As seen in FIG. 38, start point 210 is the point at which target Alpha Angle line 190 intersects the femoral head circle. Note that start point 210 is also the endpoint of first section curve 200. In one embodiment, end point 215 is found by determining the shortest distance between femoral neck hint 160 and the neck boundary: this shortest line of intersection defines end point 215. Then a spline 220 is generated, using start point 210, end point 215 and a control point 225 for spline 220. Note that spline 220 is second resection curve 205. Control point 225 for spline 220 may be generated in a variety of ways. By way of example but not limitation, control point 225 may be obtained by studying a set of "normal" patient anatomies and determining an appropriate control point for a given start point 210 and a given endpoint 215 in order to provide a spline approximating a normal anatomy. Or control point 225 may be obtained by polling a group of experts to determine an appropriate control point for a given start point 210 and a given endpoint 215 in order to provide a spline approximating a normal anatomy. In any case, after start point 210, end point 215 and control point 225 have been determined, spline 220 (i.e., second resection curve 205) is generated and displayed with the X-ray image.

In essence, second resection curve 205 is concatenated to the end of first resection curve 200 so as to produce the overall resection curve 195.

16. Measure Depth Of Resection

If desired, the depth of resection (i.e., the thickness of bone to be removed) can also be measured and then displayed to the user, using the calibrations of pixel size previously conducted.

17. Display

In one preferred form of the invention, and still looking now at FIG. 38, the following features are presented on the X-ray image:

circle 5 inscribing the femoral head;

centerpoint 185 of the circle inscribing the femoral head;

line 15 originating at the center of the femoral head and extending along the centerline of the femoral neck;

Alpha Angle line 25 originating at the center of the femoral head and passing through the location at the start of the cam pathology;

line 190 showing the target Alpha Angle; and resection curve 195.

If desired, the numeric value of the Alpha Angle can be presented on the X-ray image (see, for example, FIG. 37 where the numeric value of "55" is placed on the X-ray image to show that the Alpha Angle is 50 degrees), and the numeric value of the target Alpha Angle can be presented on the X-ray image (see, for example, FIG. 37 where the numeric value "42" is placed on the X-ray image to show the target Alpha Angle is 42 degrees).

In the preferred form of the invention, the next step is to draw extra features on the X-ray image.

17A. Ruler

Figure 39:
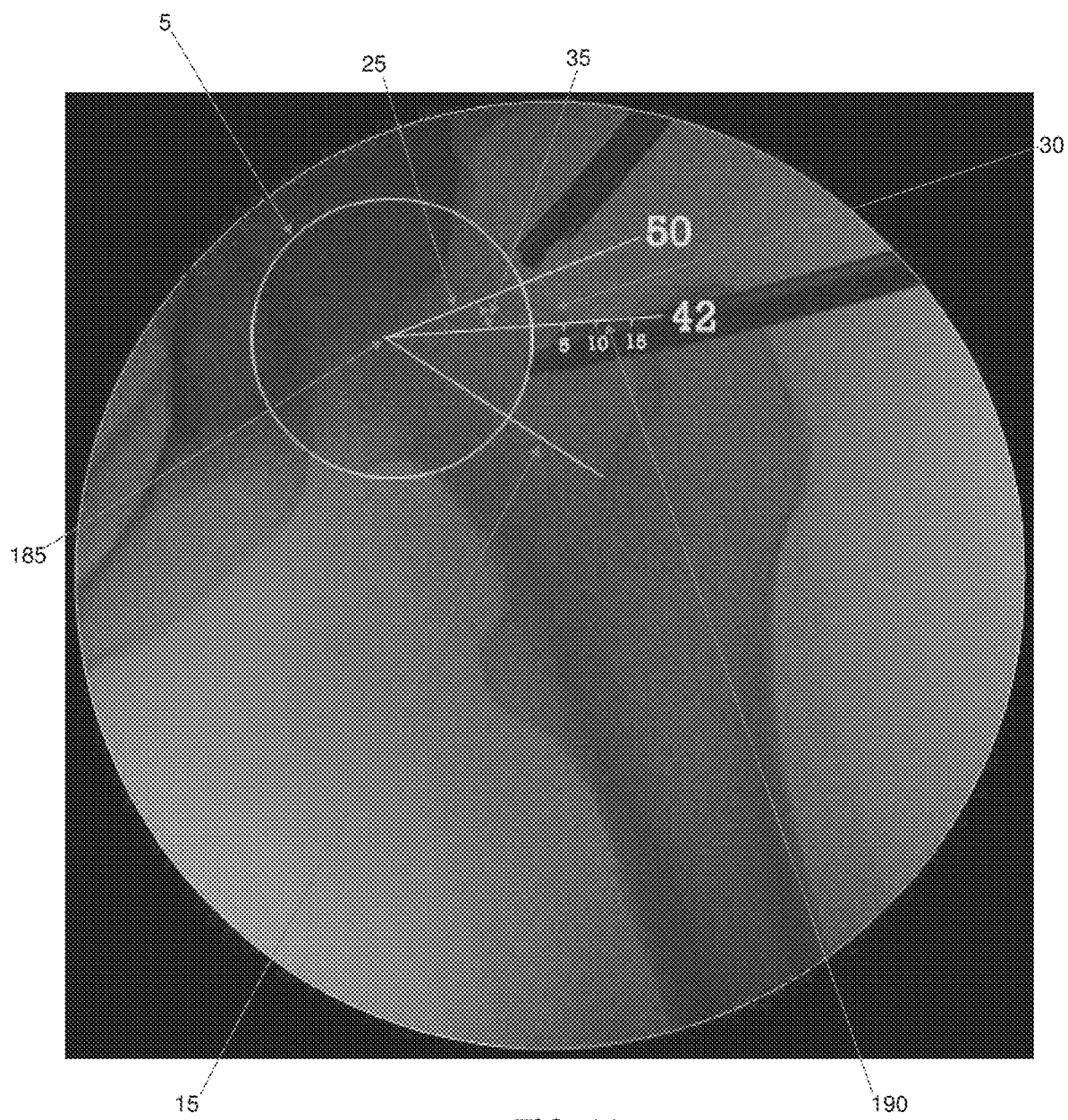
FIG. 39 is a schematic view showing one way of drawing extra features on the X-ray image.

Surgeons may desire to know the size of the cam pathology, so it can be useful to add a ruler to the image. Pixel calibration is needed for this feature, since the ruler needs to identify the "real-world" size of the cam pathology. In one preferred form of the invention, computer visual guidance system 125 is configured to draw the ruler just below the cam pathology, which will show the surgeon how much bone they have to remove. See FIG. 39.

17B. False Color 2D Cam Pathology

Figure 40:
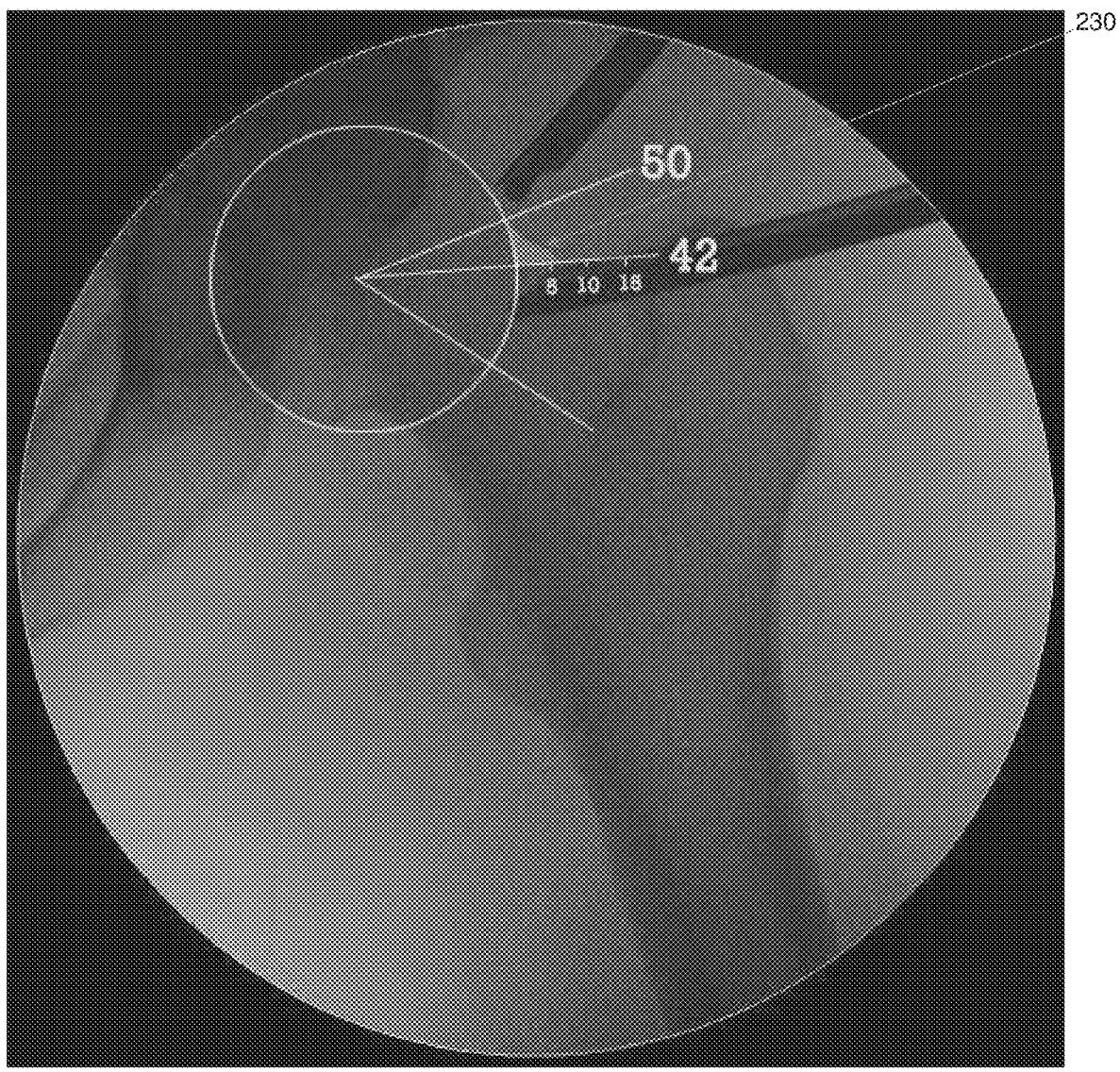
FIG. 40 is a schematic view showing another way of drawing extra features on the X-ray image.

When computer visual guidance system 125 draws the target line for the target Alpha Angle, computer visual guidance system 125 can add false color to the triangular region 230 (FIG. 40) denoting the cam pathology which is to be removed (i.e., the bone which is located between the start of the cam and the target Alpha Angle).

In one form of the invention, multiple C-Arm images (e.g., with the C-arm manipulated through a number of planes) can be acquired and the computer system can generate the false color 3D cam pathology as a resulting set of false color 2D cam pathology images displayed at the same time for the surgeon.

Figure 41:
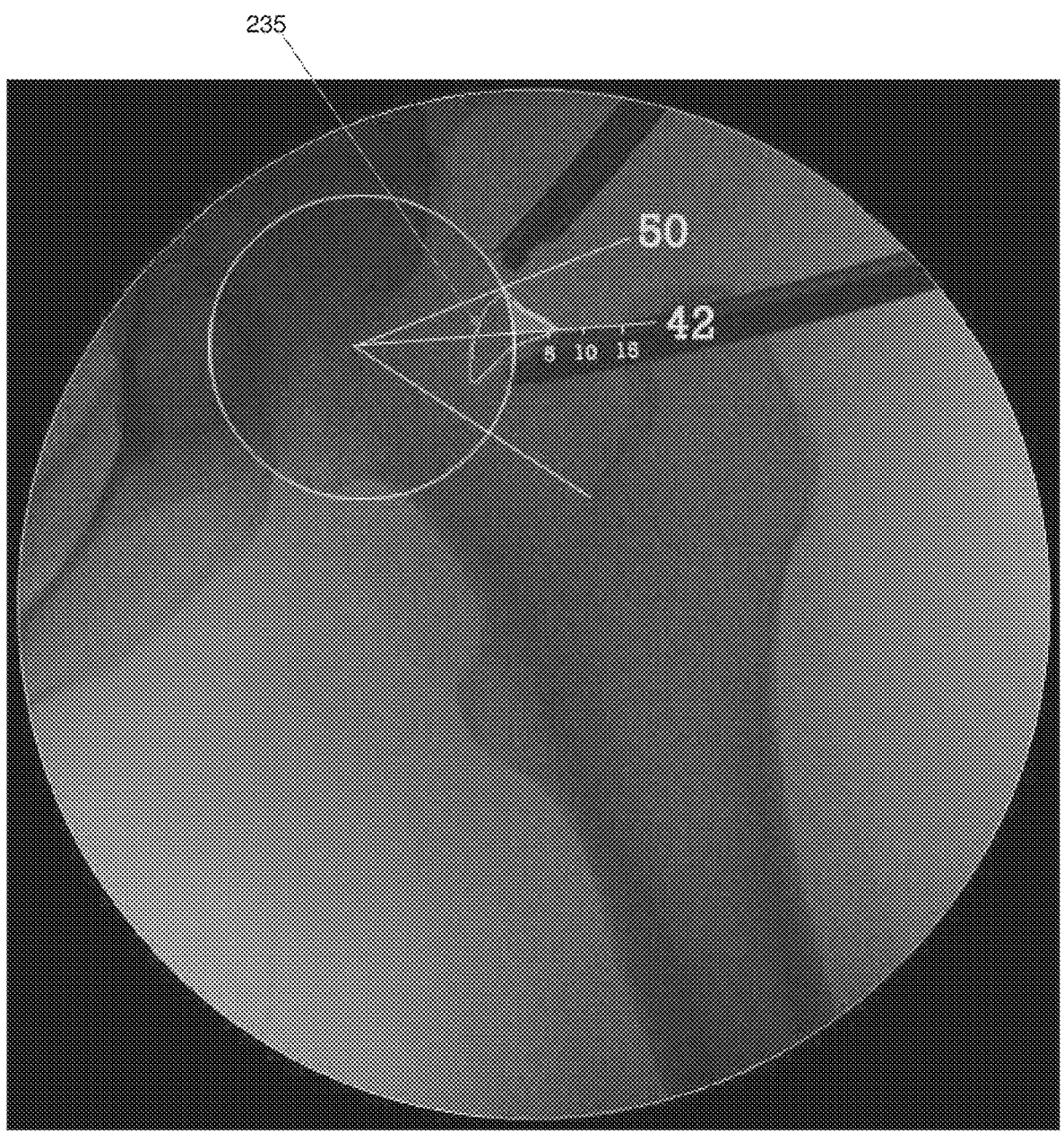
FIG. 41 is a schematic view showing another way of drawing extra features on the X-ray image.
Figure 42:
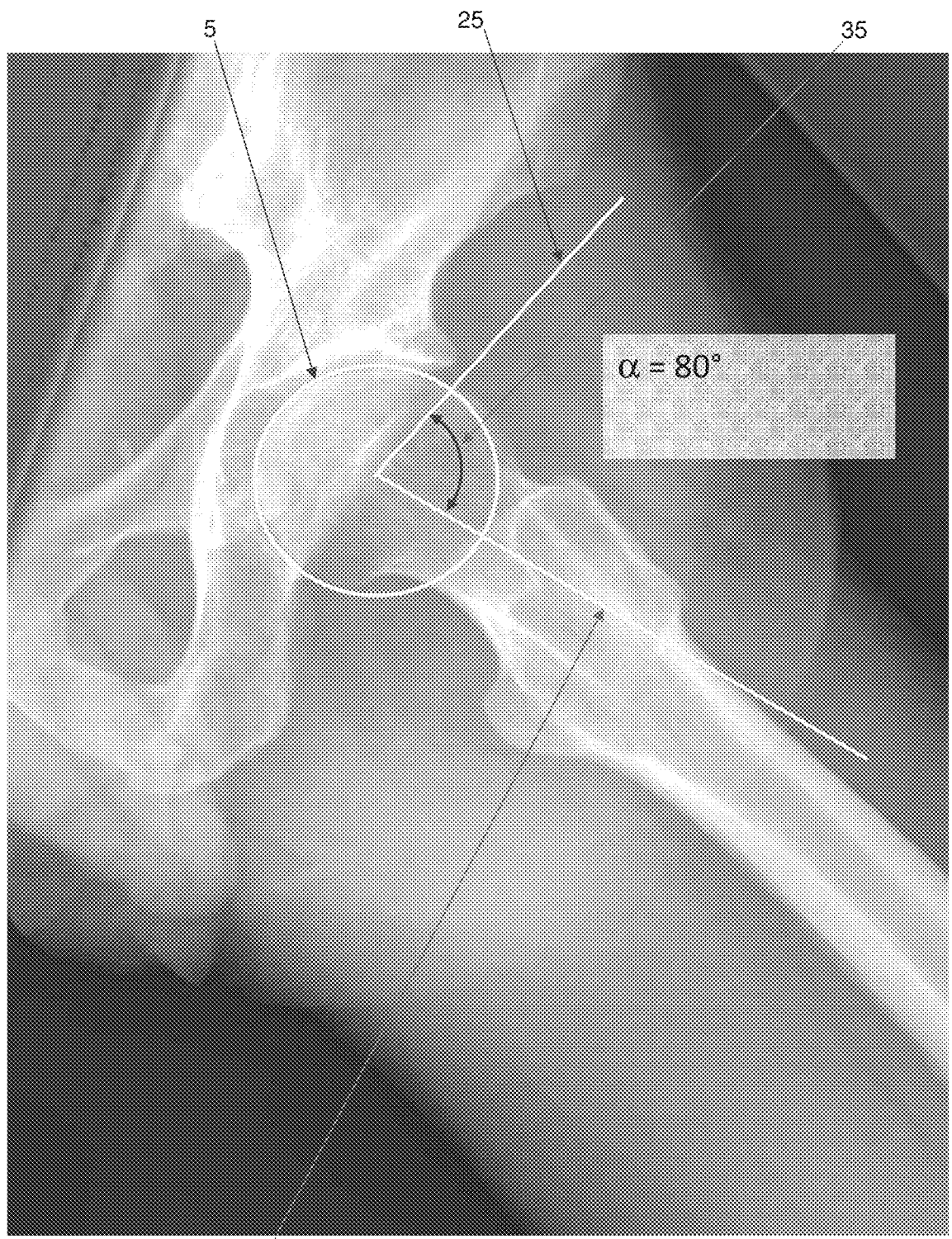
FIGS. 42-44 is a series of schematic views showing Alpha Angle recalculations to track progress during the resecting of a cam pathology.
Figure 43:
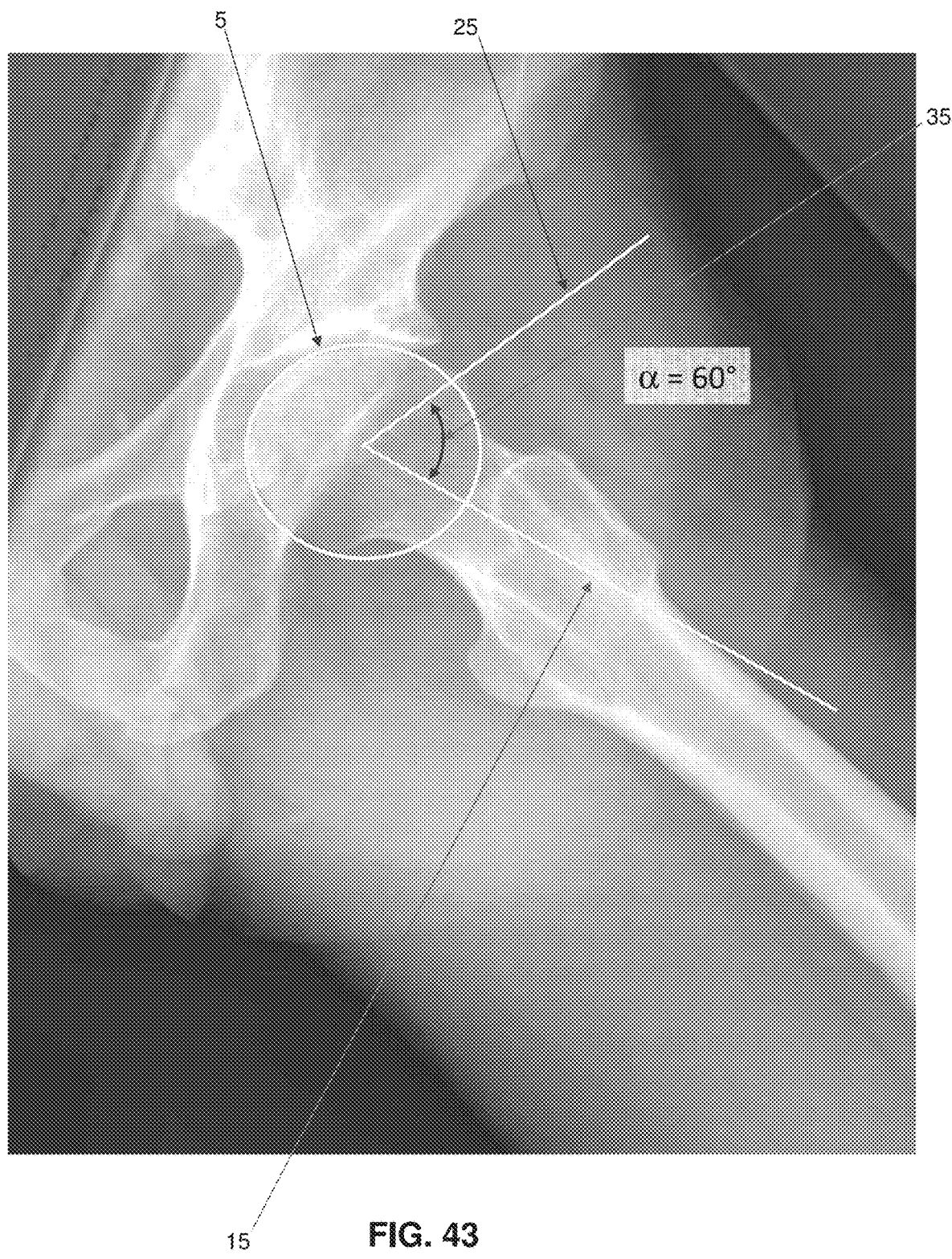
Figure 44:
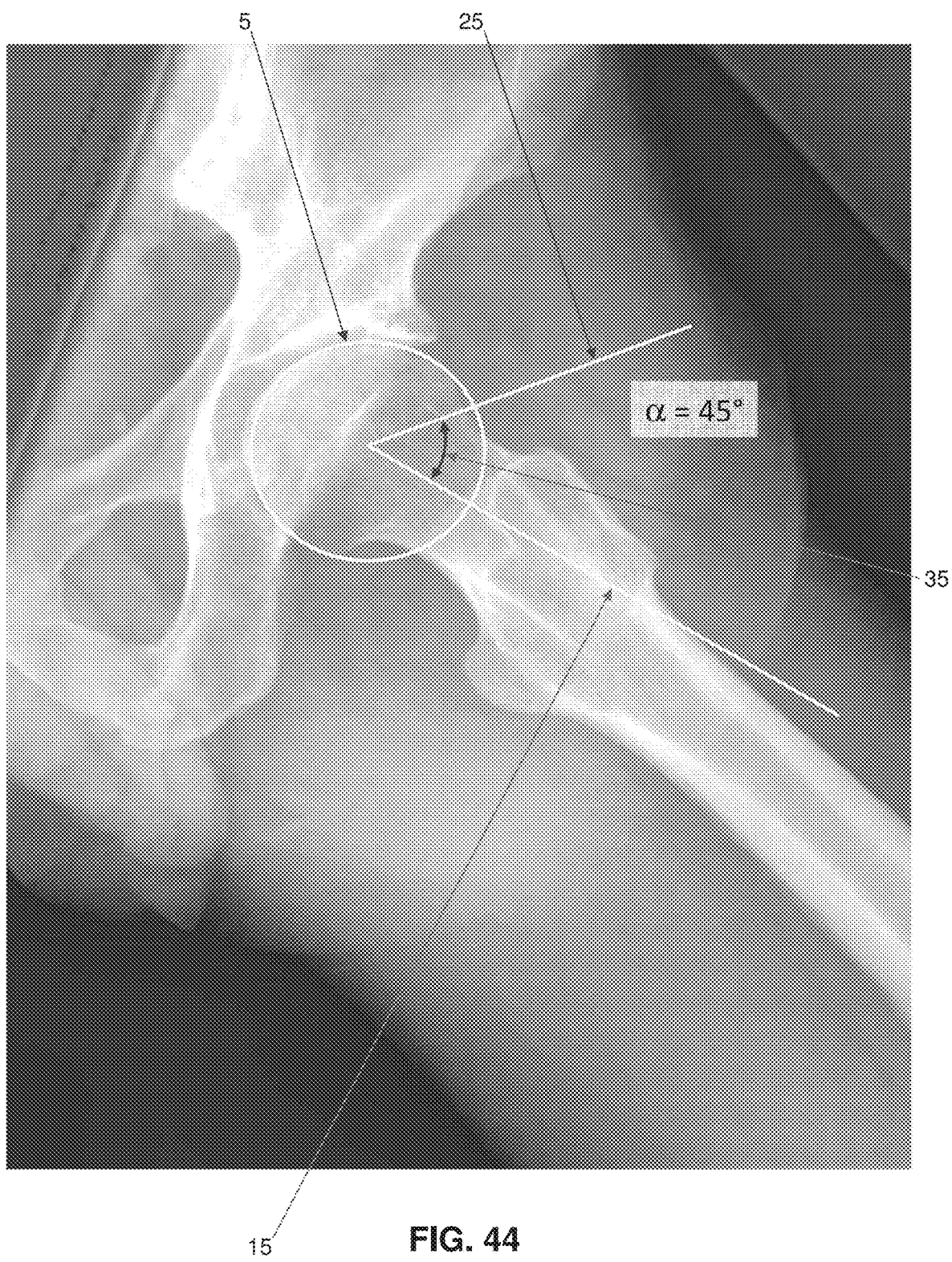
Figure 45:
FIGS. 45-47 is a series of schematic views showing Alpha Angle recalculations to track progress during the resecting of a cam pathology.
Figure 46:
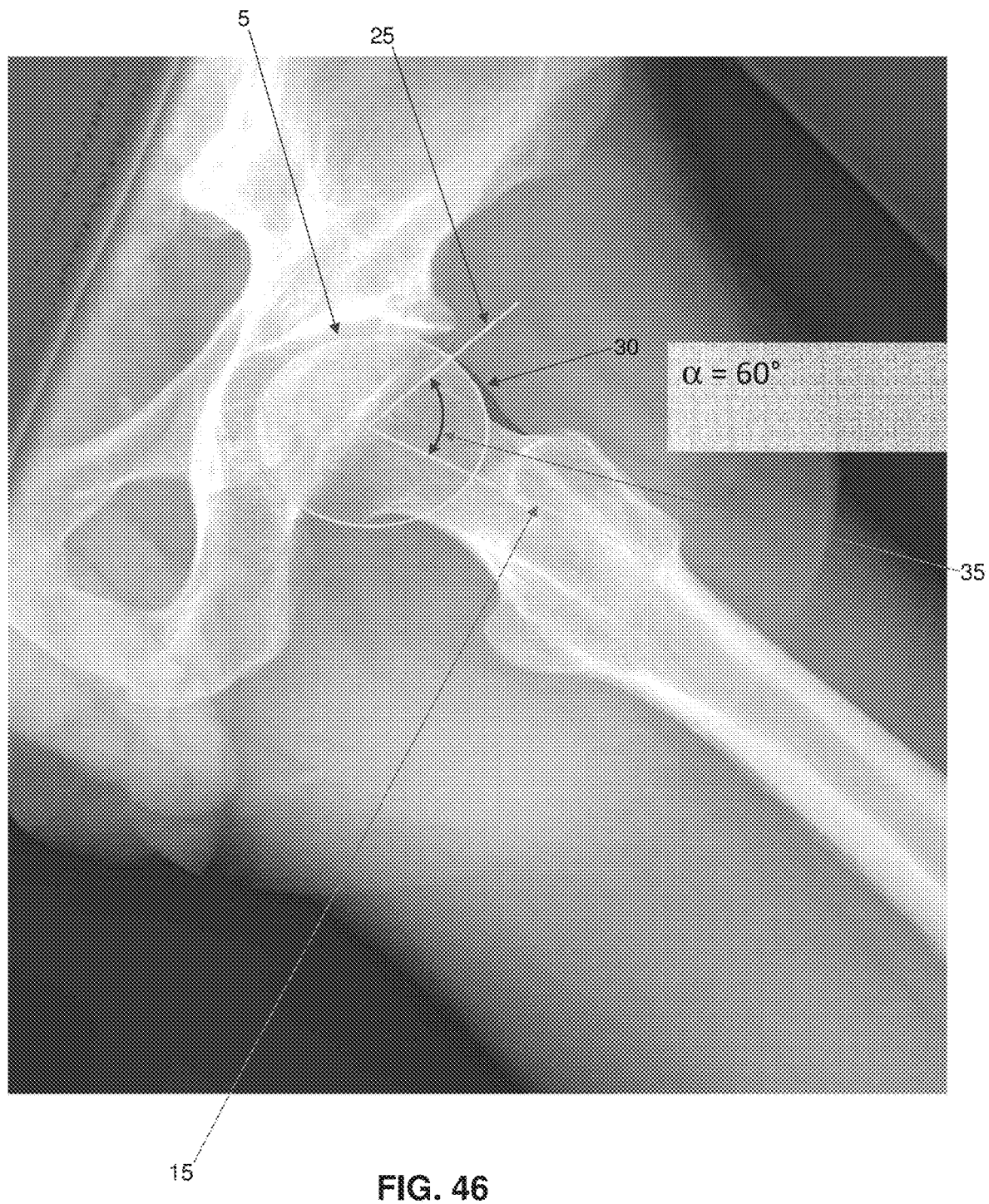
Figure 47:
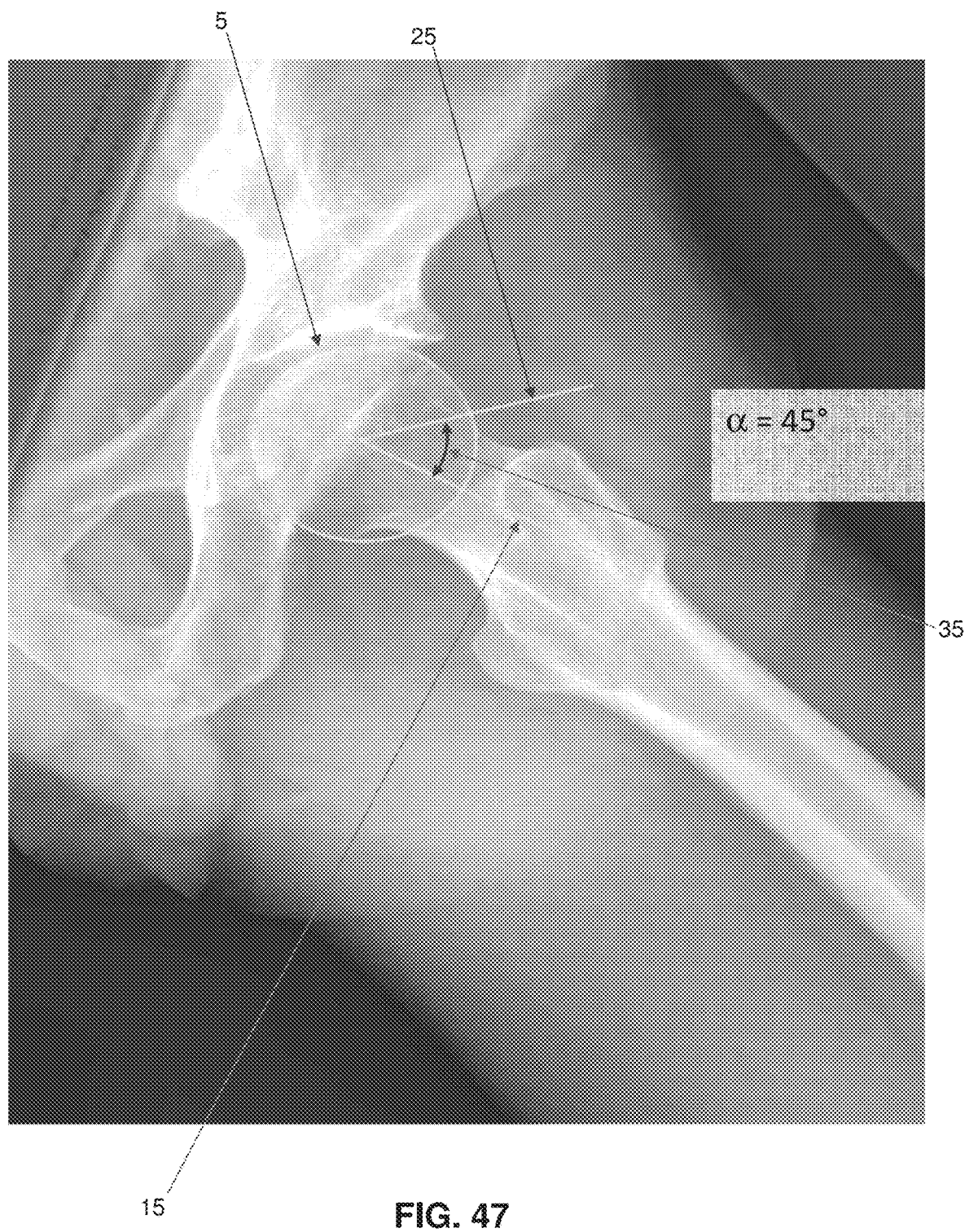

By way of example but not limitation, 2D images acquired intra-operatively by a C-arm X-ray machine 115 can be "merged" with one another so as to form a pseudo-3D model of the cam pathology. In this embodiment, C-arm X-ray machine 115 is oriented in multiple planes such that multiple 2D images of the cam pathology are acquired. Computer visual guidance system 125 then merges the acquired 2D images so as to form a partial 3D model of the cam pathology. In one form of this embodiment, a 2D outline 235 (FIG. 41) of the cam pathology is created with the 2D images. Once the images and corresponding outlines of the cam pathology are merged, a 3D representation of the cam pathology can be generated, for example, by geometric modeling of the outer surface of the cam pathology.

18. Adjustments

At this point, the surgeon can adjust the locations of the previously-determined femoral head, the previously-determined femoral neck, the previously-determined measured Alpha Angle, the previously-determined target Alpha Angle, the previously-determined resection curve start point, and the previously-determined resection curve end point, by simply dragging any of those elements to a desired location using the annotated image displayed by computer visual guidance system 125 (e.g., the touchscreen of a tablet device). If the user does adjust one or more of these locations, computer visual guidance system 125 will automatically re-compute the anatomical measurements and resection curve by utilizing the user-specified locations in place of the automatically-calculated locations. Subsequent images that are processed may or may not take into account the user-specified location changes to improve the overall accuracy and robustness of the measurements and resection curve location. For example, if the user specifies a larger femoral head radius, the femoral head detection algorithm may give preference to a larger detected femoral head. Also, if the user manually adjusts the resection curve end point, subsequent processed images may also provide a resection end point that is closer to the user's manual modification, i.e., if the user moves the resection end point more proximal, then the following images might also place the resection end point more proximal than would be the case by default. A good method for retaining relative distances between images (with regard to how far proximal or distal relative to the femoral head) would be to retain distances relative to the size of the femoral head. For example, a distance of "1.5 times the femoral head radius" should be a relatively constant distance between processed images, regardless of changes in zooming and rotation of the femur (as the femoral head radius is approximately spherical and should retain a relatively constant radius regardless of how it is imaged).

The Iterative Nature Of Computer Visual Guidance System 125

Significantly, the surgeon can iteratively check the progress of the boney resection by periodically updating the intra-operative X-ray image and the assessment, by computer visual guidance system 125, of the measurements associated with the bony pathology. In other words, and looking now at FIGS. 42-44 and 45-47, as the cam pathology surgery progresses, the surgeon periodically updates the intraoperative C-arm image. As this occurs, computer visual guidance system 125 automatically re-assesses the cam pathology (i.e., it automatically recalculates the Alpha Angle and the resection curve, etc.), and automatically annotates the X-ray image to show how the Alpha Angle changes from the original Alpha Angle toward the target Alpha Angle. This approach provides iterative guidance to the surgeon, enabling the surgeon to proceed with greater confidence as the cam pathology is reduced and, ultimately, reduces the possibility of under-resection of the cam pathology which could necessitate revision hip arthroscopy.

Note that the additional X-ray images acquired for this iterative process of repeatedly assessing the cam pathology as the surgery progresses may be done with the patient's leg and the C-arm X-ray machine remaining in the same position so as to provide updated assessments of the boney resection with the same X-ray projection; or the patient's leg may be re-positioned, and/or the C-arm X-ray machine moved, between X-ray images so as to provide updated assessments of the boney resection with differing X-ray projections.

Additional Feature: Provide Workflow Assistance

It can be important to document the cam pathology, both before and after removal. Computer visual guidance system 125 can be configured to provide step-by-step guidance to the surgeon to make sure that documenting images are captured at the appropriate points along the procedure, preferably along with automatic measurements.

Additional Feature: Provide Confirmation and Manual Correction

It is expected that computer visual guidance system 125 will never be 100% accurate or that the surgeon may make different choices for their patient based on experience and their understanding of the patient's condition. Since images end up being part of a medical record, computer visual guidance system 125 is configured to require manual confirmation from the surgeon before saving an image to the medical record. These interactions may be done in the sterile field through a variety of input devices including but not limited to:

wireless mouse (sterile draped)
wireless accelerometer with buttons (sterile draped)
remote control (sterile draped)
tablet (sterile draped)
camera buttons.

Figure 48:
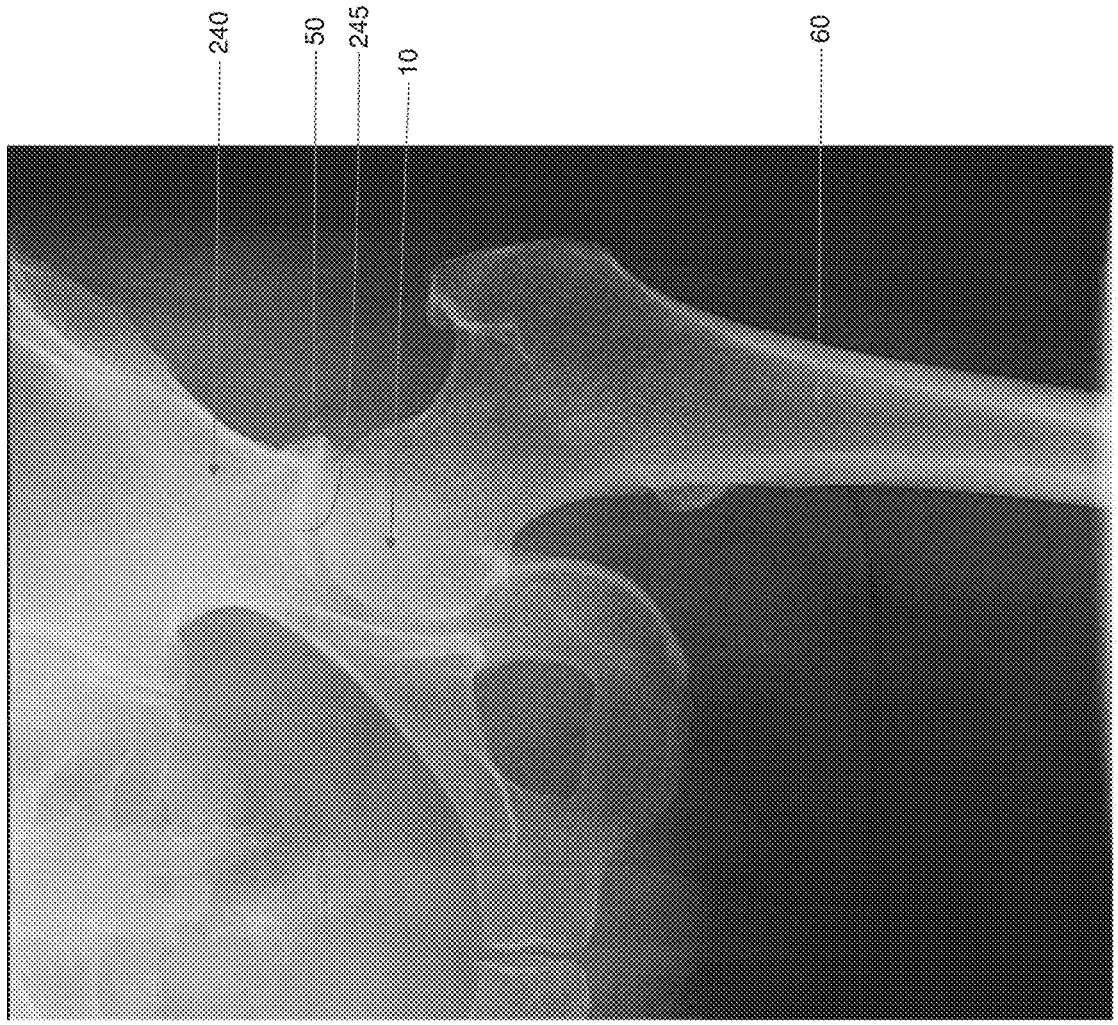
FIG. 48 is a schematic view showing pincer-type femoroacetabular impingement.

Method and Apparatus for the Treatment of Pincer-Type Femoroacetabular Impingement in a Hip Joint FIG. 48 is a schematic view of an acetabulum 240 comprising an acetabular cup 245 for receiving femoral head 10 of femur 60, and illustrates a pincer-type femoroacetabular impingement site 50 which needs to be debrided in order to treat the pincer-type femoroacetabular impingement.

The present invention comprises the provision and use of a novel computer visual guidance system which analyzes an X-ray image (e.g., an intra-operative C-arm X-ray image) to automatically measure features of the hip, such as the pincer pathology (e.g., by using a "Center Edge Angle" calculation, see below), and then annotates the X-ray image for use by the surgeon in treating the pincer pathology. The purpose of this invention is to guide the surgeon to an optimal resection of the pincer pathology which is causing the impingement. As noted above, arthroscopic resections are currently "eye-balled" and the surgeon has no objective way to define completion of the boney resection. This leads to over-resection and, most commonly, under-resection of the pincer pathology—which is a significant cause of revision hip arthroscopy. The present invention addresses this problem by providing means which automatically analyze an X-ray image with respect to a pincer pathology and then automatically annotates the X-ray image with guidance features which can be used by the surgeon in treating the pincer pathology.

More particularly, the present invention comprises a series of steps which start with an X-ray image and yields measurement of a feature of the hip (e.g., the Center Edge Angle) and an annotation correctly shown onto that X-ray image for the surgeon to be able to assess the pathology and progress towards proper resection.

In one preferred form of the invention, the invention utilizes the aforementioned methodology for treating a cam pathology, except that it is modified for treating a pincer pathology. More particularly, Steps 11-14 in the cam pathology procedure (FIG. 20) are replaced by the following Steps 11-14 for the pincer pathology treatment.

Step 11: Find The Transverse Pelvic Axis

Figure 49:
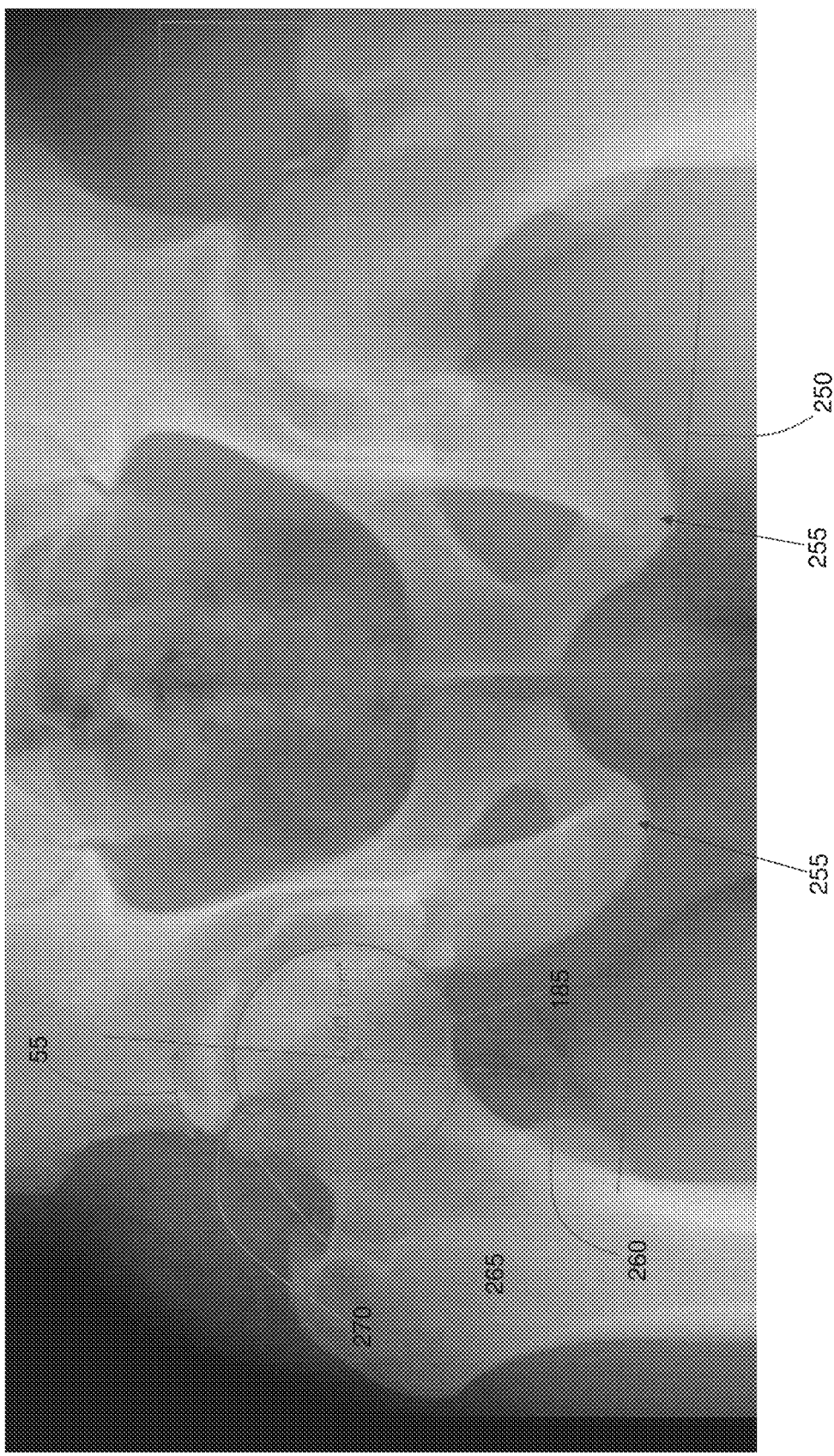
FIG. 49 is a schematic view showing a Center Edge Angle calculation.

Looking now at FIG. 49, the transverse pelvic axis 250 is located using standard image processing techniques, e.g., by drawing a line between the inferior apexes 255 of the ischium bones (or, alternatively, by drawing a line between the center of both femoral heads).

Step 12: Find The Perpendicular to the Transverse Pelvic Axis Which Extends Through the Center of the Femoral Head Still looking now at FIG. 49, the perpendicular 260 to the transverse pelvic axis 250 which extends through the center of the femoral head is located using standard image processing techniques, e.g., by extending a line from the center of the femoral head which is 90 degrees from the transverse pelvic axis.

Step 13: Find The Line Which Extends From the Lateral Acetabular Edge to the Center of the Femoral Head Still looking now at FIG. 49, the lateral acetabular edge line 265 which extends from the lateral edge 270 of the acetabular rim to the center 185 of the femoral head is located using standard image processing techniques, e.g., in an AP (Anterior-Posterior) view, by creating a line which passes from the lateral sourcil (the most supereolateral aspect of the sclerotic weight-bearing zone of the acetabulum) to the center of the femoral head.

Step 14: Measure The Center Edge Angle

Still looking now at FIG. 49, the Center Edge Angle 55 (i.e., the angle between the perpendicular 260 and the lateral acetabular edge line 265) is calculated, e.g., by measuring the angle formed between the portion of the perpendicular 260 on the superior side of the femoral head and the lateral acetabular edge line 265.

The Center Edge Angle of a "normal" person is typically between about 25 and about 35 degrees (i.e., the target Center Edge Angle is normally approximately 25 degrees to approximately 35 degrees).

Both the actual Center Edge Angle and the target Center Edge Angle can be automatically computed by computer visual guidance system 125 from an X-ray image and these features automatically annotated on the X-ray image for display to the surgeon. Furthermore, the difference between the actual Center Edge Angle and the target Center Edge Angle (i.e., the resection section) can be automatically identified by computer visual guidance system 125 and automatically annotated on the X-ray image for display to the surgeon.

Additional Concepts

Connectivity between the computer visual guidance system and the hip distraction equipment can provide medical personnel with useful information before, during and after a surgical procedure. For instance, the computer visual guidance system can be used to guide the medical personnel through the proper set-up of the distraction equipment, including assembly of the distraction equipment, attachment of the distraction equipment to the surgical bed, placement of other equipment in the surgical suite, proper patient positioning and attachment to the distraction equipment, information on use of the distraction equipment during the procedure, cleaning information, storage information and disassembly instructions. This information may be presented as a step-based system with prompts, or as a menu-driven system, or as a question-driven system, that provides users with only the requested information. The information may be presented as text, images (including video) and/or animation (including video), as appropriate, to convey the needed information.

The computer visual guidance system may be used in conjunction with sensors. By way of example but not limitation, if sensors are placed on the distraction equipment, the computer visual guidance system can utilize information about the distraction equipment and provide feedback to medical personnel. For instance, a set of sensors in the distraction equipment can detect the position of the distraction equipment in space. Information about the position of the heel or foot of the patient would be particularly useful as it is typically the attachment point for the patient to the distraction equipment. Additional information about the position of the patient's hip could be provided manually or through coordination with the C-arm X-ray device. Knowing this information would then provide information about the relative position of the patient's leg, and specifically their hip (e.g., whether it is in flexion, extension, abduction, adduction, internal or external rotation). Sensors can also be used to detect when traction is applied, either by measuring the position of the heel relative to the hip, or by a measurement of force. Alternatively, image analysis can be done to determine if the acetabulum and femoral head are dislocated allowing the deduction of whether traction is applied. This could provide medical personnel with feedback on the amount of tension applied to the patient, its direction of force (vector), and duration of the application of traction.

In as much as information about the position of the patient and the distraction equipment is available, it can also be used to help guide medical personnel during the procedure. For instance, while resecting a cam pathology on the femur, it is often important to move the patient's leg in order to fully visualize the pathology. With the ability to sense the position of the distraction equipment and therefore the patient's leg and hip position, the computer visual guidance system can prompt medical personnel on how to position the patient for optimal resection. Furthermore, the positioning of the hip and leg during this part of the procedure can be driven by pre-operative planning software that has been created to analyze and plan the resection. This pre-operative software may generate a series of images showing patient hip positions so that the surgeon and operative team can fully visualize the pathology, in particular the cam pathology. These views can be delivered to the computer visual guidance system and used to position the patient during the surgery to ensure visualization and review of the resection plan.

Use of the Novel Computer Visual Guidance System for Applications Other Than Alpha Angle Calculations and/or Center Edge Angle Calculations It should be appreciated that the novel computer visual guidance system of the present invention may be used for applications other than the specific Alpha Angle measurements and/or Center Edge Angle measurements discussed herein as related to the treatment of the hip joint.

By way of example but not limitation, the novel computer visual guidance system of the present invention may be used to measure other parameters in order to guide debridement of the femur and/or acetabulum during treatment of femoroacetabular impingement.

By way of further example but not limitation, the novel computer visual guidance system of the present invention may be used to guide debridement in joints other than the hip joint (e.g., to guide debridement of a surface of a humerus in order to prepare that surface for re-attachment of a torn rotator cuff, or to guide debridement of a surface of a bone in spinal surgery, etc.).

And by way of additional example but not limitation, the novel computer visual guidance system of the present invention may be used in non-arthroscopic procedures.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An arthroscopic visual guidance system for guiding arthroscopic removal of bone, wherein the arthroscopic visual guidance system comprises an intraoperative imaging device, an electronic communication interface, a display, and at least one processor that is configured to:
   obtain a first intraoperative digital image based on an output of the intraoperative imaging device resulting from the intraoperative imaging device imaging the bone during a bone removal procedure;
   automatically process pixel data of the first intraoperative digital image to annotate, by the at least one processor, the first intraoperative digital image with at least one annotation relating to removal of bone so as to create a first annotated digital image;
   display, via the display, a graphical user interface comprising the first annotated digital image;
   receive, from a user, at least one input associated with the graphical user interface for modifying at least a portion of the first annotated digital image;
   in response to the at least one input, modify the at least a portion of the first annotated digital image based on the at least one input;
   obtain a second intraoperative digital image based on an output of the intraoperative imaging device resulting from the intraoperative imaging device imaging the bone during the bone removal procedure, wherein the second intraoperative digital image shows partial removal of the bone;
   automatically process pixel data of the second intraoperative digital image to annotate, by the processor, the second intraoperative digital image so as to create a second annotated digital image; and
   display, via the display in real-time, the second annotated digital image.

2. The arthroscopic visual guidance system of claim 1, wherein the intraoperative imaging device comprises an intraoperative X-ray device.

3. The arthroscopic visual guidance system of claim 1, wherein the arthroscopic visual guidance system is configured to be used iteratively during the arthroscopic removal of the bone.

4. The arthroscopic visual guidance system of claim 1, wherein the first annotated digital image comprises a first resection line for indicating a proposed resection of the bone.

5. The arthroscopic visual guidance system of claim 4, wherein the first annotated digital image comprises a second resection line for indicating a smooth transition between the proposed resection of the bone and an adjacent portion of bone.

6. The arthroscopic visual guidance system of claim 1, wherein the arthroscopic visual guidance system comprises a general purpose computer having input and output functionality.

7. The arthroscopic visual guidance system of claim 6, wherein the arthroscopic visual guidance system comprises a touchscreen tablet.

8. The arthroscopic visual guidance system of claim 7, wherein the touchscreen tablet is located in a sterile field and is covered by a sterile drape.

9. The arthroscopic visual guidance system of claim 1, wherein the arthroscopic visual guidance system is configured to guide the surgeon through the arthroscopic removal of the bone in order to treat cam-type femoroacetabular impingement.

10. The arthroscopic visual guidance system of claim 9, wherein the bone comprises a cam pathology, and further wherein the arthroscopic visual guidance system is configured to automatically analyze, by the processor, the first intraoperative digital image so as to determine at least one measurement with respect to the cam pathology and automatically process pixel data of the first intraoperative digital image to annotate the first intraoperative digital image with at least one annotation relating to the at least one measurement determined with respect to the cam pathology.

11. The arthroscopic visual guidance system of claim 10, wherein the at least one measurement determined with respect to the cam pathology comprises an Alpha Angle measurement, and further wherein automatically processing pixel data of the first intraoperative digital image to annotate the first intraoperative digital image with at least one annotation relating to the at least one measurement determined with respect to the cam pathology comprises adding an Alpha Angle line to the first intraoperative digital image.

12. The arthroscopic visual guidance system of claim 11, wherein the arthroscopic visual guidance system is configured to determine the Alpha Angle measurement by: determining a first line which originates at a center of a femoral head and extends through a middle of a femoral neck; determining a second line which originates at the center of the femoral head and passes through a location which signifies a start of the cam pathology; and calculating an angle between the two lines.

13. The arthroscopic visual guidance system of claim 11, wherein automatically processing pixel data of the first intraoperative digital image to annotate the first intraoperative digital image with at least one annotation relating to the at least one measurement determined with respect to the cam pathology comprises inserting a target Alpha Angle line into the first intraoperative digital image.

14. The arthroscopic visual guidance system of claim 13, wherein the at least one annotation comprises a first resection line for indicating a proposed resection of the cam pathology and a second resection line for indicating a smooth transition between the proposed resection of the cam pathology and adjacent bone.

15. The arthroscopic visual guidance system of claim 14, wherein the first resection line starts at the Alpha Angle line and ends at the target Alpha Angle line, and the second resection line starts at the end of the first resection line and extends down the femoral neck.

16. The arthroscopic visual guidance system of claim 1, wherein the first annotated digital image comprises:
 a circle inscribing a femoral head;
 a centerpoint of the circle inscribing the femoral head;
 a line originating at a center of the femoral head and extending along a centerline of a femoral neck;
 an Alpha Angle line originating at the center of the femoral head and passing through a location at a start of a cam pathology;
 a line showing a target Alpha Angle; and
 a resection curve.

17. The arthroscopic visual guidance system of claim 1, wherein the arthroscopic visual guidance system is configured to guide the surgeon through the arthroscopic removal of the bone in order to treat pincer-type femoroacetabular impingement.

18. The arthroscopic visual guidance system of claim 17, wherein the bone comprises a pincer pathology, and further wherein the arthroscopic visual guidance system is configured to automatically analyze, by the at least one processor, the first intraoperative digital image so as to determine at least one measurement with respect to the pincer pathology and automatically process pixel data of the first intraoperative digital image to annotate the first intraoperative digital image with at least one annotation relating to the at least one measurement determined with respect to the pincer pathology.

19. The arthroscopic visual guidance system of claim 18, wherein the at least one measurement determined with respect to the pincer pathology comprises a Center Edge Angle measurement, and further wherein automatically processing pixel data of the first intraoperative digital image to annotate the first intraoperative digital image with at least one annotation relating to the at least one measurement determined with respect to the pincer pathology comprises inserting a Center Edge Angle line into the first intraoperative digital image.

20. The arthroscopic visual guidance system of claim 19, wherein automatically processing pixel data of the first intraoperative digital image to annotate the first intraoperative digital image with at least one annotation relating to the at least one measurement determined with respect to the pincer pathology comprises inserting a target Center Edge Angle line into the first intraoperative digital image.

21. The arthroscopic visual guidance system of claim 20, wherein the arthroscopic visual guidance system is configured to determine the Center Edge Angle by: determining a vertical line which originates at a center of a femoral head; determining a second line which originates at the center of the femoral head and passes through a location which signifies a start of the pincer pathology; and calculating an angle between the two lines.

22. The arthroscopic visual guidance system of claim 1, wherein obtaining the first intraoperative digital image comprises receiving the first intraoperative digital image from the intraoperative imaging device.

23. The arthroscopic visual guidance system of claim 1, wherein obtaining the first intraoperative digital image comprises generating the first intraoperative digital image from a video output of the intraoperative imaging device.

24. The arthroscopic visual guidance system of claim 1, wherein modifying the at least a portion of the first annotated digital image based on the at least one input comprises modifying the at least one annotation.

25. The arthroscopic visual guidance system of claim 24, wherein modifying the at least one annotation comprises adjusting a location of the at least one annotation.

26. The arthroscopic visual guidance system of claim 24, wherein the at least one annotation that is modified corresponds to at least one of a femoral head center, a femoral neck center, a measured Alpha Angle, a target Alpha Angle, a resection curve start point, and a resection curve end point.

27. A method for guiding an arthroscopic procedure for removal of bone, the method comprising:
 obtaining a first intraoperative digital image based on an output of an intraoperative imaging device resulting from the intraoperative imaging device imaging the bone during a bone removal procedure;
 automatically processing pixel data of the first intraoperative digital image to annotate, by an image processing system, the first intraoperative digital image with at least one annotation relating to removal of bone so as to create a first annotated digital image;
 displaying, via a display, a graphical user interface comprising the first annotated digital image;
 receiving, from a user, at least one input associated with the graphical user interface for modifying at least a portion of the first annotated digital image;
 in response to the at least one input, modifying the at least a portion of the first annotated digital image based on the at least one input;
 obtaining a second intraoperative digital image based on an output of the intraoperative imaging device resulting from the intraoperative imaging device imaging the bone during the bone removal procedure, wherein the second intraoperative digital image shows partial removal of the bone;
 automatically processing pixel data of the second intraoperative digital image to annotate, by the processing system, the second intraoperative digital image so as to create a second annotated digital image; and
 displaying, via the display, in real-time the second annotated digital image.

28. The method of claim 27, comprising imaging the bone iteratively during the arthroscopic removal of the bone.

29. The method of claim 28, comprising automatically creating, by the processing system, a new annotated digital image upon receiving a new digital image.

30. The method of claim 29, wherein the bone is moved relative to the intraoperative imaging device before the processing system receives the new digital image.

31. The method of claim 29, wherein the intraoperative imaging device is moved before the processing system receives the new digital image.

\* \* \* \* \*